(12) United States Patent
Venn-Watson

(10) Patent No.: US 11,992,473 B2
(45) Date of Patent: May 28, 2024

(54) COMPOSITIONS AND METHODS FOR DIAGNOSIS AND TREATMENT OF CONDITIONS RELATED TO THE QUALITY OF AGING AND LONGEVITY

(71) Applicant: Epitracker, Inc., San Diego, CA (US)

(72) Inventor: Stephanie Venn-Watson, San Diego, CA (US)

(73) Assignee: Epitracker, Inc., San Diego, CA (US)

(\*) Notice: Subject to any disclaimer, the term of this patent is extended or adjusted under 35 U.S.C. 154(b) by 476 days.

(21) Appl. No.: 17/086,165

(22) Filed: Oct. 30, 2020

(65) Prior Publication Data

US 2021/0052535 A1 Feb. 25, 2021

Related U.S. Application Data

(63) Continuation of application No. PCT/US2019/033175, filed on May 20, 2019.

(60) Provisional application No. 62/675,621, filed on May 23, 2018, provisional application No. 62/751,201, filed on Oct. 26, 2018, provisional application No. 62/838,234, filed on Apr. 24, 2019.

(51) Int. Cl.
*A61K 31/198* (2006.01)
*A23L 33/175* (2016.01)

(52) U.S. Cl.
CPC .......... *A61K 31/198* (2013.01); *A23L 33/175* (2016.08)

(58) Field of Classification Search
CPC .................................................. A61K 31/198
See application file for complete search history.

(56) References Cited

U.S. PATENT DOCUMENTS

| | | | |
|---|---|---|---|
| 4,252,159 A | 2/1981 | Maki | |
| 4,718,430 A | 1/1988 | Holzer | |
| 4,985,015 A | 1/1991 | Obermann et al. | |
| 5,318,521 A | 6/1994 | Slettenmark | |
| 5,449,688 A | 9/1995 | Wahl et al. | |
| 5,465,728 A | 11/1995 | Phillips | |
| 5,741,816 A | 4/1998 | Tsujihara et al. | |
| 6,214,875 B1 | 4/2001 | Yang | |
| 6,384,252 B1 | 5/2002 | Pageat | |
| 6,441,036 B1 | 8/2002 | Berge | |
| 6,544,541 B1 | 4/2003 | Zahradka | |
| 7,012,053 B1 | 3/2006 | Barnabas et al. | |
| 7,375,135 B2 | 5/2008 | Najib-Fruchart et al. | |
| 7,651,845 B2 | 1/2010 | Doyle et al. | |
| 8,030,348 B2 | 10/2011 | Sampalis | |
| 8,088,825 B2 | 1/2012 | Berge et al. | |
| 8,106,093 B2 | 1/2012 | Roe | |
| 8,251,904 B2 | 8/2012 | Zivitz et al. | |
| 8,759,558 B2 | 6/2014 | Holmeide et al. | |
| 8,827,957 B2 | 9/2014 | Searle et al. | |
| 9,282,760 B2 | 3/2016 | Bryhn et al. | |
| 9,295,637 B2 | 3/2016 | Perricone | |
| 9,561,206 B2 | 2/2017 | Venn-Watson | |
| 9,662,306 B2 | 5/2017 | Venn-Watson | |
| 9,687,461 B2 | 6/2017 | Venn-Watson | |
| 9,707,199 B2 | 7/2017 | Venn-Watson | |
| 9,713,600 B2 | 7/2017 | Venn-Watson | |
| 10,022,347 B2 | 7/2018 | Venn-Watson | |
| 10,111,849 B2 | 10/2018 | Henderson | |
| 10,238,618 B2 | 3/2019 | Venn-Watson | |
| 10,307,388 B2 | 6/2019 | Venn-Watson | |
| 10,449,170 B2 | 10/2019 | Venn-Watson | |
| 10,792,266 B2 | 10/2020 | Venn-Watson et al. | |
| 11,116,740 B2 | 9/2021 | Venn-Watson | |
| 2002/0156351 A1 | 10/2002 | Sagel | |
| 2003/0086869 A1 | 5/2003 | Stallings | |
| 2003/0203004 A1 | 10/2003 | Kelm et al. | |
| 2003/0203042 A1 | 10/2003 | Cook | |
| 2006/0154833 A1 | 7/2006 | Katou et al. | |
| 2006/0269495 A1 | 11/2006 | Popp et al. | |
| 2006/0275294 A1 | 12/2006 | Omoigui | |
| 2007/0088170 A1 | 4/2007 | Bryhn et al. | |
| 2009/0069331 A1 | 3/2009 | Vallance et al. | |
| 2009/0318369 A1 | 12/2009 | Paige et al. | |
| 2011/0077301 A1 | 3/2011 | Deminiere et al. | |
| 2011/0098358 A1 | 4/2011 | Fujimoto et al. | |
| 2011/0182943 A1 | 7/2011 | Kanwar et al. | |
| 2011/0190395 A1 | 8/2011 | Holmeide et al. | |
| 2011/0190702 A1 | 8/2011 | Stumber | |

(Continued)

FOREIGN PATENT DOCUMENTS

| | | |
|---|---|---|
| CN | 1939332 A | 4/2007 |
| CN | 102327368 A | 1/2012 |

(Continued)

OTHER PUBLICATIONS

Ballatore et al., "Carboxylic Acid (Bio)Isosteres in Drug Design". ChemMedChem. 2013, 8(3):385-395.
Partial European Search Report dated Apr. 13, 2021 for Application No. 18870336.7.
Aleshin et al. Peroxisome proliferator-activated receptor (PPAR)β/δ, a possible nexus of PPARα- and PPARγ-dependent molecular pathways in neurodegenerative diseases: review and novel hypotheses. Neurochem Int. (2013) 63:322-330.
Barba et al., Alzheimer's disease beyond the genomic era: nuclear magnetic resonance (NMR) spectroscopy-based metabolomics. J Cell Mol Med. 2008. 12(5a): 1477-1485.

(Continued)

*Primary Examiner* — Kevin E Weddington

(74) *Attorney, Agent, or Firm* — Knobbe, Martens, Olson & Bear LLP

(57) ABSTRACT

Compositions including metabolites that are small molecules, and salts and derivatives thereof, and methods for treatment or prophylaxis of conditions related to the quality of aging are provided, including compositions and methods for treating conditions that negatively impact longevity and the quality of aging, including inflammation, anemia, hyperglycemia, dyslipidemia, hyperinsulinemia, liver disease, iron overload, impaired skin integrity, wound healing, scarring, pain, allergies, sleep disorders and problems, and gastrointestinal disorders and problems.

20 Claims, 9 Drawing Sheets

(56) References Cited

U.S. PATENT DOCUMENTS

| | | |
|---|---|---|
| 2011/0201558 A1 | 8/2011 | Roe et al. |
| 2012/0071418 A1 | 3/2012 | Copeland et al. |
| 2012/0072236 A1 | 3/2012 | Atkin |
| 2012/0122940 A1 | 5/2012 | Hovland et al. |
| 2014/0303228 A1 | 10/2014 | Lawton et al. |
| 2015/0291523 A1 | 10/2015 | Ishikawa et al. |
| 2016/0045533 A1 | 2/2016 | Power et al. |
| 2016/0193170 A1 | 7/2016 | Venn-Watson et al. |
| 2016/0193171 A1 | 7/2016 | Venn-Watson |
| 2016/0193172 A1 | 7/2016 | Venn-Watson |
| 2016/0195558 A1 | 7/2016 | Venn-Watson et al. |
| 2016/0195559 A1 | 7/2016 | Venn-Watson |
| 2016/0324814 A1 | 11/2016 | Venn-Watson |
| 2017/0266144 A1 | 9/2017 | Venn-Watson |
| 2017/0319149 A1 | 11/2017 | Koehler et al. |
| 2018/0148682 A1 | 5/2018 | Ross |
| 2018/0185316 A1 | 7/2018 | Venn-Watson |
| 2018/0296518 A1 | 10/2018 | Venn-Watson et al. |
| 2018/0311195 A1 | 11/2018 | Venn-Watson |
| 2018/0311303 A1 | 11/2018 | Maione et al. |
| 2019/0054052 A1 | 2/2019 | Shchepinov |
| 2019/0117607 A1 | 4/2019 | Venn-Watson et al. |
| 2019/0240181 A1 | 8/2019 | Venn-Watson |
| 2019/0358183 A1 | 11/2019 | Venn-Watson |
| 2020/0222351 A1 | 7/2020 | Dhamane et al. |
| 2020/0345676 A1 | 11/2020 | Venn-Watson et al. |
| 2021/0046034 A1 | 2/2021 | Venn-Watson |
| 2021/0330734 A1 | 10/2021 | Venn-Watson |
| 2021/0346419 A1 | 11/2021 | Venn-Watson |
| 2021/0386710 A1 | 12/2021 | Venn-Watson |
| 2023/0132955 A1 | 5/2023 | Venn-Watson |
| 2023/0201153 A1 | 6/2023 | Venn-Watson |
| 2023/0293491 A1 | 9/2023 | Venn-Watson |

FOREIGN PATENT DOCUMENTS

| | | |
|---|---|---|
| DE | 2615061 | 10/1977 |
| DE | 102010010666 A1 | 9/2011 |
| EP | 1000071 A1 | 5/2000 |
| EP | 1020179 A2 | 7/2000 |
| EP | 3301090 A1 | 4/2018 |
| JP | S60172925 | 9/1985 |
| JP | S61015809 A | 1/1986 |
| JP | S62012716 | 1/1987 |
| JP | S63099063 | 4/1988 |
| JP | H06172168 A | 6/1994 |
| JP | 2003160486 A | 6/2003 |
| JP | 2004115438 A | 4/2004 |
| JP | 2005523331 A | 8/2005 |
| JP | 2008255022 A | 10/2008 |
| JP | 2008540393 | 11/2008 |
| JP | 2010260833 A | 11/2010 |
| JP | 2011528350 A | 11/2011 |
| JP | 2014080432 A | 5/2014 |
| JP | 2015010067 A | 1/2015 |
| JP | 2016504403 | 2/2016 |
| JP | 2017200910 A | 11/2017 |
| JP | 2017536879 A | 12/2017 |
| KR | 20170087813 A | 7/2017 |
| KR | 201701009096 A | 9/2017 |
| KR | 102087634 B1 | 3/2020 |
| WO | WO 1996/26647 | 9/1996 |
| WO | WO 1996/32850 | 10/1996 |
| WO | WO 1999/001103 | 1/1999 |
| WO | WO 1999/002485 | 1/1999 |
| WO | WO 2000/040217 | 7/2000 |
| WO | WO 2004/057982 | 7/2004 |
| WO | WO 2004/069240 | 8/2004 |
| WO | WO 2005/099483 | 10/2005 |
| WO | WO 2005/120485 | 12/2005 |
| WO | WO 2006/038063 | 4/2006 |
| WO | WO 2006/117668 | 11/2006 |
| WO | WO 2007/002365 | 1/2007 |
| WO | WO 2007/100435 | 9/2007 |
| WO | WO 2008/114732 | 9/2008 |
| WO | WO 2010/123930 | 10/2010 |
| WO | WO 2012/001336 | 1/2012 |
| WO | WO 2012/069790 | 5/2012 |
| WO | WO 2013/007700 | 1/2013 |
| WO | WO 2014/108573 | 7/2014 |
| WO | WO 2014/179341 | 11/2014 |
| WO | WO 2015/110977 | 7/2015 |
| WO | WO 2015/140545 | 9/2015 |
| WO | WO 2015/157514 | 10/2015 |
| WO | WO 2016/111843 | 7/2016 |
| WO | WO 2017/186928 | 11/2017 |
| WO | WO 2018/157013 | 8/2018 |
| WO | WO 2019/212196 | 11/2019 |
| WO | WO 2019/222254 | 11/2019 |
| WO | WO 2019/226572 | 11/2019 |
| WO | WO 2020/146263 | 7/2020 |
| WO | WO 2020/154173 | 7/2020 |

OTHER PUBLICATIONS

Bhargava et al., "Metabolic alterations in multiple sclerosis and the impact of vitamin D supplementation", JCI Insight. 2017, 2(19): 1-13.

Bogdanov et al., "Metabolomic profiling to develop blood biomarkers for Parkinson's disease", Brain 2008. 131(2): 389-396.

Bonomo et al., "Iron overload potentiates diet-induced hypercholesterolemia and reduces liver PPAR-α expression in hamsters". J Biochem Mol Toxicol. (2012) 26(6): 224-229.

Borodina et al., "The biology of ergothioneine, an antioxidant nutraceutical". Nutri Res Reviews (2020) 33: 190-217.

Chiba et al., Topical application of PPARα (but not β/δ or γ) suppresses atopic dermatitis in NC/Nga mice. Allergy (2012) 67: 936-942.

Choi et al., The nuclear receptor PPARs as important regulators of T-cell functions and autoimmune diseases. Mol Cell. (2012) 33(3): 217-222.

Database WPI, "Pentadecanoic acid compound", Clarivate Analytics, AN: 2017-637713, Clarivate Analytics, dated: Jul. 2017; 2 pages.

Database WPI, "Immunosuppressive agent . . . ", AN: 1994-238645, Clarivate Analytics, dated: 1994; 2 pages.

Database WPI, "An effective Saururus chinensisrhizome part . . . ", AN: 2012-B90946, Clarivate Analytics, dated: 2012; 2 pages.

Database WPI, "An anti-aging composition . . . ", AN: 2004-310751, Clarivate Analytics, dated: 2004; 2 pages.

Durzan D.J., "Arginine, scurvy and Cartier's tree of life". J Ethnobio Ethnomed. 2009. 5(1): 1-16.

Ghannadi et al., "An Investigation of the Analgesic and Anti-Inflammatory Effects of Nigella sativa Seed Polyphenols", J Med Food. 2005, 8(4): 488-493.

Hosokawa et al., Fucoxanthin induces apoptosis and enhances the antiproliferative effect of the PPARγ ligand, troglitazone, on colon cancer cells. BBA Gen Subj. (2004) 675: 113-119.

Hwang et al., "Inhibitory Effects of 4-Guanidinobutyric Acid against Gastric Lesions", Biomol Ther. 2012, 20(2): 239-244.

Janani et al., PPAR gamma gene—a review. Diab Metab Synd Clin Res Rev. (2015) 9: 46-50.

Jeon et al., "S-adenosylhomocysteine treatment of adult female fibroblasts alters X-chromosome inactivation and improves in vitro embryo development after somatic cell nuclear transfer", Reproduction, (2008) 135: 815-828.

Jové et al. Metabolomics of human brain aging and age-related neurodegenerative diseases. J Neuropathol Exp Neurol. 2014, 73(7): 640-657.

Kaddurah-Daouk, et al., Metabolomics: A global biochemical approach to the study of central nervous system diseases. Neuropsychopharmacol 2009. 34(1): 173-186.

Leibovitz et al., PPAR activation: a new target for the treatment of hypertension. J Cardio Pharmacol. (2007) 50: 120-125.

Madrazo et al., The PPAR trio: Regulators of myocardial energy metabolism in health and disease. J Mol Cell Cariol. (2008) 44: 968-975.

(56) References Cited

OTHER PUBLICATIONS

Milam et al., PPAR-γ agonists inhibit profibrotic phenotypes in human lung fibroblasts and bleomycin-induced pulmonary fibrosis. Am J Physiol Lung Cell Mol Physiol. (2008) 94: L891-L901.
Nilsson S., "Long-term treatment with methenamine hippurate in recurrent urinary tract infection", Acta Med Scand. (1975) 198(1-2): 81-85.
Pubchem. CID 325395, Mar. 26, 2005; pp. 1-13; retrieved from the Internet <URL: https://pubchem.ncbi.nlm.nih.gov//compound/325395>.
Salek et al., A metabolomic study of the CRND8 transgenic mouse model of Alzheimer's disease. Neurochem Int. 2010. 56(8): 937-947.
Sertznig et al., Peroxisome proliferator-activated receptors (PPARs) and the human skin. Am J Clin Dermatol. (2008) 9: 15-31.
Shaw C., "Possible Modulation by Glutathione of Glutamatergic", in Glutathione in the Nervous System, CRC Press, 1998. Chapter 7, pp. 140-142.
Sokolowska et al., Peroxisome proliferator-activated receptor gamma (PPAR-gamma) and their role in immunoregulation and inflammation control. Postepy Higieny (2005) 59: 472-484; Abstract in 2 pages.
Sotgia et al., "Hercynine content in widely consumed commercial beverages". LWT Food Science Tech. Dec. 1, 2018;98: 465-469.
Trifilieff et al., PPAR-α and -γ but not -δ agonists inhibit airway inflammation in a murine model of asthma: in vitro evidence for an NF-kβ-independent effect. Br J Pharmacol. (2003) 139: 163-171.
Trushina et al., Identification of altered metabolic pathways in plasma and CSF in mild cognitive impairment and Alzheimer's disease using metabolomics. PLoS One 2013. 8(5): e63644 in 13 pages.
Trushina et al., Recent advances in the application of metabolomics to Alzheimer's disease. Bioch Biophy Acta. 2014.1842(8): 1232-1239.
Wei et al., Peroxisome proliferator-activated receptor γ: innate protection from excessive fibrinogenesis and potential therapeutic target in systemic sclerosis. Curr Opin Rheumatol. (2010) 22(6): 671-676.
Extended European Search Report dated Feb. 24, 2022 for Application No. 19808192.9.
Hodge et al., "Plasma phospholipid and dietary fatty acids as predictors of type 2 diabetes: Interpreting the role of linoleic acid." Am J Clin Nutrition (2007) 86(1): 189-197.
Meikle et al., "Plasma Lipid Profiling Shows Similar Associations with Prediabetes and Type 2 Diabetes". PloS one, 2013, 8(9), e74341; 43 pages.
Abdullah et al., "Recommended dairy product intake modulates circulating fatty acid profile in healthy adults: a multi-centre crossover study", Br J Nutr. 113(3):435-444.
Adams et al., "Hemochromatosis and iron-overload screening in a racially diverse population." New Engl J Med. 2005, 352(17):1769-1778.
Adams et al., "A diagnostic approach to hyperferritinemia with a non-elevated transferrin saturation", J Hepatol. 2011, 55(2):453-458.
Ahmad et al., "Interaction of Osteopontin with IL-18 in Obese Individuals: Implications for Insulin Resistance". PLoS One 2013, 8(5):e63944 in 9 pages.
Akbar et al., Alterations in Hepatic FGF21, Co-Regulated Genes, and Upstream Metabolic Genes in Response to Nutrition, Ketosis and Inflammation in Peripartal Holstein Cows, PLoS One 2015, 10(10):e0139963 in 16 pages.
Akhter, J. MD; Asthma-cure, 2017, https://www.scientificamerican.com/article/can-asthma-be-cured-what/ in 7 pages.
Aksenov et al., "Metabolite Content Profiling of Bottlenose Dolphin Exhaled Breath", Anal Chem 2014, 86(21):10616-10624.
Altamura et al., "Iron toxicity in diseases of aging: Alzheimer's disease, Parkinson's disease and atherosclerosis." J Alzheimer's Dis. 2009, 16(4):879-895.

Anderson et al., "Cholesterol and mortality: 30 years of follow-up from the Framingham Study." JAMA (1987) 257(16): 2176-2180.
Angulo et al., "Liver Fibrosis, but no Other Histologic Features, Associates with Long-term Outcomes of Patients With Nonalcoholic Fatty Liver Disease". Gastroenterology. 2015, 149(2):389-397.
Barcellini et al., "Clinical Applications of Hemolytic Markers in the Differential Diagnosis and Management of Hemolytic Anemia". Disease Markers (2015) Article ID 635670 in 7 pages.
Barish et al., "PPARδ: a dagger in the heart of the metabolic syndrome", J Clin Invest. 2006, 116(3):590-597.
Barros et al., "Prey and feeding patterns of resident bottlenose dolphins (Tursiops truncatus) in Sarasota Bay, Florida", J Mammal. 1998, 79:1045-1059.
Bartke et al., "Bioactive sphingolipids: metabolism and function". J Lipid Res. (2009) 50(Suppl):S91-S96.
Batista et al., "Structural Insights into Human Peroxisome Proliferator Activated Receptor Delta (PPAR-Delta) Selective Ligand Binding", PLoS One. 2012, 7(5):e33643 in 7 pages.
Beaton et al., "Treatment of Hyperferritinemia", Ann Hepatol. 2012, 11(3):294-300.
Benatar et al., "The effects of changing dairy intake on trans and saturated fatty acid levels—results from a randomized controlled study". Nutr J. 2014, 13:32 in 10 pages.
Berens-McCabe et al., "Prey selection in a resident common bottlenose dolphin (Tursiops truncatus) community in Sarasota Bay, Florida", Marine Biol. 2010, 157:931-942.
Bettcher et al., "MCP-1 and eotaxin-1 selectively and negatively associate with memory in MCI and Alzheimer's disease dementia phenotypes", Alzheimers Dement (Amst). 2016, 3:91-97.
Bossù et al., "Interleukin-18 produced by peripheral blood cells is increased in Alzheimer's disease and correlates with cognitive impairment". Brain Behav Immun. 2008, 22(4):487-492.
Calder et al., "n-3 polyunsaturated fatty acids, inflammation, and inflammatory diseases." Am J Clin Nutr. 2006, 83(6 suppl):1505S-1519S.
Calder P.C., "Long-chain polyunsaturated fatty acids and inflammation", Scandinavian J Food Nutr. 2006, 50(S2):54-61.
Camaschella C., "Iron-Deficiency Anemia", New Engl J Med. (2015) 372(19):1832-1843.
Cater et al., "Behenic acid is a cholesterol-raising saturated fatty acid in humans." Am J Clin Nutr. 2001, 73(1):41-44.
Cheng et al., "Distinct Metabolomic Signatures Are Associated with Longevity in Humans.", Nat Commun. 2015, 6:6791 in 22 pages.
Choi et al., "Dairy consumption and risk of type 2 diabetes mellitus in men: a prospective study". Arch Intern Med. 2005, 165(9):997-1003.
Colegrove K., Histomorphology of the bottlenose dolphin (Tursiops truncatus) pancreas and association of increasing islet ß-cell size with chronic hypercholesterolemia. Gen Comp Endocrinol. 2015, 214:17-23.
Collino et al., "Metabolic Signatures of Extreme Longevity in Northern Italian Centenarians Reveal a Complex Remodeling of Lipids, Amino Acids, and Gut Microbiota Metabolism". PLoS One. 2013, 8(3):e56564 in.
Corso et al., Corso et al., "Serum Amino Acid Profiles in Normal Subjects and in Patients with or at Risk of Alzheimer Dementia", Dement Geriatr Cogn Disord Extra. 2017, 7(1):143-159.
Craik J., GLUT-1 mediation of rapid glucose transport in dolphin (Tursiops truncatus) red blood cells. Am J Physiol. 1998, 274(1 Pt 2):R112-R119.
Croes et al., Formation of a 2-methyl-branched fatty aldehyde during peroxisomal alpha-oxidation. FEBS Lett. 1997, 412(3):643. 645.
Cronet et al., "Structure of the PPARα and -γ Ligand Binding Domain in Complex with AZ 242; Ligand Selectivity and Agonist Activation in the PPAR Family", Structure. 2001, 9(8):699-706.
Cusi et al., "Long-Term Pioglitazone Treatment for Patients With Nonalcoholic Steatohepatitis and Prediabetes or Type 2 Diabetes Mellitus: A Randomized Trial". Ann Intern Med. 2016, 165(5):305-315.

(56) References Cited

OTHER PUBLICATIONS

Daak et al., "Effect of omega-3 (n-3) fatty acid supplementation in patients with sickle cell anemia: randomized, double-blind, placebo-controlled trial". Am J Clin Nutr. 2013, 97(1):37-44.
Das Undurti N., "Arachidonic acid in health and disease with focus on hypertension and diabetes mellitus: A review", J Adv Res. 2018, 11:43-55.
Diehl et al., "Cause, Pathogenesis, and Treatment of Nonalcoholic Steatohepatitis". N Engl J Med. 2017, 377(21):2063-2072.
Di Paolo et al., "Linking Lipids to Alzheimer's Disease: Cholesterol and Beyond", Nat Rev Neurosci. 2011, 12(5):284-296.
Dongiovanni et al., "Iron in fatty liver and in the metabolic syndrome: a promising therapeutic target". J Hepatol. 2011, 55:920-932.
Dursun et al., 2015, The interleukin 1 alpha, interleukin 1 beta, interleukin 6 and alpha-2-macroglobulin serum levels in patients with early or late onset Alzheimer's disease, mild cognitive impairment or Parkinson's disease. J Neuroinflammunol. 2015, 283: 50-57.
Ekstedt et al., "Fibrosis stage is the strongest predictor for disease-specific mortality in NAFLD after up to 33 years of follow-up." Hepatology. 2015; 61(5): 1547-1554.
Ellervik et al., "Prevalence of hereditary haemochromatosis in late-onset type 1 diabetes mellitus: a retrospective study", Lancet 2001, 358(9291):1405-1409.
Evans et al., "NAD+ metabolite levels as a function of vitamins and calorie restriction: evidence for different mechanisms of longevity." BMC Chem Biol. 2010, 10:2 in 10 pages.
Fargion et al., "Hyperferritinemia, iron overload, and multiple metabolic alterations identify patients at risk for nonalcoholic steatohepatitis". Am J Gastroenterol. 2001, 96(8):2448-2455.
Favé et al., "Physicochemical properties of lipids: new strategies to manage fatty acid bioavailability". Cell Mol Biol. 2004, 50(7):815-831.
FDA Guidance for Industry. "Estimating the maximum safe starting dose in initial clinical trials for therapeutics in adult healthy volunteers." U.S. Food and Drug Administration, Jul. 2005 in 30 pages.
FDA (2017) FDA drug safety communication: FDA warns about serious liver injury with Ocaliva (obeticholic acid) for rare chronic liver disease. Accessed Dec. 5, 2017 https://www.fda.gov/Drugs/DrugSafety/ucm576656.htm in 4 pages.
Fernandes et al., "Relationship between Acute Phase Proteins and Serum Fatty Acid Composition in Morbidly Obese Patients", Dis Markers 2013, 35(2):104-112.
Forman et al., "Hypolipidemic drugs, polyunsaturated fatty acids, and eicosanoids are ligands for peroxisome proliferator-activated receptors α and δ", Proc Natl Acad Sci U.S.A., 1997, 94(9):4312-4317.
Forouhi et al., "Differences in the Prospective Association Between Individual Plasma Phospholipid Saturated Fatty Acids and Incident Type 2 Diabetes: The EPIC-InterAct Case-Cohort Study", Lancet Diabetes Endocrinal, 2014, 2:810-818.
Fujiwara et al., "Biology of Heme in mammalian Erythroid Cells and Related Disorders". BioMed Res Int'l. (2015) Article ID 278536 in 9 pages.
Gabrielsen et al., "Adipocyte iron regulates adiponectin and insulin sensitivity". J Clin Invest. 2012, 122(10):3529-3540.
Gibson RA., "Australian fish—An excellent source of both arachidonic acid and ω-3 polyunsaturated fatty acids", Lipids 1983, 18(11):743-752.
Giunta et al., "Inflammaging as a prodrome to Alzheimer's disease", J Neuroinflammation 2008, 5:51; 15 pages.
Glauber et al., "Adverse metabolic effect of omega-3 fatty acids in non-insulin-dependent diabetes mellitus", Ann Intern Med. 1988, 108(5):663-668.
Gonzalez-Covarrubias et al., "Lipidomics of familial longevity". Aging Cell. 2013, 12(3):426-434.
Gonzalez-Covarrubias V., "Lipidomics in longevity and healthy aging". Biogerontology. 2013, 14(6):663-672.
Ghosh et al., "PAI-1 in tissue fibrosis." J Cell Physiol. (2011) 227(2):493-507.
Grundy et al., "Definition of metabolic syndrome: Report of the National Heart, Lung, and Blood Institute/American Heart Association conference on scientific issues related to definition", Circulation. 2004, 109(3):433-438.
Gunstone et al. [Eds.], "A review of even-chain fatty acid metabolism and the role of arachidic acid (C20:0) and lignoceric acid (C24:0) in health and disease", The Lipid Handbook, Gunstone et al. [Eds.] 3rd Edition, 2008, 604-635.
Hallgren et al., "Lymphocyte phytohemagllutinin responsiveness, immunoglobulins and autoantibodies in aging humans." J Immunol. (1973) 111:1101-1107.
Hall et al., "Annual, seasonal and individual variation in hematology and clinical blood chemistry profiles in bottlenose dolphins (*Tursiops truncatus*) from Sarasota Bay, Florida", Comp Biochem Physiol A Mol Integr Physiol. 2007, 148(2):266-277.
Hannun et al., "Principles of bioactive lipid signalling: lessons from sphingolipids", Nat Rev Mol Cell Biol. 2008, 9(2):139-150.
Hassanali et al., "Dietary supplementation of n-3 PUFA reduces weight gain and improves postprandial lipaemia and the associated inflammatory response in the obese JCR:LA-cp rat", Diabetes Obes Metab. 2010, 12(2):139-147.
Hebbel et al., A Systems Biology Consideration of the Vasculopathy of Sickle Cell Anemia: The Need for Multi-Modality Chemo-Prophylaxis, Cardiovsc Hematol Disord Drug Targets (200() 9(4):271-291.
Heneka et al., "Neuroinflammation in Alzheimer's Disease", Lancet Neurol. 2015, 14(4):388-405.
Hodson et al., "Fatty acid composition of adipose tissue and blood in humans and its use as a biomarker of dietary intake", Prog Lipid Res. 2008, 47:348-380.
Holmes et al., "Systemic inflammation and disease progression in Alzheimer disease". Neurology 2009, 73(10):768-774.
International Diabetes Federation (2006) The IDF consensus worldwide definition of the Metabolic Syndrome. Brussels, Belgium., in 24 pages.
Jaruvongvanich et al., "Outcome of phlebotomy for treating non-alcoholic fatty liver disease: a systematic review and meta-analysis". Sauid J Gastroenterol. 2016, 22(6):407-414.
Jenkins et al., "A Review of Odd-Chain Fatty Acid Metabolism and the Role of Pentadecanoic Acid (C15:0) and Heptadecanoic Acid (C17:0) in Health and Disease", Molecules (2015) 20(2):2425-2444.
Johnson et al., "Use of phlebotomy treatment in Atlantic bottlenose dolphins with iron overload". J Am Vet Med Assoc. 2009, 235(2):194-200.
Kanda et al., "MCP-1 contributes to macrophage infiltration into adipose tissue, insulin resistance, and hepatic steatosis in obesity", J Clin Invest. 2006, 116(6):1494-1505.
Kersten et al., "Roles of PPARs in health and disease", Nature. 2000, 405(6785):421-424.
Kiyota et al., "CCL2 Accelerates Microglia-Mediated Aβ Oligomer Formation and Progression of Neurocognitive Dysfunction". PLoS One. 2009, 4:e6197 in 12 pages.
Klock et al,"Sodium ascorbyl phosphate shows in vitro and in vivo efficacy in the prevention and treatment of acne vulgaris", International Journal of Cosmetic Science, 2005, 27(3):171-176.
Krachler et al., "Fatty Acid Profile of the Erythrocyte Membrane Preceding Development of Type 2 Diabetes Mellitus", Nutri Metabol Cardiovasc Diseases, (2008) 18(7):503-510.
Kratz et al., The relationship between high-fat dairy consumption and obesity, cardiovascular, and metabolic disease. Eur J Nutr. (2013) 52: 1-24.
Kratz et al., "Dairy fat intake is associated with glucose tolerance, hepatic and systemic insulin sensitivity, and liver fat but not β-cell function in humans", Am J Clin Nutr. 2014, 99(6):1385-1396.
Kriesberg et al., Cholesterol metabolism and aging, Am J Med. (1987) 82: 54-60.
Kristal et al., "Metabolomics: Opening Another Window into Aging". Sci Aging Knowledge Environ. 2005, 26:pe19 in 2 Pages.

(56) References Cited

OTHER PUBLICATIONS

Kühn et al., 2012, "Effect of Multipeak Spectral Modeling of Fat for Liver Iron and Fat Quantification: Correlation of Biopsy with MR Imaging Results". Radiology. 2012, 265(1):133-142.

LaBrecque et al., "World Gastroenterology Organisation global guidelines: Nonalcoholic fatty liver disease and nonalcoholic steatohepatitis". J Clin Gastroenterol. 2014, 48(6):467-473.

Lagerstedt et al., "Quantitative determination of plasma c8-c26 total fatty acids for the biochemical diagnosis of nutritional and metabolic disorders", Mol Genet Metab. 2001, 73(1):38-45.

Lai et al., "The protective effects and genetic pathways of thorn grape seeds oil against high glucose-induced apoptosis in pancreatic beta-cells", BMC Complement Altern Med. 2014, 14:10 (7 pages).

Lee et al., "PPARα and glucocorticoid receptor synergize to promote erythroid progenitor self-renewal", Nature 2005, 522:474-477.

Lefebvre et al., "Antifibrotic Effects of the Dual CCR2/CCR5 Antagonist Cenicriviroc in Animal Models of Liver and Kidney Fibrosis". PLoS One. 2016. 11(6):e0158156 in 19 pages.

Leyton et al., "Differential oxidation of saturated and unsaturated fatty acids in vivo in the rat". Br J Nutr. 1987, 57(3):383-393.

Liao et al., "Pioglitazone and cardiovascular outcomes in patients with insulin resistance, pre-diabetes and type 2 diabetes: a systematic review and meta-analysis". BMJ Open. 2017, 7(1):e013927 in 13 pages.

Liu et al., "Serum biomarkers for nonalcoholic fatty liver disease: Are we there yet?", Hepatology. 2017, 65(1):8-11.

Livrea et al., "Oxidative stress and antioxidant status in ß-thalassemia major: iron overload and depletion of lipid-soluble antioxidants." Blood. 1996, 88(9):3608-3614.

Loomba et al., "The ASK1 inhibitor selonsertib in patients with nonalcoholic steatohepatitis: A randomized, phase 2 trial". Hepatology. 2018, 67(2):549-559; avail online Dec. 2017; in 11 pages.

Luquet et al., "Roles of PPAR δ in lipid absorption and metabolism: a new target for the treatment of type 2 diabetes", Biochim Biophys Acta. 2005, 1740:313-317.

Luzia et al., "The influence of season on the lipid profiles of five commercially important species of Brazilian fish", Food Chem. 2003, 83(1):93-97.

Ma et al., "Organization of the mammalian metabolome according to organ function, lineage specialization, and longevity". Cell Metab. 2015, 22(2):332-343.

Madsen et al., "Tetradecylthioacetic acid prevents high fat diet induced adposity and insulin resistance", J Lipid Res. 2002, 43:742-750.

Magnusdottir et al., "Plasma alkylresorcinols C17:0/C21:0 ratio, a biomarker of relative whole-grain rye intake, is associated to insulin sensitivity: a randomized study", Eur J Clin Nutr. 2014, 68(4):453-458.

Månsson H.L., "Fatty acids in bovine milk fat". Food Nutr Res. 2008, 52:4 in 3 pages.

Martin-Jiménez et al., Relationship between obesity, Alzheimer's disease, and Parkinson's disease: an astrocentric view. Publ. online Oct. 28, 2016; Mol Neurobiol. 2017, 54(9):7096-7115.

Maruyama et al., "Differences in Serum Phospholipid Fatty Acid Compositions and Estimated Desaturase Activities Between Japanese Men With and Without Metabolic Syndrome", J Atheroscler Thromb. 2008, 15(6):306-313.

Mayneris-Perxachs et al., "Plasma fatty acid composition, estimated desaturase activities, and their relation with the metabolic syndrome in a population at high risk of cardiovascular disease". Clinical Nutrition. 2013, HTTP://dx.doi.org/10.1016/j.clnu.2013.03.001.

Mayo Clinic, Asthma, 2017, https://www.mayoclinic.org/diseases-conditions/asthma/basics/treatment/con-20026992 in 6 pages.

Mayo Clinic, Cholesterolgallstones, 2017, https://www.mayoclinic.org/diseases-conditions/gallstones/diagnosis-treatment/drc-20354220 in 3 pages.

Mazzaro et al., "Iron indices among bottlenose dolphins (*Tursiops truncatus*)". Comp Med. 2012, 62(6):508-515.

McGeer et al., "Inflammation, Antiinflammatory Agents, and Alzheimer's Disease: The Last 22 Years". J Alzheimers Dis. 2016, 54(3):853-857.

McGowen M., "Dolphin genome provides evidence for adaptive evolution of nervous system genes and a molecular rate slowdown", Proc Biol Sci. 2012, 279(1743):3643-3651.

McMurchie E.J., "Dietary lipids and the regulation of membrane fluidity and function". Publisher: Alan R. Liss, Inc.; Physiol Reg Memb Fuid. 1988, 189-237.

Mennen et al., "Possible protective effect of bread and dairy products on the risk of the metabolic syndrome", Nutrition Res. 2000, 20(3):335-347.

Mi, "Myocardial Infarction", 2017, MedlinePlus Medical Encyclopedia; URL: <https://medlineplus.gov/ency/article/000195.htm> in 7 pages.

Miyake et al., "Maternal consumption of dairy products, calcium, and vitamin D during pregnancy and infantile allergic disorders." Ann Allergy Asthma Immunol. (2014) 113(1): 82-87. (Abstract p. S224).

Montoliu et al., Serum profiling of healthy aging identifies phosphor- and sphingolipid species as markers of human longevity. Aging (Albany NY). 2014, 6(1):9-25.

Morsy et al., "Can eicosapentaenoic acid maintain the original ribavirin dose or affect the response during the treatment course of chronic hepatitis C virus (HCV) patients?", Turk J Gastroenterol. 2016, 27:55-61.

Nanji et al., "Dietary saturated fatty acids reverse inflammatory and fibrotic changes in rat liver despite continued ethanol administration." J Pharmacol Exp Ther. 2001, 299(2):638-644.

Nelson et al., "Relationship between the pattern of hepatic iron deposition and histologic severity in nonalcoholic fatty liver disease". Hepatology. 2011, 53(2):448-457.

Nestel et al., Specific plasma lipid classes and phospholipid fatty acids indicative of dairy food consumption associate with insulin sensitivity. Am J Clin Nutr., 2014, 99(1):46-53.

Nestel P., "Trans fatty acids: are its cardiovascular risks fully appreciated?". Clin Ther. 2014, 36(3):315-321.

Neuschwander-Tetri et al., "Farnesoid X nuclear receptor ligand obeticholic acid for non-cirrhotic, non-alcoholic steatohepatitis (FLINT): a multicentre, randomised, placebo-controlled trial". Lancet. 2015, 385(9972):956-965. 956-965.

Novgorodtseva et al., "Composition of fatty acids in plasma and erythrocytes and eicosanoids level in patients with metabolic syndrome". Lipids Health Dis. 2011, 10:82 in 5 pages.

Novgorodtseva et al., "Modification of fatty acids composition in erythrocytes lipids in arterial hypertension associated with dyslipidemia". Lipids Health Dis. 2011, 10:18 in 5 pages.

Oberley et al., "Laboratory testing for cobalamin deficiency in megaloblastic anemia". Am J Hematol. (2013) 88(6):522-524.

Ojala et al., "Expression of interleukin-18 is increased in the brains of Alzheimer's disease patients". Neurobiol Aging. 2009, 30(2):198-209.

Otogawa et al., "Erythrophagocytosis by Liver Macrophages (Kupffer Cells) Promotes Oxidative Stress, Inflammation, and Fibrosis in a Rabbit Model of Steatohepatitis: Implications for the Pathogenesis of Human Nonalcoholic Steatohepatitis". Am J Pathol. 2007, 170(3):967-980.

Özogul et al., Fatty acid profiles and fat contents of commercially important seawater and freshwater fish species of Turkey: A comparative study. Food Chem. 2007, 103:217-223.

Panee J., "Monocyte Chemoattractant Protein 1 (MCP-1) in Obesity and Diabetes", Cytokine. (2012) 60(1):1-12.

Patel et al., "Fatty acids measured in plasma and erythrocyte-membrane phospholipids and derived by food-frequency questionnaire and the risk of new-onset type 2 diabetes: a pilot study in the European Prospective Investigation into Cancer and Nutrition (EPIC)-Norfolk cohort". Am J Clin Nutri. 2010, 92(5):1214-1222.

Penckofer et al., "Oxidative stress and cardiovascular disease in type 2 diabetes: the role of antioxidants and prooxidants". J Cardiovasc Nurs. 2002, 16(2):68-85.

Pereira et al., "Dairy consumption, obesity, and the insulin resistance syndrome in young adults: the CARDIA study", JAMA. 2002, 287(16):2081-2089.

(56) References Cited

OTHER PUBLICATIONS

Perry V.H., "Contribution of systemic inflammation to chronic neurodegeneration". Acta Neuropathol. 2010, 120(3):277-286.
Perry et al., "Microglia and macrophages of the central nervous system: the contribution of microglia priming and systemic inflammation to chronic neurodegeneration". Semin Immunopathol. (2013) 35:601-612.
Pfeuffer et al., "Milk and the metabolic syndrome", Obes Rev. 2007, 8(2):109-118.
Pfeuffer et al., "Pentadecanoic and Heptadecanoic Acids: Multifaceted Odd-Chain Fatty Acids", Adv Nutr. 2016, 7:730-734.
Pietrangelo A. "Iron in NASH, chronic liver diseases and HCC: how much iron is too much?", J Hepatol. 2009, 50(2):249-251.
Popp-Snijders et al., "Dietary supplementation of omega-3 polyunsaturated fatty acids improves insulin sensitivity in non-insulin-dependent diabetes", Diabetes Res 1987, 4(3):141-147.
Profenno et al., "Meta-analysis of Alzheimer's disease risk with obesity, diabetes, and related disorders", Biol Psychiatry. 2010, 67(6):505-512.
Qin et al., "Peroxisome proliferator-activated receptor-δ induces insulin-induced gene-1 and suppresses hepatic lipogenesis in obese diabetic mice", Hepatology, 2008, 48(2):432-441.
Ramírez et al., "Absorption and distribution of dietary fatty acids from different sources". Early Hum Develop. 2001, 65(Suppl):S95-S101.
Ratziu V., "Novel pharmacotherapy options for NASH". Dig Dis Sci. 2016, 61(5):1398-1405.
Ratziu et al., "Elafibranor, an agonist of the peroxisome proliferator-activated receptor-α and -δ, induces resolution of nonalcoholic steatohepatitis without fibrosis worsening". Gastroenterology. 2016, 150(5):1147-1159.
Robinson et al., "N-3 polyunsaturated fatty acids: relationship to inflammation in healthy adults and adults exhibiting features of metabolic syndrome." Lipids. 2013, 48(4):319-332.
Ross et al., "CHF5074 reduces biomarkers of neuroinflammation in patients with mild cognitive impairment: a 12-week, double-blind, placebo-controlled study". Curr Alzheimer Res. 2013, 10(7):742-753.
Ruidavets et al., "High consumptions of grain, fish, dairy products and combinations of these are associated with a low prevalence of metabolic syndrome", J Epidemiol Community Health, 2007, 61(9):810-817.
Safadi et al., "The fatty acid-bile acid conjugate Aramchol reduces patients with nonalcoholic fatty liver disease". Clin Gastroenterol Hepatol. 2014, 12(12):2085-2091.
Salameh et al., "Insulin resistance, dyslipidemia, and apolipoprotein E interactions as mechanisms in cognitive impairment and Alzheimer's disease", Exp Biol Med (Maywood). 2016, 241(15):1676-1683.
Sanches et al., "Nonalcoholic Steatohepatitis: A Search for Factual Animal Models". Biomed Res Int. 2015, doi: [10.1155/2015/574832] in 13 pages.
Sandrou et al., "Low-fat/calorie foods: current state and perspectives", Crit Rev Food Sci Nutr. 2000, 40(5):427-447.
Sarikurkcu et al., "Screening of Possible In Vitro Neuroprotective, Skin Care, Antihyperglycemic, and Antioxidative Effects of *Anchusa undulata* L. subsp. *hybrida* (Ten.) Coutinho from Turkey and Its Fatty Acid Profile", International J Food Proper. 2015, 18(7):1491-1504.
Sarikurkcu et al., Publication date, 2019, email dated Jun. 18, 2019 in 19 pages.
Schmeda-Hirschmann et al., Anti-inflammatory activity of animal oils from the Peruvian Amazon. J Ethnopharmacol. 2014, 156:9-15.
Seki et al., "Eicosapentaenoic Acid (EPA) Attenuates the Anemia Due to Ribavirin/Interferon a Treatment in Patients with Chronic Hapatitis C", 2004, 3199 in 4 pages.
Sindhu et al., "Obesity Is a Positive Modulator of IL-6R and IL-6 Expression in the Subcutaneous Adipose Tissue: Significance for Metabolic Inflammation". PLoS One. 2015, 10(7):e0133494 in 17 pages.

Slifka KA., Comparative diet analysis of fish species commonly consumed by managed and free-ranging bottlenose dolphins (*Tursiops truncatus*). Int J Vet Med. (2013) 10:1.
Sobolesky et al., "Feeding a Modified Fish Diet to Bottlenose Dolphins Leads to an Increase in Serum Adiponectin and Sphingolipids", Front Endocrinol. 2016, 7:33 in 11 pages.
Sorrentino et al., "Liver iron excess in patients with hepatocellular carcinoma developed on non-alcoholic steato-hepatitis". J Hepatol. 2009, 50(2):351-357.
Spyridaki et al., (2016) Obesity, inflammation and cognition. Curr Opin Behav Sci. 2016, 9:169-175.
Stephenson et al., "Building a Roadmap for Developing Combination Therapies for Alzheimer's Disease", Expert Rev Neurother. 2015, 15(3):327-333.
Suresh et al., "Protective action of arachidonic acid against alloxan-induced cytotoxicity and diabetes mellitus". Prostaglandins Leukot Essent Fatty Acids, 2001, 64(1):37-52.
Swaminathan et al., "The role of iron in diabetes and its complications", Diabetes Care. 2007, 30(7):1926-1933.
Targher et al., "Elevated levels of interleukin-6 in young adults with type 1 diabetes without clinical evidence of microvascular and macrovascular complications". Diabetes Care (2001) 24(5):956-957.
Targher et al., "Risk of Cardiovascular Disease in Patients with Nonalcoholic Fatty Liver Disease", N Engl J Med., 2010, 363:1341-1350.
Tucsek et al., "Obesity in Aging Exacerbates Blood-Brain Barrier Disruption, Neuroinflammation, and Oxidative Stress in the Mouse Hippocampus: Effects on Expression of Genes Involved in Beta-Amyloid Generation and Alzheimer's Disease", J Gerontol A Biol Sci Med Sci. 2014, 69(10):1212-1226; publ. online Nov. 11, 2013.
Unnikrishnan et al., "Antiinflammatory activity of methionine, methionine sulfoxide and methionine sulfone". Agents Actions. 1990, 31(1-2):110-112.
Valenti et al., "Iron depletion by phlebotomy improves insulin resistance in patients with nonalcoholic fatty liver disease and hyperferritinemia: evidence from a case-control study". Am J Gastroenterol. 2007, 102(6):1251-1258.
Valenti et al., "[769] Iron Depletion by phlebotomy improves insulin resistance in patients with nonalcoholic fatty liver disease and hyperferritinemia: evidence from a case-control study", J Hepatol. (Apr. 2007) 46:S288-S289.
Valenti et al., "A randomized trial of iron depletion in patients with nonalcoholic fatty liver disease and hyperferritinemia". World J Gastroenterol. 2014, 20(11):3002-3010.
Van Eldik et al., The roles of inflammation and immune mechanisms in Alzheimer's disease. Alzheimers Dement (N.Y.), 2016, 2(2):99-109.
Venn-Watson et al., "Big brains and blood glucose: common ground for diabetes mellitus in humans and healthy dolphins", Comp Med., 2007, 57(4):390-395.
Venn-Watson et al., "Assessment of increased serum aminotransferases in a managed Atlantic bottlenose dolphin (*Tursiops truncatus*) population", J Wildlf Dis. 2008, 44(2):318-330.
Venn-Watson et al., "Dolphins as animal models for type 2 diabetes: sustained, post-prandial hyperglycemia and hyperinsulinemia", Gen Comp Endocrinol. 2011, 170(1):193-199.
Venn-Watson et al., Physiology of aging among healthy, older bottlenose dolphins (*Tursiops truncatus*): comparisons with aging humans. J Comp Phys B. 2011, 181(15):667-680.
Venn-Watson et al., "Hemochromatosis and fatty liver disease: building evidence for insulin resistance in bottlenose dolphins (*Tursiops truncatus*)." J Zoo Wildl Med. 2012, 43(3 Suppl):S35-S47.
Venn-Watson et al., "Blood-Based Indicators of Insulin Resistance and Metabolic Syndrome in Bottlenose Dolphins (*Tursiops truncatus*)", Front Endocrinol (Lausanne) 2013, 4:136 in 8 pages.
Venn-Watson et al., Associations of ceruloplasmin and haptoglobin with inflammation and glucose in bottlenose dolphins (*Tursiops truncatus*) J Comp Clin Path. 2014, 23(4):1031-1036.
Venn-Watson S., "Dolphins and Diabetes: Applying One Health for breakthrough discoveries". Front Endocrinol (Lausanne); 2014, 5:227 in 2 pages.

(56) References Cited

OTHER PUBLICATIONS

Venn-Watson et al., "Investigation of Fish-Based Nutrients to Protect Against Metabolic Syndrome in Bottlenose Dolphins (*Tursiops truncatus*)", presentation at International Association for Aquatic Animal Medicine (IAAAM), Gold Coast, Australia, May 2014.
Venn-Watson et al., "Adrenal Gland and Lung Lesions in Gulf of Mexico Common Bottlenose Dolphins (*Tursiops truncatus*) Found Dead following the Deepwater Horizon Oil Spill". PLoS One 2015 10(5):e0126538 in 23 pages.
Venn-Watson et al., "Evaluation of annual survival and mortality rates and longevity of bottlenose dolphins (*Tursiops truncatus*) at the United States Navy Marine Mammal Program from 2004 through 2013", J Am Vet Med. 2015, 246(8):893-898.
Venn-Watson et al., "Increased Dietary Intake of Saturated Fatty Acid Heptadecanoic Acid (C17:0) Associated with Decreasing Ferritin and Alleviated Metabolic Syndrome in Dolphins", PLoS One, 2016, 10(7):e0132117 in 17 pages.
Wang et al., "Obesity modifies the relations between serum markers of dairy fats and inflammation and oxidative stress among adolescents." Obesity (Silver Spring), 2011, 19(12):2404-2410.
Warensjö et al., "Biomarkers of milk fat and the risk of myocardial infarction in men and women: a prospective, matched case-control study." Am J Clin Nutr. (2010) 92(1):194-202.
Weiss et al., "Anemia of chronic disease." New Engl J Med. 2005, 352:1011-1023.
Wells et al., "Bottlenose dolphins as marine ecosystem sentinels: developing a health monitoring system", EcoHealth 2004, 1:246-254.
Wells et al., "Evaluation of Potential Protective Factors Against Metabolic Syndrome in Bottlenose Dolphins: Feeding and Activity Patterns of Dolphins in Sarasota Bay, Florida", Front Endocrinol (Lausanne), 2013, 4:139 in 16 pages.
Wlazlo et al., Iron metabolism is associated with adipocyte insulin resistance and plasma adiponectin. Diabetes Care, 2012, 36(2):309-315.
Wu et al., "Alterations of the Neuroinflammatory Markers IL-6 and TRAIL in Alzheimer's Disease", Dement Geriatr Cogn Dis Extra. 2015, 5(3):424-434.
Xu et al., "Molecular Recognition of Fatty Acids by Peroxisome Proliferator-Activated Receptors", Mol Cell. 1999, 3:397-403.
Yamano et al., "A long-term high-fat diet changes iron distribution in the body, increasing iron accumulation specifically in the mouse spleen.". J Nutr Sci Vitaminol. (Tokyo) 2015, 61(1):20-27.
Yin et al., "Concurrent Epstein-Barr virus associated NK/T cell lymphoma after immunosuppressive therapy for aplastic anemia: report of a case and review of literature". Int'l J Clin Exper Pathol. (2015) 8(6):7588 in 6 pages.
Zandman-Goddard et al., "Hyperferritinemia in autoimmunity". IMAJ, 2008, 10: 83-84.
Zandman-Goddard et al., "Ferritin in autoimmune diseases". Autoimmunity Rev. 2007, 6:457-463.
Zhao et al., Body iron stores and heme-iron intake in relation to type 2 diabetes: a systematic review and meta-analysis. PLoS One 2012, 7:e41641.
International Search Report and Written Opinion dated Sep. 27, 2019 for PCT/US2019/033175.
Bialek et al., "Fatty acid composition and oxidative characteristics of novel edible oils in Poland". CyTA-Journal of Food. Jan. 2, 2017;15(1): 1-8; (published online Jul. 13, 2016).
Chebib et al., "Guanidino acids act as ρ1 GABAC receptor antagonists". Neurochem Res. Apr. 23, 2009; 34(10): 1704-1711.
Crossno et al., "Rosiglitazone Attenuates Hypoxia-induced Pulmonary Arterial Remodeling". Am J Physiol Lung Cell Mol Physiol. Apr. 2007;292(4): L885-L897.
Gao et al., "In vitro evaluation of dual agonists for PPARγ/β from the flower of Edgeworthia gardneri (wall.) Meisn". J Ethnopharma . . . Mar. 13, 2015;162: 14-19.
Goncalves et al., "Fenofibrate prevents skeletal muscle loss in mice with lung cancer". PNAS. Jan. 23, 2018;115(4): E743-E752.

Greer et al., "Preparation and Bactericidal Properties of Certain Pentadecanoic, Heptadecanoic and Nonadecanoic Acids". XIX1. J Am Chem Soc. Jun. 1930;52(6): 2540-2543.
Larsen et al., "Sulfur-substituted and α-methylated fatty acids as peroxisome proliferator-activated receptor activators". Lipids. Jan. 2005;40(1): 49-57.
Meglasson et al., Antihyperglycemic action of guanidinoalkanoic acids: 3-Guanidinopropionic Acid Ameliorates Hyperglycemia in Diabetic KKA y and C57BL6J ob/ob Mice and Increases Glucose Disappearance in Rhesus Monkeys. J Pharm Exp Thera. Sep. 1, 1993;266(3): 1454-1462.
Quintanilla et al., "Role of PPARγ in the Differentiation and Function of Neurons", Hindawi Publ. Corp. 2014; Article ID 768594 in 10 pages.
Song et al., Hippocampal PPARα is a novel therapeutic target for depression and mediates the antidepressant actions of fluoxetine in mice, Br J Pharmacol. Jul. 2018;175(14): 2968-2987.
Stenmark et al., "Animal models of pulmonary arterial hypertension: the hope for etiological discovery and pharmacological cure". Am J Physiol Lung Cell Mol Physiol. Dec. 2009;297(6): L1013-L1032.
Adachi et al., "Effect of the glyceride of pentadecanoic acid on energy metabolism in hair follicles". Int J Cosmetic Sci. Jun. 1993;15(3): 125-131.
Agius et al., "The metformin mechanism on gluconeogenesis and AMPK activation: the metabolite perspective". Int J Mol Sci. May 3, 2020;21(9): 3240 in 19 pages.
Aglago et al., Association between serum phospholipid fatty acid levels and adiposity in Mexican women. J Lipid Res. Jul. 1, 2017;58(7): 1462-1470.
Ali et al., "Recent advances and limitations of mTOR inhibitors in the treatment of cancer". Cancer Cell Int. Dec. 2022;22(1): 284 in 16 pages.
Ananthakrishnan et al., Inflammatory bowel disease in the elderly is associated with worse outcomes: a national study of hospitalizations. Inflamm Bowel Dis. Feb. 1, 2009;15(2): 182-189.
Anisimov et al., "Metformin slows down aging and extends life span of female SHR mice". Cell Cycle Sep. 1, 2008;7(17): 2769-2773.
Bartzokis et al., Brain ferritin iron may influence age- and gender-related risks of neurodegeneration. Neurobiol Aging. Mar. 1, 2007;28(3): 414-423.
Barzilai et al, "Metformin as a tool to target aging". Cell Metab. Jun. 14, 2016;23(6): 1060-1065.
Baum et al., Drug utilization in the U.S.—1985: Seventh annual review. Rockville, MD: Food and Drug Administration, Center for Drugs and Biologies. Dec. 1986; TOC in 4 pages.
Beanes et al., Down-regulation of decorin, a transforming growth factor-beta modulator, is associated with scarless fetal wound healing. J Pediatr Surg. Nov. 1, 2001;36(11): 1666-1671.
Berg E.L. Phenotypic chemical biology for predicting safety and efficacy. Drug Disc Today Technol. Mar. 1, 2017;23: 53-60.
Bettcher et al., Increases in pro-inflammatory chemokine, MCP-1, are related to decreases in memory over time. Frontiers in aging neuroscience. Feb. 13, 2019; 11:25.
Bielec et al., Homologies between human and dolphin chromosomes detected by heterologous chromosome painting. Cytogen Genome Res. 1998;81(1): 18-25.
Biong et al., Intake of milk fat, reflected in adipose tissue fatty acids and risk of myocardial infarction: a case-control study. Eur J Clin Nutr. Feb. 2006;60(2): 236-244.
Bishop et al., Heptadecanoic acid is not a key mediator in the prevention of diet-induced hepatic steatosis and insulin resistance in mice. Nutrients Apr. 24, 2023;15(9): 2052 in 14 pages.
Blagosklonny M.V., Aging and immortality: Quasi-programmed senescence and its pharmacologic inhibition. Cell cycle. Sep. 15, 2006;5(18): 2087-2102.
Blagosklonny M.V., Rapamycin for longevity: opinion article. Aging Oct. 15, 2019;11(19): 8048-8067.
Blagosklonny M.V., "Cell senescence, rapamycin and hyperfunction theory of aging". Cell Cycle Jul. 18, 2022;21(14): 1456-1467.

(56) References Cited

OTHER PUBLICATIONS

Bridle et al., "Rapamycin inhibits hepatic fibrosis in rats by attenuating multiple profibrogenic pathways". Transplantation Oct. 2009;15(10): 1315-1324.
Browner et al., "The genetics of human longevity". Am J Med. Dec. 1, 2004;117(11): 851-860.
Brydges et al., Metabolomic and inflammatory signatures of symptom dimensions in major depression. Brain, Behavior, and Immunity. May 1, 2022;102: 42-52 (available Aug. 5, 2021).
Budczies et al., "Remodeling of central metabolism in invasive breast cancer compared to normal breast tissue—a GC-TOFMS based metabolomics study". BMC Genomics Dec. 2012;13(1): 334 in 11 pages.
CAS Database Accession No. 1989:205056; "Relationship between structure and anticonvulsant activities of 2-substituted 3-pyrazolidinones". Du et al., Jun. 10, 1989; 2 pages.
Chaib et al., "Cellular senescence and senolytics: the path to the clinic". Nat Med. Aug. 2022;28(8): 1556-1568.
Chaudhari et al., Increased mitochondrial fusion allows the survival of older animals in diverse C. elegans longevity pathways. Nat Commun. Aug. 3, 2017;8(1): 182 in 16 pages.
Cheng et al., "Metformin's mechanisms in attenuating hallmarks of aging and age-related disease". Aging Dis. Jul. 7, 2022;13(4): 970-986.
Coccia et al., IL-1β mediates chronic intestinal inflammation by promoting the accumulation of IL-17A secreting innate lymphoid cells and CD4+ Th17 cells. J Exp Med. Aug. 27, 2012;209(9): 1595-1609.
Cordaro et al., "2-Pentadecyl-2-Oxazoline reduces neuroinflammatory environment in the MPTP Model of Parkinson Disease". Mol Neurobiol. Dec. 2018;55(12): 9251-9266.
Crimmins E.M., "Lifespan and healthspan: past, present, and promise". The Gerontologist Dec. 1, 2015;55(6): 901-911.
Cusi et al., Metformin: A review of its metabolic effects. Diab Rev. Jan. 1, 1998;6(2): 89-131.
De Martinis et al., Allergy and aging: an old/new emerging health issue. Aging and Dis. Apr. 2017;8(2): 162-175.
De Mello et al., "Serum levels of plasmalogens and fatty acid metabolites associate with retinal microangiopathy in participants from the Finnish Diabetes Prevention Study". Nutrients Dec. 14, 2021;13(12): 4452 in.
Deng et al., Cross-talk between mitochondrial fusion and the hippo pathway in controlling cell proliferation during *Drosophila* development. Genetics Aug. 1, 2016; 203(4): 1777-1788.
DeVito et al., "Extending human lifespan and longevity: a symposium report". Ann N Y Acad Sci. Jan. 2022;1507(1): 70-83 [publ. online Sep. 8, 2021}.
Djousse et al., Serum individual nonesterified fatty acids and risk of heart failure in older adults. Cardiology Feb. 25, 2021;146(3): 351-358.
Dornan et al., Odd chain fatty acids and odd chain phenolic lipids (alkylresorcinols) are essential for diet. J Am Chem Soc. Aug. 2021;98(8): 813-824.
Dugan et al., Inflammaging as a target for healthy ageing. Age and Ageing. Feb. 1, 2023;52(2): afac328 in 15 Pages.
Ediriweera et al., "Odd-chain fatty acids as novel histone deacetylase 6 HDAC6) inhibitors". Biochimie Jul. 1, 2021 1;186: 147-156.
Ehninger et al., "Longevity, aging and rapamycin". Cell Mol Life Sci. Nov. 2014;71(22): 4325-4346.
Farage et al., Characteristics of the aging skin. Adv Wound Care. Feb. 1, 2013;2(1): 5-10.
Fonteh et al., Human cerebrospinal fluid fatty acid levels differ between supernatant fluid brain-derived nanoparticle fractions, and are altered in Alzheimer's disease. PloS One. Jun. 23, 2014;9(6): e100519 in 14 pages.
Franceschi et al.,Chronic Inflammation (Inflammaging) and Its Potential Contribution to Age-Associated Diseases. J Gerontol. Jun. 2014; 69(suppl 1): S4-S9.

Fu et al., Oleylethanolamide regulates feeding and body weight through activation of the nuclear receptor PPAR-α. Nature. Sep. 4, 2003;425(6953): 90-93.
Fu et al., Pentadecanoic acid promotes basal and insulin-stimulated glucose uptake in C2C12 myotubes. Food Nutr Res. 2021;65: 4527 in 9 pages.
Galdiero et al., Pentadecanoic acid against Candida albicans-Klebsiella pneumoniae biofilm: Towards the development of an anti-biofilm coating to prevent polymicrobial infections. Res Microbiology. Nov. 1, 2021;172(7-8): 103880 in 11 pages.
Garay R.P., "Investigational drugs and nutrients for human longevity. Recent clinical trials registered in ClinicalTrials.gov and clinicaltrialsregister.eu". Expert Opin Investig Drugs Jul. 3, 2021;30(7): 749-758.
Gibson et al., Cooperative care. The time has come. JONA: J Nurs Admin. Mar. 1, 1987;17(3): 19-21.
Giulani A., The application of principal component analysis to drug discovery and biomedical data. Drug Disc Today. Jul. 1, 2017;22(7): 1069-1076.
Gonzalez-Freire et al., "The road ahead for health and lifespan interventions". Ageing Res Rev. May 1, 2020;59:101037 in 46 pages.
Gosmanova et al., "Effect of metformin containing antidiabetic regimens on all-cause mortality in veterans with type 2 diabetes mellitus". Am J Med Sci. Sep. 1, 2008;336(3): 241-247.
Gregg et al., Trends in lifetime risk and years of life lost due to diabetes in the USA, 1985-2011: A modelling study. Lancet Diab Endocrinol. Nov. 1, 2014;2(22): 867-874.
Groarke et al., "Aging and hematopoiesis". Clin Geriatr Med. Aug. 1, 2019;35(3): 285-293.
Gunn-Moore et al., Alzheimer's disease in humans and other animals: a consequence of postreproductive life span and longevity rather than aging. Alzheimer's & Dementia. Feb. 1, 2018;14(2): 195-204.
Harrison et al., "Acarbose, 17-α-estradiol, and nordihydroguaiaretic acid extend mouse lifespan preferentially in males". Aging Cell Apr. 2014; 13(2): 273-282.
Hayaishi O., Molecular mechanisms of sleep-wake regulation: roles of prostaglandins D2 and E2. FASEB J. Aug. 1991;5(11): 2575-2581.
Hirose et al., Age-associated increases in heme oxygenase-1 and ferritin immunoreactivity in the autopsied brain. Legal Med. Mar. 1, 2003;5: S360-366.
Hori et al., "Serum sphingomyelin species profile is altered in hematologic malignancies". Clin Chim Acta Mar. 1, 2021;514: 29-33.
Huang et al., "Circulating saturated fatty acids and incident type 2 diabetes: A systematic review and meta-analysis". Nutrients May 1, 2019;11(5): 998 in 20 pages.
Hulbert A.J. "On the importance of fatty acid composition of membranes for aging". J Theor Biol. May 21, 2005;234(2): 277-288.
Imamura et al., "Fatty acid biomarkers of dairy fat consumption and incidence of type 2 diabetes: A pooled analysis of prospective cohort studies". PLoS Med. Oct. 10, 2018;15(10): e1002670 in 18 pages.
Iwakura et al., The roles of IL-17A in inflammatory immune responses and host defense against pathogens. Immun Rev. Dec. 2008;226(1): 57-79.
Jee et al., "Clinical relevance of glycerophospholipid, sphingomyelin and glutathione metabolism in the pathogenesis of pharyngolaryngeal cancer in smokers: the Korean Cancer Prevention Study—II". Metabolomics Nov. 2016;12: 164 in 12 Pages.
Jiao et al., Circulating fatty acids associated with advanced liver fibrosis and hepatocellular carcinoma in South Texas Hispanics. Cancer Epide., Biomark & Prev. Sep. 1, 2021;30(9): 1643-1651.
Jimenez-Cepeda et al., Dietary intake of fatty acids and its relationship with FEV1/FVC in patients with chronic obstructive pulmonary disease. Clin Nutr. ESPEN. Feb. 1, 2019;29: 92-96.
Jing et al., Metformin improves obesity-associated inflammation by altering macrophages polarization. Mol Cell Endocrin. Feb. 5, 2018;461: 256-264.

(56) References Cited

OTHER PUBLICATIONS

Jubie et al., "Design, synthesis and antidepressant activities of some novel fatty acid analogues". Med Chem Res. Apr. 2015;24(4): 1605-1616.
Justice et al., "Frameworks for proof-of-concept clinical trials of interventions that target fundamental aging processes". J Gerontol A Biol Sci Med Sci. Nov. 1, 2016;71(11): 1415-1423.
Justice et al., "Development of clinical trials to extend healthy lifespan". Cardiovasc Endocrinol Metab. Dec. 2018;7(4): 80-83.
Kaestner et al., "The potential of erythrocytes as cellular aging models". Cell Death Differ. Sep. 2017;24(9): 1475-1477.
Kaikkonen et al., "Associations of serum fatty acid proportions with obesity, insulin resistance, blood pressure and fatty liver: the cardiovascular risk in young Finns study". J Nutr Apr. 2021;151(4): 970-978.
Kaur et al., "Essential fatty acids as functional components of foods-a review". J Food Sci Technol. Oct. 2014;51: 2289-2303.
Khaw et al., Plasma phospholipid fatty acid concentration and incident coronary heart disease in men and women: the EPIC-Norfolk prospective study. PLoS Med. Jul. 3, 2012;9(7): e1001255 in 12 pages.
Khwaja et al., "Efficacy and Cardiovascular Safety of Alpha Glucosidase Inhibitors". Drug Safety Jul. 1, 2021;16(2): 122-128.
Kirkham T.C., Endocannabinoids in the regulation of appetite and body weight. Behav Pharmacol. Sep. 1, 2005;16(5-6): 297-313.
Kobayashi et al., New directions in cancer and aging: State of the science and recommendations to improve the quality of evidence on the intersection of aging with cancer control. Cancer. May 1, 2022;128(9): 1730-1737.
Kohnken et al., "Overview of the use of murine models in leukemia and lymphoma research", Front Oncol. Feb. 20, 2017;7:22 in 11 pages.
Kritchevsky et al., "Testing the geroscience hypothesis: early days". J Gerontol A Biol Sci Med Sci. Jan. 1, 2020;75(1): 99-101 [publ. online Dec. 13, 2019].
Kruchinina et al., "Erythrocyte membrane fatty acids as the potential biomarkers for detection of early-stage and progression of colorectal cancer". Ann Oncol. Jun. 1, 2018;29(Suppl 5): v52.
Kurotani et al., "Even- and odd-chain saturated fatty acids in serum phospholipids are differentially associated with adipokines". PLoS One May 26, 2017;12(5): e0178192 in 14 pages.
Lankinen et al., "Plasma fatty acids as predictors of glycaemia and type 2 diabetes". Diabetologia Nov. 2015;58: 2533-2544.
Lee et al., A current review of molecular mechanisms regarding osteoarthritis and pain. Gene Sep. 25, 2013;527(2): 440-447.
Li et al., Design, synthesis and antitumor activity study of a gemcitabine prodrug conjugated with a HDAC6 inhibitor. Bioorg Med Chem Lttrs. Sep. 15, 2022;72: 128881 in 6 pages.
Li et al., "Extraction, purification, and elucidation of six ginkgo homologs from Ginkgo biloba sarcotesta and evaluation of their anticancer activities". Molecules Nov. 11, 2022;27(22): 7777 in 15 pages.
Liang et al., "Biomarkers of dairy fat intake and risk of cardiovascular disease: a systematic review and meta analysis of prospective studies". Crit Rev Food Sci Nutr. May 3, 2018;58(7): 1122-1130.
Liechty K.W., Diminished interleukin-8 (IL-8) production in the fetal wound healing response. J Surg Res. Jun. 1, 1998;77(1): 80-84.
Lim et al., The global impact of hepatic fibrosis and end-stage liver disease. Clinics in Liver Dis. Nov. 1, 2008;12(4): 733-746.
Lin et al., Effects of the mTOR inhibitor Rapamycin on monocyte-secreted chemokines. BMC Immunol. Dec. 2014;15(1): 1-9.
Lin et al., Efficacy and safety of topical mechanistic target of rapamycin inhibitors for facial angiofibromas in patients with tuberous sclerosis complex: a systematic review and network meta-analysis. Biomedicines Mar. 31, 2022;10(4): 826 in 13 pages.
Lipschitz et al., The anemia of senescence. Am J Hematol. Aug. 1981;11(1): 47-54.
Longo et al., "Interventions to slow aging in humans: are we ready?" Aging Cell Aug. 2015;14(4): 497-510.

López-Ótin et al., "The Hallmarks of Aging", Cell Jun. 6, 2013;153(6):1194-1217.
Lyu et al., Association between anemia and 3-year all-cause mortality among oldest old people in longevity areas in China. Zhonghua Liuxingbingxue Zazhi. Jul. 1, 2015;36(7): 682-686.
Maeda T., Current topics on basic research for methamphetamine dependence and psychosis. J Wakayama Med. Soc., 2010, vol. 61, pp. 36-41.
Manca et al., Circulating fatty acids and endocannabinoide-related mediator profiles associated to human longevity. GeroScience. Aug. 2021;43(4): 1783-1798.
Martin-Montalvo et al., "Metformin improves healthspan and lifespan in mice". Nat Commun. Jul. 30, 2013;4(1): 2192 in 23 pages.
Matthan et al., Spillover effects of a family-based childhood weight-management intervention on parent nutrient biomarkers and cardiometabolic risk factors. Curr Dev Nutrition Feb. 2022;6(2): 152 in 41 pages.
McArtor et al., Extending multivariate distance matrix regression with an effect size measure and the asymptotic null distribution of the test statistic. Psychometrika. Dec. 2017;82: 1052-1077.
Mihalik et al., "Increased levels of plasma acylcarnitines in obesity and type 2 diabetes and identification of a marker of glucolipotoxicity". Obesity Sep. 2010;18(9): 1695-1700.
Millner et al., "Lipid players of cellular senescence". Metabolites Aug. 21, 2020;10(9): 399 in 17 pages.
Monjan et al., Incidence of chronic insomnia associated with medical and psychosocial factors: an epidemiologic study among older persons. Sleep Res. Jun. 1996;25: 108.
Moskalev et al., "Targeting aging mechanisms: pharmacological perspectives". Trends Endocrinol Metab. Apr. 1, 2022;33:266-280.
Murphy et al., The origin of human chromosome 1 and its homologs in placental mammals. Genome Res. Aug. 1, 2003;13(8): 1880-1888.
Nadon et al., "NIA interventions testing program: investigating putative aging intervention agents in a genetically heterogeneous mouse model". EBioMedicine Jul. 1, 2017;21: 3-4.
Niedernhofer et al., Molecular pathology endpoints useful for aging studies. Age Res Rev. May 1, 2017;35: 241-249.
Novelle et al., Metformin: A hopeful promise in aging research. CSH Persp Med. Mar. 1, 2016;6(3): a025932 in 13 pages.
Pamplona et al., Increased oxidation, glycoxidation, and lipoxidation of brain proteins in prion disease. Free Radical Biol Med. Oct. 15, 2008;45(8): 1159-1166.
Paolisso et al., Low insulin resistance and preserved B-cell function contribute to human longevity but are not associated with TH-INS genes. Exp Gerontol. Dec. 1, 2001; 37(1):147-156.
Patel et al., Prevalence and impact of pain among older adults in the United States: Findings from the 2011 National Health and Aging Trends Study. Pain Dec. 1, 2013;154(12): 2649-2657.
Perreault et al., PPARδ agonism for the treatment of obesity and associated disorders: Challenges and opportunities. PPAR Res. 2008;2008: Article ID125387; in 9 pages.
Perrone et al., Selective COX01 inhibition: A therapeutic target to be reconsidered. Curr Med Chem. Nov. 1, 2010;17(32): 3769-3805.
Qi et al., "High-resolution metabolomic biomarkers for lung cancer diagnosis and prognosis". Sci Rep. Jun. 3, 2021;11(1): 11805 in 10 pages.
Ricciardelli et al., Pentadecanal and pentadecanoic acid coatings reduce biofilm formation of *Staphylococcus epidermidis* on PDMS. Patho Dis. Apr. 2020;78(3): ftaa012 in 8 pages.
Roh et al., A clinical study of pentadecanoic glyceride (LHOP) on male pattern alopecia. J Korean Soc Clin Pharma Thera. Dec. 1, 1998;6(2): 199-206.
Salive et al., "Anemia and hemoglobin levels in older persons: relationship with age, gender, and health status". J Am Geriat Soc. May 1992;40(5): 489-496.
Salvatore et al., "Metformin: an old drug against old age and associated morbidities". Diab Res Clin Prac. Feb. 1, 2020;160: 108025 in 11 pages.
Santaren et al., "Serum pentadecanoic acid (15:0), a short-term marker of dairy food intake, is inversely associated with incident type 2 diabetes and its underlying disorders". Am J Clin Nutr. Dec. 1, 2014;100(6): 1532-1540.

(56) References Cited

OTHER PUBLICATIONS

Sawh et al., Dairy fat intake, plasma pentadecanoic acid, and plasma iso-heptadecanoic acid are inversely associated with liver fat in children. J Ped Gastroent Nutr. Apr. 4, 2021;72(4): e90 in 18 pages.
Schork et al., "Does modulation of an epigenetic clock define a geroprotector?" Adv Geriatr Med Res. Mar. 29, 2022;4(1): e220002 in 11 pages.
Sgnoc et al., Age-related aspects of cutaneous wound healing: a mini review. Gerontol. 2013;59(2): 159-164.
Shamburek et al., Disorders of the digestive system in the elderly. New Engl J Med. Feb. 15, 1990;322(7): 438-443.
Singh et al., MCP-1: Function, regulation and involvement in disease. Int Immunopharm. Dec. 1, 2021;101: 107598 in 9 pages.
Smedman et al., "Pentadecanoic acid in serum as a marker of intake of milk fat: relations between intake of milk fat and metabolic risk factors". Am J Clin Nutr. Jan. 1, 1999;69(1): 22-29.
Smith et al., "Changes in the gut microbiome and fermentation products concurrent with enhanced longevity in acarbose-treated mice". BMC Microbiol. Dec. 2019;19(1): 1-6.
Soboleva et al., "Fatty acids of the lipid fraction of erythrocyte membranes and intensity of lipid peroxidation in iron deficiency". Bull Exp Biol Med. Jun. 1994;117: 600-603.
Sorrenti et al., "Immunomodulatory and antiaging mechanisms of resveratrol, rapamycin, and metformin: focus on mTOR and AMPK signaling networks". Pharmaceuticals Jul. 23, 2022;15(8): 912 in 20 pages.
Soukas et al., "Metformin as anti-aging therapy: is it for everyone?" Trends Endocrinol Metab. Oct. 1, 2019;30(10): 745-755.
To et al., "Pentadecanoic acid, an odd-chain fatty acid, suppresses the stemness of MCF-7/SC human breast cancer stem-like cells through JAK2/STAT3 signaling". Nutrients Jun. 3, 2020;12(6): 1663 in 20 pages.
To et al., "Effects of combined pentadecanoic acid and tamoxifen treatment on tamoxifen resistance in MCF-7/SC breast cancer cell". Int J Mol Sci. Sep. 26, 2022;23(19): 11340 in 20 pages.
Tsoukalas et al., Application of metabolomics Part II: Focus on fatty acids and their metabolites in healthy adults. Int J Mol Med. Jan. 1, 2019;43(1): 233-242.
Vaarhorst et al., Lipid metabolism in long-lived families: the Leiden Longevity Study. Age. Jun. 2011;33(2): 219-227.
Venn-Watson et al., "Modified fish diet shifted serum metabolome and alleviated chronic anemia in bottlenose dolphins (*Tursiops truncatus*): Potential role of odd-chain saturated fatty acids". PLoS One Apr. 7, 2020;15(4): e0230769 (2020).
Venn-Watson et al., Efficacy of dietary odd-chain saturated fatty acid pentadecanoic acid parallels broad associated health benefits in humans: could it be essential?. Scientific Rep. May 18, 2020;10(1): 1-4.
Venn-Watson et al., A 25-y longitudinal dolphin cohort supports that long-lived individuals in same environment exhibit variation in aging rates. PNAS Aug. 25, 2020;117(34): 20950-20958.
Venn-Watson et al., "Broader and safer clinically-relevant activities of pentadecanoic acid compared to omega-3: evaluation of an emerging essential fatty acid across twelve primary human cell-based disease systems". PLoS One May 26, 2022;17(5): e0268778 in 17 pages.
Venn-Watson et al., Pentadecanoylcarnitine is a newly discovered endocannabinoid with pleiotropic activities relevant to supporting physical and mental health. Sci Rep. Aug. 23, 2022;12(1): 13717 in 11 pages.
Vézina et al., "Rapamycin (AY-22, 989), a new antifungal antibiotic"—Part I. J Antibio. 1975;28(10): 721-726.
Vitiello M.V., Sleep disorders and aging: understanding the causes. J Gerontol. Jul. 1, 1997;52(4): M189-M191.

Wagner et al., Combined treatment with exercise training and acarbose improves metabolic control and cardiovascular risk factor profile in subjects with mild type 2 diabetes. Diabetes Care Jul. 1, 2006;29(7): 1471-1477.
Wang et al., Peroxisome-proliferator-activated receptor δ activates fat metabolism to prevent obesity. Cell. Apr. 18, 2003;113(2): 159-170.
Warensjö et al., "Estimated intake of milk fat is negatively associated with cardiovascular risk factors and does not increase the risk of a first myocardial infarction. A prospective case-control study". Br J Nutr. Apr. 2004;91(4): 635-642.
Webster et al., "Target of rapamycin inhibitors (sirolimus and everolimus) for primary immunosuppression of kidney transplant recipients: a systemic review and meta-analysis of randomized trials". Transplantation May 15, 2006;81(9): 1234-1248.
Wolf et al., "The MalR type regulator AcrC is a transcriptional repressor of acarbose biosynthetic genes in *Actinoplanes* sp. SE50/110". BMC Genomics Dec. 2017;18(1): 1-4.
Wu et al., "Extension of life span by acarbose: is it mediated by the gut microbiota"? Aging Dis. Jul. 7, 2022;13(4): 1005-1014.
Xu et al., "Rapamycin for lymphangioleiomyomatosis: optimal timing and optimal dosage". Thorax Apr. 1, 2018;73(4): 308-310.
Xu et al., Cross-sectional associations of adipokines and abdominal fat distribution with aging in men. The Aging Male. Dec. 4, 2020;23(5): 1576-1582.
Vasto et al., Inflammatory networks in ageing, age-related diseases, and longevity. Mech Ageing and Dev. Jan. 1, 2007;128(1): 83-91.
Ye et al., A pharmacological network for lifespan extension in Caenorhabditis elegans. Aging cell. Apr. 2014;13(2): 206-215.
Yoo et al., "An overview of rapamycin: from discovery to future perspectives". J Indus Microbiol Biotech. May 1, 2017;44(4-5): 537-553.
Yoo et al., Fatty acids in non-alcoholic steatohepatitis: : Focus on pentadecanoic acid. PloS One. Dec. 15, 2017;12(12): e0189965 in 15 pages.
Yousefzadeh et al., Circulating levels of monocyte chemoattractant protein-1 as a potential measure of biological age in mice and frailty in humans. Aging cell. Apr. 2018;17(2): e12706 in 7 pages.
Zapala et al., Multivariate regression analysis of distance matrices for testing associations between gene expression patterns and related variables. Proc Nat Acad Scie. Dec. 19, 2006;103(51): 19430-19435.
Zapala et al., Statistical properties of multivariate distance matrix regression for high-dimensional data analysis. Front Genetics. Sep. 27, 2012;3: 190 in 10 pages.
Zhai et al., Anemia status and its relevant factors among elderly people aged above 80 years old in longevity areas in China. Chinese J of Prev Med. Feb. 1, 2010;44(2):115-118.
Zheng et al., Association between plasma phospholipid saturated fatty acids and metabolic markers of lipid, hepatic, inflammation and glycaemic pathways in eight European countries: a cross-sectional analysis in the EPIC-Interact study. BMC Med. Dec. 2017;15(1): 203 in 13 pages.
Zheng et al., Changes in plasma phospholipid fatty acid profiles over 13 years and correlates of change: European Prospective Investigation into Cancer and Nutrition-Norfolk Study. Am J Clin Nutr. Jun. 1, 2019;109(6): 1527-1534.
Zhu et al., Synthesis and inhibitory activities against colon cancer cell growth and proteasome of alkylresorcinols. J Agric Food Chem. Sep. 5, 2012;60(35): 8624-8631.
Zhu et al., A prospective study and longitudinal study of plasma phospholipid saturated fatty acid profile in relation to cardiometabolic markers and the risk of gestational diabetes. Am J Clin Nutr. Jun. 1, 2018;107(6): 1017-1026.
Zhuang et al., Saturated fatty acid intake is associated with total mortality in a nationwide cohort study. J Nutr. Jan. 1, 2019;149(1): 68-77.

FIGURE 9.

| Cell-based activity | Dolphin-based compounds with demonstrated anti-inflammatory activity in human cell systems | | | | | | |
|---|---|---|---|---|---|---|---|
| | 4-hydroxy-glutamate | 4-imidazole-acetate | 5-amino-valerate | Xanthurenate | Methionine sulfone | Gamma-glutamylglycine | 10-undecanoate |
| Cell-based system(s) | SAg | SAg | SAg | LPS | LPS, CASM3C | SAg. BT | LPS, SAg |
| Recapitulated diseases | Th1 inflammation (chronic inflammation & autoimmune diseases) | Th1 inflammation (chronic inflammation & autoimmune diseases) | Th1 inflammation (chronic inflammation & autoimmune diseases) | Th1 inflammation & monocyte activation (cardiovascular disease, chronic inflammation) | Th1 inflammation & monocyte activation (cardiovascular disease, chronic inflammation) | Th1 inflammation & T cell dependent B cell proliferation (allergy, asthma, autoimmunity, cancer, chronic inflammation & autoimmune diseases) | Th1 inflammation & monocyte activation (cardiovascular disease, chronic inflammation & autoimmune diseases) |
| Anti-inflammatory activity | T cell anti-proliferative | T cell anti-proliferative | T cell anti-proliferative | PGE2 lowering | PGE2 & VCAM-1 lowering | T cell proliferation & IL-17A lowering | PGE2 & CD40 lowering |
| Control compounds with similar phenotypes / mechanisms | KDM inhibitor, NSAID | IKK2 inhibitor, NSAID | KDM inhibitor, IKK2 inhibitor | IDO inhibitor, antioxidant | NSAID, iron chelating agent | KDM inhibitor, NSAID | Antifibrotic agent, NSAID |

COMPOSITIONS AND METHODS FOR DIAGNOSIS AND TREATMENT OF CONDITIONS RELATED TO THE QUALITY OF AGING AND LONGEVITY

INCORPORATION BY REFERENCE TO RELATED APPLICATION

Any and all priority claims identified in the Application Data Sheet, or any correction thereto, are hereby incorporated by reference under 37 CFR 1.57. This application is a continuation of PCT International Application No. PCT/US2019/033175, which has an International Filing Date of May 20, 2019, which designates the United States and which was published in English on Nov. 28, 2019, which claims the benefit of U.S. Provisional Application No. 62/675,621, filed May 23, 2018, U.S. Provisional Application No. 62/751,201, filed Oct. 26, 2018, and U.S. Provisional Application No. 62/838,234, filed Apr. 24, 2019. Each of the aforementioned applications is incorporated by reference herein in its entirety, and each is hereby expressly made a part of this specification.

STATEMENT REGARDING FEDERALLY SPONSORED R&D

The United States Government has certain rights in this invention, under CRADA Number NCRADA-SSCPA-CIFIC-17-261.

FIELD OF THE INVENTION

Compositions including metabolites that are small molecules, and salts and derivatives thereof, and methods for treatment or prophylaxis of conditions related to the quality of aging are provided, including compositions and methods for treating conditions that negatively impact longevity and the quality of aging, including inflammation, anemia, hyperglycemia, dyslipidemia, hyperinsulinemia, liver disease, iron overload, impaired skin integrity, wound healing, scarring, pain, allergies, sleep disorders and problems, and gastrointestinal disorders and problems.

FIELD OF THE INVENTION

Compositions including metabolites that are small molecules, and salts and derivatives thereof, and methods for treatment or prophylaxis of conditions related to the quality of aging are provided, including compositions and methods for treating conditions that negatively impact longevity and the quality of aging, including inflammation, anemia, hyperglycemia, dyslipidemia, hyperinsulinemia, liver disease, iron overload, impaired skin integrity, wound healing, scarring, pain, allergies, sleep disorders and problems, and gastrointestinal disorders and problems.

BACKGROUND OF THE INVENTION

Aging increases the risk of health conditions that can decrease quality of life and longevity. As people age, they have a higher risk of developing a suite of conditions, including inflammation, anemia, hyperglycemia, dyslipidemia, hyperinsulinemia, liver disease, iron overload, impaired skin integrity, wound healing, scarring, pain, allergies, sleep disorders and problems, and gastrointestinal disorders and problems. These conditions are contributing factors to a reduced quality of life, and as such, treatments of these conditions have been proposed as a means to improve longevity and quality of life.

SUMMARY OF THE INVENTION

Compositions and methods for treatment or prophylaxis of conditions with aging that impact quality of life or longevity are provided. These compositions comprise one or more small molecule biochemicals, derivatives of these biochemicals, or salts thereof, which may be administered in combination with other medicaments or as part of various treatment regimens as described herein. The provided compositions are effective for modulating markers of aging-associated conditions that impact quality of life or longevity. Methods are provided for administering the compositions.

The compositions are suitable for the treatment, amelioration, or prevention of conditions including but not limited to Th1-type inflammation, Th2-type inflammation, T-cell dependent B cell proliferation, allergy, asthma, atherosclerosis, autoimmunity, chronic inflammation, chronic obstructive pulmonary disease (COPD), Crohn's disease, cutaneous responses to tissue damage, fibrosis, hematological oncology, metabolic diseases, organ transplantation, psoriasis, pulmonary fibrosis, pulmonary responses to respiratory infections, restenosis, rheumatoid arthritis, sarcoidosis, stromal biology in tumors, systemic lupus erythematosus (SLE), ulcerative colitis, and vascular inflammation.

Diseases that are driven or exacerbated by the following factors may be attenuated or treated by compositions as disclosed herein: alpha smooth muscle actin (αSMA), CD40, CD69, collagen I, collagen III, decorin, e-selectin, eotaxin 3 (CCL26), fibroblast proliferation, human leukocyte antigen-DR isotype (HLA-DR), immunoglobulin G, interferon gamma-induced protein 10 (IP-10/CXCL10), interferon-inducible T cell alpha chemoattractant (I-TAC/CXCL11), interleukin (IL)-1, IL-1α, IL-2, IL-6, IL-8 (CXCL8), IL-10, IL-17A, IL-17F, keratin 8/81, macrophage colony-stimulating factor (M-CSF), matrix metalloproteinase (MMP)-1, MMP-9, monocyte chemoattractant protein 1 (MCP-1), monokine induced by gamma interferon (MIG/CXCL9), plasminogen activation inhibitor 1 (PAI-1), prostaglandin E2 (PGE2), serum amyloid A, T or B cell proliferation, tissue plasminogen activator (tPA), tumor necrosis factor alpha (TNFα), vascular cell adhesion molecule (VCAM-1), vascular endothelial growth factor 2 (VEGFR2).

Accordingly, in a generally applicable first aspect (i.e., independently combinable with any of the aspects or embodiments identified herein), a pharmaceutical composition is provided comprising: one or more small molecule metabolites, or pharmaceutically acceptable salts thereof, wherein the one or more small molecule metabolites are selected from the group consisting of one or more small molecule metabolites; and a pharmaceutically acceptable carrier.

In an embodiment of the first aspect (i.e., independently combinable with any of the aspects or embodiments identified herein), the one or more small molecules is a metabolite described herein.

In an embodiment of the first aspect (i.e., independently combinable with any of the aspects or embodiments identified herein), the composition is in a unit dosage form.

In an embodiment of the first aspect (i.e., independently combinable with any of the aspects or embodiments identified herein), the pharmaceutical composition is configured for administration of from 2.5 mg to 50 mg, per 1 kg of body weight, of the one or more small molecule metabolites or pharmaceutically acceptable salts thereof to a patient.

In an embodiment of the first aspect (i.e., independently combinable with any of the aspects or embodiments identified herein), the pharmaceutical composition is configured for administration once per day.

In an embodiment of the first aspect (i.e., independently combinable with any of the aspects or embodiments identified herein), the pharmaceutical composition comprises from 0.01 mg to 10000 mg of the one or more small molecule metabolites or pharmaceutically acceptable salts thereof.

In a generally applicable second aspect (i.e., independently combinable with any of the aspects or embodiments identified herein), use is provided of a pharmaceutical composition of the first aspect or any embodiment thereof, in the manufacture of a medicament for treatment or prophylaxis of conditions related to quality of life or longevity, wherein the conditions related to quality of life or longevity are selected from the group consisting of inflammation, anemia, hyperglycemia, dyslipidemia, hyperinsulinemia, liver disease, iron overload, impaired skin integrity, wound healing, scarring, pain, allergies, sleep disorders and problems, and gastrointestinal disorders and problems.

In an embodiment of the second aspect (i.e., independently combinable with any of the aspects or embodiments identified herein), the use is in the manufacture of a medicament for treatment or prophylaxis of conditions related to quality of life or longevity.

In an embodiment of the second aspect (i.e., independently combinable with any of the aspects or embodiments identified herein), the pharmaceutical composition is configured to modulate a marker of aging-associated conditions related to quality of life or longevity or a symptom of conditions related to quality of life or longevity.

In an embodiment of the second aspect (i.e., independently combinable with any of the aspects or embodiments identified herein), the marker of conditions related to quality of life or longevity is selected from the group consisting of serum or plasma small molecule metabolite concentration, red blood cell indices (i.e. hemoglobin, red blood cells), serum or plasma cholesterol, triglycerides, insulin, glucose, gamma-glutamyl transpeptidase, ferritin, or iron.

In an embodiment of the second aspect (i.e., independently combinable with any of the aspects or embodiments identified herein), the pharmaceutical composition is configured to increase a serum, red blood cell, or tissue concentration of the one or more small molecule metabolites to between 0.2 µM and 20 µM.

In a generally applicable third aspect (i.e., independently combinable with any of the aspects or embodiments identified herein), a method of treatment or prophylaxis of conditions associated with quality of life or longevity, including inflammation, anemia, hyperglycemia, dyslipidemia, hyperinsulinemia, liver disease, iron overload, impaired skin integrity, wound healing, scarring, pain, allergies, sleep disorders and problems, and gastrointestinal disorders and problems, and other related conditions, comprising: administering to a patient in need thereof, an effective amount of one or more small molecule metabolites, or pharmaceutically acceptable salts thereof, wherein the one or more small molecule metabolites are selected from the group described herein.

In an embodiment of the third aspect (i.e., independently combinable with any of the aspects or embodiments identified herein), the one or more small molecule metabolites or pharmaceutically acceptable salts thereof is provided as a pharmaceutical composition in a unit dosage form comprising the one or more small molecule metabolites or pharmaceutically acceptable salts thereof and a pharmaceutically acceptable carrier.

In an embodiment of the third aspect (i.e., independently combinable with any of the aspects or embodiments identified herein), the unit dosage form comprises from 0.01 mg to 10000 mg of the one or more small molecule metabolites or pharmaceutically acceptable salts thereof.

In an embodiment of the third aspect (i.e., independently combinable with any of the aspects or embodiments identified herein), the one or more small molecule metabolites described herein.

In an embodiment of the third aspect (i.e., independently combinable with any of the aspects or embodiments identified herein), the pharmaceutical composition comprises a plurality of different small molecule metabolites described herein.

In an embodiment of the third aspect (i.e., independently combinable with any of the aspects or embodiments identified herein), from 2.5 mg to 50 mg of the one or more small molecule metabolites or pharmaceutically acceptable salts thereof is administered to the patient, per 1 kg of body weight, per day.

In an embodiment of the third aspect (i.e., independently combinable with any of the aspects or embodiments identified herein), the one or more small molecule metabolites or pharmaceutically acceptable salts thereof is administered to the patient once per day.

In an embodiment of the third aspect (i.e., independently combinable with any of the aspects or embodiments identified herein), a serum, tissue, or a red blood cell membrane concentration of the one or more small molecule metabolites is increased 1.25 to 6 times above the patient's baseline levels to achieve concentrations between 0.5 µM and 20 µM.

In a generally applicable fourth aspect (i.e., independently combinable with any of the aspects or embodiments identified herein), a composition substantially as described herein is provided.

In a generally applicable fifth aspect (i.e., independently combinable with any of the aspects or embodiments identified herein), a composition substantially as described herein is provided.

In a generally applicable sixth aspect (i.e., independently combinable with any of the aspects or embodiments identified herein), a use substantially as described herein is provided.

DESCRIPTION OF THE DRAWINGS

FIG. 9 is a table providing information on dolphin-based compounds with demonstrated anti-inflammatory activity in human cell systems.

DETAILED DESCRIPTION

Figure 1:
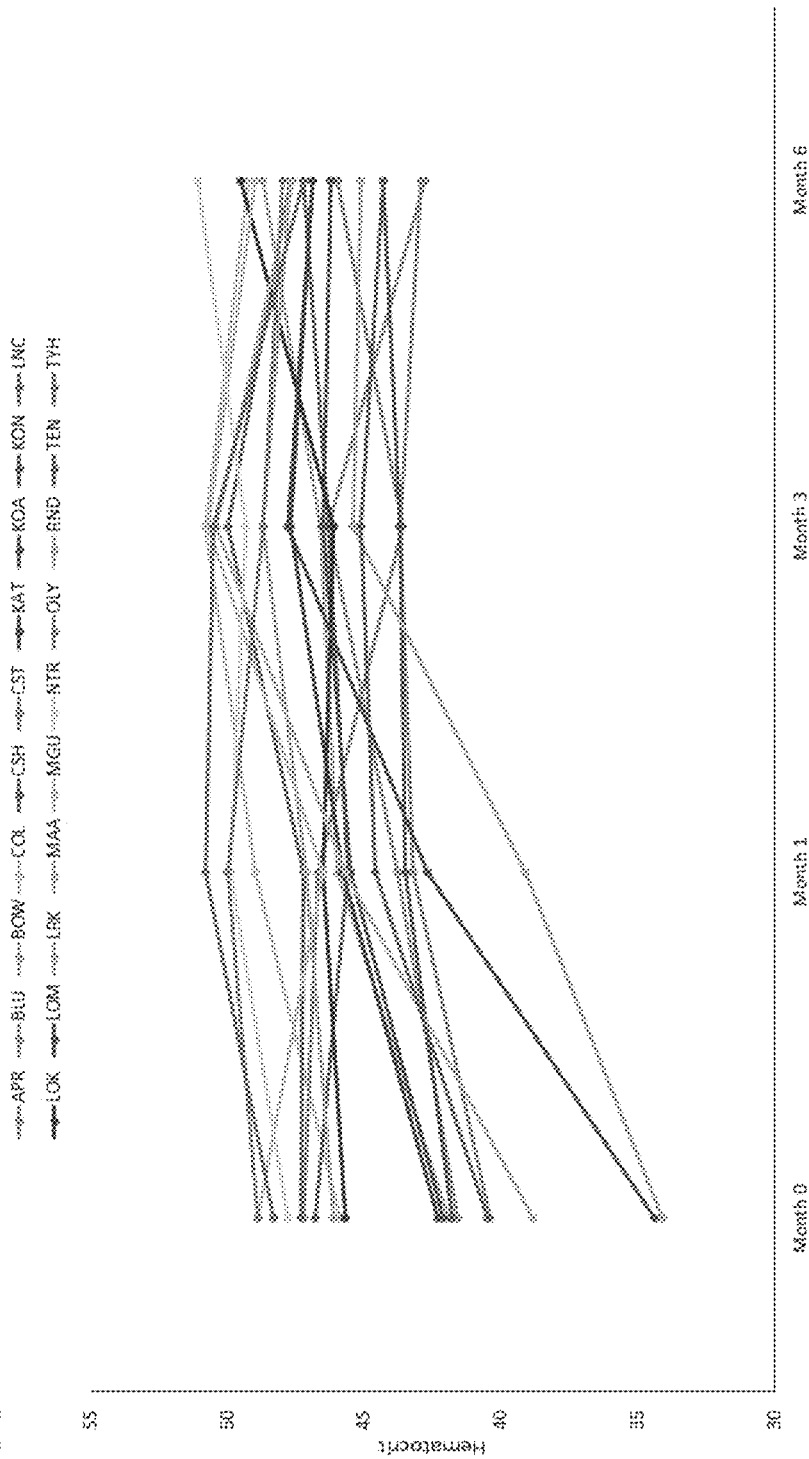
FIG. 1. provides data on improving hematocrit among individual dolphins while on the modified fish diet.

Compositions including one or more small molecule metabolites, and associated methods for treatment of conditions related to aging, including inflammation, anemia, hyperglycemia, dyslipidemia, hyperinsulinemia, liver disease, iron overload, impaired skin integrity, wound healing, scarring, pain, allergies, sleep disorders and problems, and gastrointestinal disorders and problems, and other related conditions, are provided.

Aging is associated with chronic, low-grade inflammation characterized by increased circulating levels of proinflammatory cytokines, neutrophils, and progressively activated macrophages. This pro-inflammatory state is a significant risk factor for both morbidity and mortality in the elderly people (Franceschi C, Campisi J (2014) Chronic inflammation (inflammaging) and its potential contribution to age-associated diseases. J Gerontol Ser A 69:S4-S9). People who live at least 100 years are less likely to have developed a proinflammatory state with age, further supporting that chronic, low-grade inflammation impairs quality and duration of life (Vasto S, Candore G, Balistreri M, Colonna-Romano G, Grimaldi M P, Listi F et al. (2007) Inflammatory networks in ageing, age-related diseases, and longevity. Mech Ageing and Dev 128:83-91). As such, interventions to reduce inflammation of aging have been proposed to concurrently treat multiple aging-associated diseases, resulting in improved quality of life and expanded longevity.

As people age, the prevalence of anemia can increase dramatically. Comparisons of populations aged 40, 60, 80, 90 and 100 (total n=1,980) had the following prevalence of anemia: 16.1%, 19.1%, 41.1%, 46.2%, and 57.1% (Zhai Y, Yin Z X, Xu J W, Liu Y Z, Shi X M (2010) Anemia status and its relevant factors among elderly people aged above 80 years old in longevity areas in China. Chinese J of Prev Med 44:115-118). The presence of anemia and low hemoglobin concentration increased the 3-year mortality risk by 25% and decreased longevity among older people (Lyu Y, Yin Z, Luo J, Shi X, Zeng Y (2015) Zhonghua Liuxingbingxue Zazhi 36:682-686). Means to prevent and treat anemia of aging are expected to improve quality of life and expand longevity.

Elevated cholesterol with aging can negatively impact quality of life or longevity. (Kriesberg R A and Kasim S (1987) Cholesterol metabolism and aging, Am J Med 82:54-60). Elevated cholesterol, especially elevated low-density lipoprotein (LDL) cholesterol, have been identified as underlying causes of or contributors to cardiovascular disease, including atherosclerosis, which also increase in prevalence with age. Lower cholesterol levels, especially for people under 50 years old, have been associated with improved longevity (Anderson K M, Castelli W P, Levy D (1987) Cholesterol and mortality: 30 years of follow-up from the Framingham Study JAMA 257:2176-2180). Similarly, triglyceride levels can be major predicting factors for human longevity, with lower triglyceride levels present in long-lived families compared to controls (Vaarhorst A A M, Beekman M, Suchiman E H D, van Heemst D V, Houwing-Duistermaat J J, Westerndorp R G et al (2010) Lipid metabolism in long-lived families: the Leiden Longevity Study. AGE 33:219-227). Preventing and treating dyslipidemia have been highlighted as important to improve quality of life and expand longevity.

Prediabetic and diabetic conditions, including hyperglycemia and insulin resistance, result in impaired quality of life and longevity. From 1999 to 2011, the average number of years lost from diabetes has increased by 46% in men and 44% in women (Gregg E W, Zhuo X, Cheng Y J, Albright A L, Narayan K M V, Thompson T J (2014) Trends in lifetime risk and years of life lost due to diabetes in the USA, 1985-2011: A modelling study. Lancet Diab Endocrinol 2:867-874). Insulin resistance increases with advanced age, and people who live over one hundred years have lower insulin resistance compared to those who were younger (Paolisso G, Barbieri M, Rizzo M R, Carella C, Rotondi M, Bonafe M et al (2001) Low insulin resistance and preserved β-cell function contribute to human longevity but are not associated with TH-INS genes. Exp Gerontol 37:147-156). Treatments long used to treat type 2 diabetes, including metformin, have been demonstrated to expand longevity (Novelle M G, Ali A, Dieguez C, Bernier M, de Cabo R (2016) Metformin: A hopeful promise in aging research. CSH Perspectives 6:a025932), and there is an active effort to discover other compounds that may help treat hyperglycemia and insulin resistance and expand longevity.

The prevalence of chronic liver disease and accompanying cirrhosis and hepatocellular carcinoma have been increasing at an alarming rate, especially in developed countries. This increase is due primarily to nonalcoholic fatty liver disease (NAFLD) associated with the global rise in obesity and metabolic syndrome (including elevated glucose, dyslipidemia, and insulin resistance). Chronic liver disease contributes to morbidity and mortality, and by aiming to decrease liver failure, transplants, and cancer, therapeutics for liver disease can improve quality of life and expand longevity (Lim Y S, Kim W R (2008) The global impact of hepatic fibrosis and end-stage liver disease. Clinics in Liver Dis 12:733-746).

Iron overload and hyperferritinemia with aging can negatively impact quality of life or longevity. Iron accumulates with age in tissues, including the brain (Hirose W, Ikematsu K, and Tsuda R (2003) Age-associated increases in heme oxygenase-1 and ferritin immunoreactivity in the autopsied brain. Legal Med 5:S360-366). Because iron induces oxidative damage to tissues, resulting in age-related diseases, such as Alzheimer's disease, compounds that reduce iron overload and hyperferritinemia have been proposed as therapeutic targets for aging-associated diseases (Bartzokis G, Tishler T A, Lu P H, Villablanca P, Altshuler L L, Carter M et al. (2007) Brain ferritin iron may influence age- and gender-related risks of neurodegeneration. Neurobiol Aging 28:414-423).

Aging skin and poor wound healing can negatively impact quality of life. Aging skin has changes to structure and function that impairs its integrity and ability to heal (Farage M A, Miller K W, Elsner P, Maibach H I (2013) Characteristics of the aging skin. Adv Wound Care 2: doi: 10.1089).

Compounds that prevent or correct intrinsic changes with age that influence skin integrity and repair can aid in improving the quality of life.

With respect to aging and pain, over half of people over 65 years old report to have bothersome pain, most of which have pain in multiple sites and have at least two chronic medical conditions such as arthritis, cardiometabolic diseases, and obesity (Patel K V et al. (2013) Prevalence and impact of pain among older adults in the United States: Findings from the 2011 National Health and Aging Trends Study. Pain 154:2649-2657). As such, anti-inflammatory agents, analgesics, and compounds that attenuate cardiometabolic diseases may aid in alleviating pain, including pain associated with aging. As an example, compounds that reduce prostaglandin E2 (PGE2) can aid in reducing inflammation, pain, and fever, including pain caused by osteoarthritis (Lee A S et al. (2013) A current review of molecular mechanisms regarding osteoarthritis and pain. Gene 527: 440-447). Other compounds that reduce inflammation associated with autoimmune diseases, such as rheumatoid arthritis, can attenuate joint inflammation and pain. As an example, interleukin-17A (IL-17a) is an important contributor to autoimmune diseases, including multiple sclerosis and rheumatoid arthritis, and a compound that lowers IL-17A may help to alleviate pain from rheumatoid arthritis (Iwakura Y et al. (2008) The roles of IL-17A inflammatory immune responses and host defense against pathogens. Immunol Rev 226:). Further, compounds that reduce chronic systemic inflammation associated with aging and cardiometabolic diseases may attenuate these diseases and their associated pain.

With respect to aging and allergies, allergies are one of the fastest growing health problems in people aged over 15 years, and 5% to 10% of allergies are affecting elderly people (Martinis M D et al. (2017) Allergy and aging: an old/new emerging health issue. Aging and Dis 8:162-175). Elderly can be at higher risk of allergies due to physiological changes with aging, concurrent diseases, polydrug therapy, and compromised systems, including the dermal, gastrointestinal, and respiratory systems. Interleukin-17A (IL-17a) is an important contributor to allergic responses, including systemic and dermal hypersensitivities and allergic airway inflammation (Iwakura Y et al. (2008) The roles of IL-17A inflammatory immune responses and host defense against pathogens. Immunol Rev 226). As such, compounds that reduce allergy responses, including reduction of IL-17A, can improve the quality of life for people, including the elderly.

With respect to aging and sleep disorders, sleep problems have been reported to affect up to 40% of the elderly population (Vitiello M V (1997) Sleep disorders and aging: understanding the causes. J Gerontol 52A:M189-M191). This high prevalence is attributed, in part, to physiological changes with aging, as well as the presence of chronic disease. Control of chronic conditions, such as pain, have been demonstrated to improve the quality of sleep and resolve insomnia (Monjan A and Foley D (1996) Incidence of chronic insomnia associated with medical and psychosocial factors: an epidemiologic study among older persons. Sleep Res 25:108). Despite growing concern over the use of benzodiazapines and other sedatives, especially among the elderly, people over 60 years old are more likely to receive sedative prescriptions compare to people aged 40 to 59 (Baum C et al. (1986) Drug utilization in the U.S.—1985: Seventh annual review. Rockville, MD: Food and Drug Administration, Center for Drugs and Biologies). As such, use of natural compounds that may help alleviate underlying medical conditions impacting sleep can be used as a first line means of improving the quality of sleep and life. As a potential alternative to sedatives, PGE2 inhibitors, which can be used to reduce inflammation, pain and fevers, may also aid in stemming PGE2's role in stimulating the wake centers near the posterior hypothalamus (Hayaishi O (1991) Molecular mechanisms of sleep-wake regulation: roles of prostaglandins D2 and E2. FASEB J 5:2575-2581).

With respect to aging and gastrointestinal and/or digestive disorders, aging impacts normal digestion, resulting in disorders associated with sensation, inflammation, poor swallowing, imbalanced microbiota, malabsorption, and malnutrition (Shamburek R D and Farrar J T (1990) Disorders of the digestive system in the elderly. New Engl J Med 322: 438-443). People older than 65 years represent 25% of all inflammatory bowel disease hospitalizations, and older age was a significant risk factor for increased mortality and more severe gastrointestinal disease compared to younger patients (Ananthakrishnan A N et al. (2009) Inflammatory bowel disease in the elderly is associated with worse outcomes: a national study of hospitalizations. Inflamm Bowel Dis 15: 182-289). Compounds that lower gastrointestinal inflammation, restore a balanced microbiota and/or improve proper absorption of nutrients may aid in alleviating digestive disorders. Interleukin-17A (IL-17A) is a contributor to chronic intestinal inflammation, and lowering IL-17A secretion may aid in alleviating digestive disorders (Coccia M et al. (2012) IL-1β mediates chronic intestinal inflammation by promoting the accumulation of IL-17A secreting innate lymphoid cells and CD4+ Th17 cells. J Exp Med 209:1595).

With respect to aging and skin conditions and/or wound healing, advanced age can impair wound healing (Sgnoc R and Gruber J (2013) Age-related aspects of cutaneous wound healing: a mini review. Gerontol 59:159-164). This impairment can be due to chronic inflammatory conditions present with age, including increases in cytokines, such as IL-6, and chemokines, such as CXCL8 (also called interleukin 8 (IL-8)), which is elevated in psoriasis. There are some differences present in fetal and elderly wound healing, however, that may be beneficial. As an example, fetal and elderly wounds heal with no to little scarring, respectively. This scarless repair may be due to lower levels of decorin and IL-8, an extracellular matrix proteoglycan and chemokine, respectively, observed in fetal tissue (Beanes S R et al. (2001) Down-regulation of decorin, a transforming growth factor-beta modulator, is associated with scarless fetal wound healing. J Pediatr Surg 36:1666-71; Liechty K W (1997) Diminished interleukin-8 (IL-8) production in the fetal wound healing response. J Surg Res 77:80-84). As such, lower levels of IL-6, IL-8, and decorin may help stem inflammation associated with chronic, non-healing wounds and enable this healing to occur with minimal scarring.

It is an object of certain of the embodiments to provide a method for detecting protective factors for and risk factors against conditions provided herein, including but not limited to inflammation, anemia, hyperglycemia, dyslipidemia, hyperinsulinemia, liver disease, iron overload, impaired skin integrity, wound healing, scarring, pain, allergies, sleep disorders and problems, and gastrointestinal disorders and problems, and other related conditions in mammal subjects, such as companion animals and humans. An object of certain of the embodiments is to provide a method for treating conditions including but not limited to aging-associated conditions that impact quality of life or longevity in mammal subjects, such as companion animals and humans. An object of certain of the embodiments is to provide a method for detecting conditions including but not limited to aging-associated conditions that impact quality of life or longevity in mammal subjects, such as companion animals and humans. It is an object of certain of the embodiments to provide a method for increasing the serum, plasma, or erythrocyte membrane level of one or more small molecule metabolites or small molecule metabolite derivatives, including but not limited to biochemicals listed in Table 1, for example, an amino acid, such as 2-methylserine, and/or certain lipids, such as 10-undecanoate, in mammal subjects, such as companion animals and humans. An object of certain of the embodiments is to provide a small molecule metabolite supplement or prescription therapeutic for treating or preventing conditions including but not limited to those associated with aging and conditions that impact quality of life or longevity. An object of certain of the embodiments is to provide a method for detecting and/or treating aging-associated conditions that impact quality of life or longevity in mammal subjects, such as companion animals and humans, that is easy to accomplish in a cost-effective manner.

An object of certain of the embodiments is to employ the compositions of the embodiments in the prophylaxis, amelioration, and/or treatment of selected diseases and conditions. These diseases and conditions include but are not limited to oral indications, e.g., cavities (tooth decay); gum disease (gingivitis); periodontitis; sensitive teeth; oral cancer; burning mouth syndrome; ulcers, sores, or tender areas in the mouth; bleeding or swollen gums after brushing or flossing; chronic bad breath; sensitivity to hot and cold temperatures or beverages; pain or toothache; loose teeth; receding gums; pain with chewing or biting; swelling of the face and cheek; clicking of the jaw; frequent dry mouth; and stomatitis. These diseases and conditions include but are not limited to skin conditions, e.g., acne, cold sore, blister, hives, actinic keratosis, rosacea, carbuncle, exzcema, psoriasis, cellulitis, measles, basal cell carsinoma, squamous cell carcinoma, melanoma, lupus, contact dermatitis, vitiligo, wart, chickenpox, seborrheic eczema, keratosis pilaris, ringworm, melasma, impetigo, diaper rash, rashes from bacterial or fungal infections, rashes from allergic reactions, fifth disease, and vasculitis. These diseases and conditions include but are not limited to pain, e.g., chronic pain, nerve pain, psychogenic pain, musculoskeletal pain, chronic muscle pain, abdominal pain, joint pain, central pain syndrome, complex regional pain syndrome, diabetes related nerve pain (neuropathy), shingles pain (postherpetic neuralgia), and trigeminal neuralgia. These diseases and conditions include but are not limited to allergies, e.g., food allergies, seasonal allergies (e.g., hay fever, pollen), allergies to animal products (e.g., pet dander, dust mites, cockroaches), drugs such as penicillin and sulfa, foods (e.g., wheat, nuts, milk, shellfish, egg, legumes), insect stings (e.g., bees, wasps, mosquitoes), mold, plants (e.g., pollens from grass, weeds, trees; resins from plants such as poison ivy and poison oak), miscellaneous allergies (e.g., latex, nickel), contact dermatitis, rashes, eczema, sore throat, hives, swollen eyes, itching, burning, itchy eyes, watery eyes, runny nose, coughing, asthma, and airway inflammation. These diseases and conditions include but are not limited to sleep conditions, e.g., obstructive sleep apnea, central sleep apnea, insomnia, hypersomnia (daytime sleepiness), parasomnias, REM sleep behavior disorder, circadian rhythm sleep disorders, non-24-hour sleep-wake disorder, periodic limb movement disorder, shift work sleep disorder, and narcolepsy. These diseases and conditions include but are not limited to digestive and/or gastrointestinal conditions or disorders, e.g., diarrhea, constipation, acid reflux, heartburn, vomiting, gastroesophageal reflux disease, gallstones, celiac disease, Crohn's disease, ulcerative colitis, irritable bowel syndrome, hemorrhoids, diverticulitis, diverticulosis, anal fissure, peptic ulcers, gastroparesis, and nausea.

An object of certain of the embodiments is to provide a method for modulating markers of aging-associated conditions that impact quality of life or longevity in mammal subjects, such as companion animals and humans. An object of certain of the embodiments is to provide a method for detecting aging-associated conditions that impact quality of life or longevity in mammal subjects, such as companion animals and humans. An object of certain of the embodiments is to provide a method for treatment of aging-associated conditions that impact quality of life or longevity in mammal subjects, such as companion animals and humans. An object of certain of the embodiments is to provide a method for prophylaxis of aging-associated conditions that impact quality of life or longevity in mammal subjects, such as companion animals and humans. An object of certain of the embodiments is to provide a method for prophylaxis of a condition provided herein including aging-associated conditions that impact quality of life or longevity, including inflammation, anemia, hyperglycemia, dyslipidemia, hyperinsulinemia, liver disease, iron overload, impaired skin integrity, wound healing, scarring, pain, allergies, sleep disorders and problems, and gastrointestinal disorders and problems, and other related conditions, in mammal subjects, such as companion animals and humans.

An object of certain of the embodiments is to provide a method for increasing a small molecule metabolite in the sera, plasma, or erythrocyte membranes of mammal subjects, such as companion animals and humans. An object of certain of the embodiments is to provide a method for detecting or treating aging-associated conditions that impact quality of life or longevity in mammal subjects, such as companion animals and humans. An object of certain of the embodiments is to provide a small molecule metabolite substantially free from other small molecule metabolites in mammal subjects, such as companion animals and humans.

It is an object of certain of the embodiments is to provide a method for detecting and treating aging-associated conditions that impact quality of life or longevity in mammal subjects, such as companion animals and humans. An object of certain of the embodiments is to provide a small molecule metabolite, such as a biochemical listed in Table 1, for treating aging-associated conditions that impact quality of life or longevity in mammal subjects, such as companion animals and humans. An object of certain of the embodiments is to provide a method for prophylaxis of aging-associated conditions that impact quality of life or longevity in mammal subjects, such as companion animals and humans. An object of certain of the embodiments is to provide a method for detecting or treating aging-associated conditions that impact quality of life or longevity in mammal subjects, such as companion animals and humans. An object of certain of the embodiments is to provide a small molecule metabolite as described herein to supplement for treating conditions that impact quality of life or longevity in mammal subjects, such as companion animals and humans.

An object of certain of the embodiments is to provide a bioavailable form of small molecule metabolites to mammal subjects, such as companion animals and humans. An object of certain of the embodiments is to provide one or more small molecule metabolites described herein with one or more other small molecule biochemicals described herein to mammal subjects, such as companion animals and humans. An object of certain embodiments is to provide a method for increasing small molecule biochemicals described herein in the sera of mammal subjects, such as companion animals and humans. An object of certain of the embodiments is to provide a method for altering concentrations of a variety of small molecule metabolites as described herein in the sera, plasma, or erythrocyte membranes of mammal subjects, such as companion animals and humans.

Compositions including one or more of certain small molecule metabolites from contained herein, and associated methods for treatment of inflammation are provided. Compositions including one or more bioavailable metabolites contained herein are provided.

Compositions including one or more of certain small molecule metabolites from Table 1, and associated methods for treatment of anemia are provided. Compositions including one or more bioavailable metabolites contained herein are provided.

Compositions including one or more of certain small molecule metabolites from Table 1, and associated methods for treatment of hyperglycemia are provided. Compositions including one or more bioavailable metabolites contained herein are provided.

Compositions including one or more of certain small molecule metabolites from Table 1, and associated methods for treatment of dyslipidemia are provided. Compositions including one or more bioavailable metabolites contained herein are provided.

Compositions including one or more of certain small molecule metabolites contained herein, and associated methods for treatment of hyperinsulinemia are provided. Compositions including one or more bioavailable metabolites contained herein are provided.

Compositions including one or more of certain small molecule metabolites contained herein, and associated methods for treatment of liver disease are provided. Compositions including one or more bioavailable metabolites contained herein are provided.

Compositions including one or more of certain small molecule metabolites contained herein, and associated methods for treatment of iron overload are provided. Compositions including one or more bioavailable metabolites contained herein are provided.

Compositions including one or more of certain small molecule metabolites contained herein, and associated methods for treatment of impaired skin integrity, wound healing, scarring, pain, allergies, sleep disorders and problems, and gastrointestinal disorders and problems are provided. Compositions including one or more bioavailable metabolites contained herein are provided.

One or more than one of the aforementioned objects is provided by or achieved by the various compositions, methods, and uses as described herein.

Definitions

The term "alcohol" as used herein is a broad term, and is to be given its ordinary and customary meaning to a person of ordinary skill in the art (and is not to be limited to a special or customized meaning), and refers without limitation to any compound as described herein incorporating one or more hydroxy groups, or being substituted by or functionalized to include one or more hydroxy groups.

The term "short-chain fatty acid" as used herein is a broad term, and is to be given its ordinary and customary meaning to a person of ordinary skill in the art (and is not to be limited to a special or customized meaning), and refers without limitation to a fatty acid with 2-6 carbon atoms The term "medium-chain fatty acid" as used herein is a broad term, and is to be given its ordinary and customary meaning to a person of ordinary skill in the art (and is not to be limited to a special or customized meaning), and refers without limitation to a fatty acid with 7-12 carbon atoms.

The term "long-chain fatty acid" as used herein is a broad term, and is to be given its ordinary and customary meaning to a person of ordinary skill in the art (and is not to be limited to a special or customized meaning), and refers without limitation to a fatty acid with 13-22 carbon atoms.

The term "very long chain fatty acid" as used herein is a broad term, and is to be given its ordinary and customary meaning to a person of ordinary skill in the art (and is not to be limited to a special or customized meaning), and refers without limitation to a fatty acid with 23 or more carbon atoms.

The term "derivative" as used herein is a broad term, and is to be given its ordinary and customary meaning to a person of ordinary skill in the art (and is not to be limited to a special or customized meaning), and refers without limitation to any compound as described herein incorporating one or more derivative groups, or being substituted by or functionalized to include one or more derivative groups. Derivatives include but are not limited to esters, amides, anhydrides, acid halides, thioesters, phosphates, triphosphates, and β-sulfenyl derivatives.

The term "hydrocarbon" as used herein is a broad term, and is to be given its ordinary and customary meaning to a person of ordinary skill in the art (and is not to be limited to a special or customized meaning), and refers without limitation to any moiety comprising only carbon and hydrogen atoms. A functionalized or substituted hydrocarbon moiety has one or more substituents as described elsewhere herein.

The term "lipid" as used herein is a broad term, and is to be given its ordinary and customary meaning to a person of ordinary skill in the art (and is not to be limited to a special or customized meaning), and refers without limitation to saturated and unsaturated oils and waxes, derivatives, amides, glycerides, small molecule metabolites, fatty alcohols, sterol and sterol derivatives, phospholipids, ceramides, sphingolipids, tocopherols, and carotenoids, among others.

The terms "pharmaceutically acceptable" as used herein is a broad term, and is to be given its ordinary and customary meaning to a person of ordinary skill in the art (and is not to be limited to a special or customized meaning), and refers without limitation to those compounds, materials, compositions, and/or dosage forms which are, within the scope of sound medical judgment, suitable for contact with the tissues of and/or for consumption by human beings and animals without excessive toxicity, irritation, allergic response, or other problem complications commensurate with a reasonable risk/benefit ratio.

The terms "pharmaceutically acceptable salts" and "a pharmaceutically acceptable salt thereof" as used herein are broad terms, and are to be given their ordinary and customary meaning to a person of ordinary skill in the art (and is not to be limited to a special or customized meaning), and refer without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity. In addition to salts, pharmaceutically acceptable precursors and derivatives of the compounds can be employed. Pharmaceutically acceptable amides, lower alkyl derivatives, and protected derivatives can also be suitable for use in compositions and methods of preferred embodiments. While it may be possible to administer the compounds of the preferred embodiments in the form of pharmaceutically acceptable salts, it is generally preferred to administer the compounds in neutral form.

The term "pharmaceutical composition" as used herein is a broad term, and is to be given its ordinary and customary meaning to a person of ordinary skill in the art (and is not to be limited to a special or customized meaning), and refers without limitation to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids or bases. Pharmaceutical compositions will generally be tailored to the specific intended route of administration.

The term "carrier" as used herein is a broad term, and is to be given its ordinary and customary meaning to a person of ordinary skill in the art (and is not to be limited to a special or customized meaning), and refers without limitation to a compound that facilitates the incorporation of a compound into cells or tissues. For example, without limitation, dimethyl sulfoxide (DMSO) is a commonly utilized carrier that facilitates the uptake of many organic compounds into cells or tissues of a subject. Water, saline solution, ethanol, and mineral oil are also carriers employed in certain pharmaceutical compositions.

The term "diluent" as used herein is a broad term, and is to be given its ordinary and customary meaning to a person of ordinary skill in the art (and is not to be limited to a special or customized meaning), and refers without limitation to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

The term "excipient" as used herein is a broad term, and is to be given its ordinary and customary meaning to a person of ordinary skill in the art (and is not to be limited to a special or customized meaning), and refers without limitation to a substance that is added to a pharmaceutical composition to provide, without limitation, bulk, consistency, stability, binding ability, lubrication, disintegrating ability etc., to the composition. A "diluent" is a type of excipient.

The term "subject" as used herein is a broad term, and is to be given its ordinary and customary meaning to a person of ordinary skill in the art (and is not to be limited to a special or customized meaning), and refers without limitation to an animal that is the object of treatment, observation or experiment. "Animal" includes cold- and warm-blooded vertebrates and invertebrates such as fish, shellfish, reptiles and, in particular, mammals. "Mammal" includes, without limitation, dolphins, mice, rats, rabbits, guinea pigs, dogs, cats, sheep, goats, cows, horses, primates, such as monkeys, chimpanzees, and apes, and, in particular, humans. In some embodiments, the subject is human.

The terms "treating," "treatment," "therapeutic," or "therapy" as used herein are broad terms, and are to be given their ordinary and customary meaning (and are not to be limited to a special or customized meaning) and, without limitation, do not necessarily mean total cure or abolition of the disease or condition. Any alleviation of any undesired markers, signs or symptoms of a disease or condition, to any extent, can be considered treatment and/or therapy. Furthermore, treatment may include acts that may worsen the patient's overall feeling of well-being or appearance.

The terms "therapeutically effective amount" and "effective amount" as used herein are broad terms, and are to be given its ordinary and customary meaning to a person of ordinary skill in the art (and are not to be limited to a special or customized meaning), and are used without limitation to indicate an amount of an active compound, or pharmaceutical agent, that elicits the biological or medicinal response indicated. For example, a therapeutically effective amount of compound can be the amount needed to prevent, alleviate or ameliorate markers or symptoms of a condition or prolong the survival of the subject being treated. This response may occur in a tissue, system, animal or human and includes alleviation of the signs or symptoms of the disease being treated. Determination of a therapeutically effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

The term "solvents" as used herein is a broad term, and is to be given its ordinary and customary meaning to a person of ordinary skill in the art (and is not to be limited to a special or customized meaning), and refers without limitation to compounds with some characteristics of solvency for other compounds or means, that can be polar or nonpolar, linear or branched, cyclic or aliphatic, aromatic, naphthenic and that includes but is not limited to: alcohols, derivatives, diesters, ketones, acetates, terpenes, sulfoxides, glycols, paraffins, hydrocarbons, anhydrides, heterocyclics, among others.

Any percentages, ratios or other quantities referred to herein are on a weight basis, unless otherwise indicated.

Small Molecule Metabolites

Small molecule metabolites are low molecular weight (typically less than 900 daltons, but sometimes higher) and can include but are not limited to amino acids, peptides, carbohydrates, cofactors and vitamins, xenobiotics, or lipids (including monohydroxy fatty acids, medium chain fatty acids, long chain fatty acids, very long chain fatty acids, dicarboxylic fatty acids, phosphatidylcholines, phosphatidylethanolamines, lysophospholipids, plasmalogens, lysoplasmalogens, monoacylglycerols, diacylglycerols, sphingomyelins, or ceramides) that can be identified and measured in the body and as provided herein. Small molecule metabolites can originate from ingestion of food or other oral products or produced endogenously. Small molecule metabolites are referred to and described using conventional nomenclature as is employed by one of skill in the art.

When specific compounds or classes of compounds are referred to herein, these compounds or classes of compounds may be produced by metabolic processes (e.g., by administration of a prodrug, or by endogenous production), or may be provided to a patient in a form of a pharmaceutical composition. It is not intended that the term "metabolite" of necessity requires production of a compound by a metabolic process in a patient to be treated. Instead, the compound, identified as a "metabolite" may be administered directly to the patient in a pharmaceutical composition rather than in a prodrug form that yields the compound as a metabolite in vivo. The term "metabolite" is employed as a broad term that is not intended to limit compounds to be administered to a patient to compounds produced by a particular method of synthesis (in vivo from a prodrug versus ex vivo).

A small molecule metabolite may be referred to by various names, for example, 2-methylserine may be referred to as 2-amino-3-hydroxy-2-methylpropanoic acid.

In some embodiments, the small molecule metabolite can be an amino acid, peptide, carbohydrate, cofactor and vitamin, xenobiotic, or lipid as provided herein. In further embodiments, one or more small molecule metabolites can include at least one amino acid, peptide, carbohydrate, cofactor and vitamin, xenobiotic, or lipid as provided herein.

Small molecule metabolites that are ideal candidates as both biomarkers and therapeutics are metabolites that are successfully detected in serum at high nanomolar or micromolar levels that have a low molecular weight (<900 daltons) and meet Lipinski's rule of five. All metabolites provided herein meet these criteria.

In some embodiments, a small molecule metabolite can be an amino acid, including but not limited to 2-methylserine, 4-hydroxyglutamate, N-acetyl-aspartyl-glutamate, 2-pyrrolidinone, trans-urocanate, imidazole proprionate, 1-ribosyl-imidazoleacetate, 5-imidazoleacetate, N-acetyl-histamine, hydantoin 5-prorionic acid, 5-hydroxylysine, 5-aminovalerate, 2-oxoadipate, xanthurenate, methionine sulfone, homocitrulline, trans-4-hydroxyproline, prolyl-hydroxyproline, or guanidinosuccinate. Derivatives can be synthesized by published methods.

In some embodiments, a small molecule metabolite can be a peptide, including but not limited to gamma-glutamyl-glutamine, or gamma-glutamylglycine; a carbohydrate, including but not limited to N6-carboxymethyllysine; a cofactor or vitamin, including N1-methyl-2-pyridone-5-carboxamide, N1-methyl-4-pyridone-3-carboxamide; or a xenobiotic, including but not limited to 2,3-dihydroxyisovalerate. Derivatives can be synthesized by published methods.

In some embodiments, a small molecule metabolite can be a monohyroxy fatty acid, including but not limited to 2-hydroxyocatnoate, 2-hydroxydecanoate, 8-hydroxyoctanoate, 2-hydroxymyristate, or 16-hydroxypalmitate. Derivatives can be synthesized by published methods.

In some embodiments, a small molecule metabolite can be a medium chain fatty acid, e.g., a fatty acid including but not limited to one containing a group such as heptanoate (C7:0, e.g., heptanoic acid), caprylate (C8:0, e.g., caprylic acid), pelargonate (C9:0, e.g., pelargonic acid), undecanoate (C11:0, e.g., undecanoic acid), or 10-undecanoate (C11:1n1, e.g., 10-undecanoic acid); a long chain fatty acid, including but not limited to pentadecanoate (C15:0, e.g., pentadecanoic acid), margarate (C17:0, e.g., margaric acid), 10-heptadecanoate (C17:1n7, e.g., 10-heptadecanoic acid), 10-nonadecanoate (19:1n9, e.g., 10-nonadecanoic acid), C20:0 fatty acid, or C20:2 fatty acid; a very long chain fatty acid, including but not limited to C24:0 fatty acid or C24:1 fatty acid; a branched chain fatty acid, including but not limited to 15-methylpalmitate (i17:0, e.g., methylpalmitic acid), 17-methylstearate (i19:0, e.g., 17-methylstearic acid), or 2-hydroxyphytanate (e.g., 2-hydroxyphytanic acid); or a dicarboxylate fatty acid, including but not limited to dodecadienoate (C12:2, e.g., dodecandioic acid) or docosadioate (C22-DC, e.g., docosadioic acid). Derivatives can be synthesized by published methods.

In some embodiments, a small molecule metabolite can be a part or product of fatty acid metabolism, including but not limited to propionylglycine, lignoceroylcarnitine (C24), cerotoylcarnitine (C26), N-palmitoylglycine, cis-4-decenoylcarnitine (C10:1), behenoylcarnitine (C22), pentadecanoylcarnitine (C15), or arachidonoylcholine. Derivatives can be synthesized by published methods.

In some embodiments, a small molecule metabolite can be a phosphatidylcholine, including but not limited to 1-stearoyl-2-arachidonoyl-GPC (18:0/20:4), 1-palmitoyl-2-arachidonoyl-GPC (16:0/20:4n6), PC (18:2/22:4), PC (20:0/14:1), PC (20:0/20:3), or PC (20:0/22:4); a phosphatidylethanolamine, including but not limited 1-palmitoyl-2-arachidonoyl-GPE (16:0/20:4), 1-stearoyl-2-arachidonoyl-GPE (18:0/20:4), or PE (16:0/16:0); a phosphatidylserine, including but not limited to 1-stearoyl-2-oleoyl-GPS (18:0/18:1); a lysophospholipid, including but not limited 1-arachidonoyl-GPC (20:4n6), 1-lignoceroyl-GPC (24:0), or 1-arachidonoyl-GPE (20:4n6). Derivatives can be synthesized by published methods.

In some embodiments, a small molecule metabolite can be a plasmalogen, including but not limited to 1-(1-enyl-palmitoyl)-2-arachidonoyl-GPE (P-16:0/20:4), 1-(1-enyl-palmitoyl)-2-oleoyl-GPC (P-16:0/18:1), 1-(1-enyl-palmitoyl)-2-arachidonoyl-GPC (P-16:0/20:4), or 1-(1-enyl-stearoyl)-2-arachidonoyl-GPE (P-18:0/20:4); or a lysoplasmalogen, including but not limited to 1-(1-enyl-palmitoyl)-GPC (P-16:0). Derivatives can be synthesized by published methods.

In some embodiments, a small molecule metabolite can be a monoacylglycerol (MAG), including but not limited to MAG (12:0), MAG (17:0), MAG (20:0), MAG (20:2), 1-arachidonylglycerol (20:4) or 1-heptadecenoylglycerol (17:1); or a diacylglycerol (DAG), including but not limited to DAG (14:1/18:1), stearoyl-arachidonoyl-glycerol (18:0/20:4) [2], oleoyl-arachidonoyl-glycerol (18:1/20:4) [1], or oleoyl-arachidonoyl-glycerol (18:1/20:4) [2]. Derivatives can be synthesized by published methods.

In some embodiments, a small molecule metabolite can be a sphingomyelin, including but not limited to stearoyl sphingomyelin (d18:1/18:0), behenoyl sphingomyelin (d18:1/22:0), tricosanoyl sphingomyelin (d18:1/23:0), lignoceroyl sphingomyelin (d18:1/24:0), sphingomyelin (d18:2/23:1), sphingomyelin (d18:2/24:2), sphingomyelin (d17:1/14:0, d16:1/15:0), sphingomyelin (d17:1/16:0, d18:1/15:0, d16:1/17:0), sphingomyelin (d17:2/16:0, d18:2/15:0), sphingomyelin (d18:1/17:0, d17:1/18:0, d19:1/16:0), sphingomyelin (d18:1/19:0, d19:1/18:0), sphingomyelin (d18:1/21:0, d17:1/22:0, d16:1/23:0), sphingomyelin (d18:2/21:0, d16:2/23:0), or sphingomyelin (d18:2/23:0, d18:1/23:1, d17:1/24:1). Derivatives can be synthesized by published methods.

In some embodiments, a small molecule metabolite can be a ceramide, including but not limited to CER (14:0), HCER (26:1), or LCER (26:0). Derivatives can be synthesized by published methods.

In some embodiments, a derivative of a small molecule metabolite can be a β-sulfenyl derivative. It is thought that β-sulfenyl derivatives, such as an acid or ester, can be resistant to β-oxidation in the body. Derivatives can be synthesized by published methods.

In some embodiments, a small molecule metabolite is provided in a bioavailable form. The term "bioavailability" refers to the fraction of an administered dose of unchanged drug that reaches the systemic circulation, one of the principal pharmacokinetic properties of drugs. By definition, when a medication is administered intravenously, its bioavailability is 100%. As employed herein, the term "bioavailable" refers to a form of the small molecule metabolite that is successfully absorbed by the body when using methods of administration other than intravenous, for example, an oral therapeutic). In some embodiments, small molecule metabolite-based compositions may include adaptions that optimize absorption.

A pure or purified small molecule metabolite may exist in various physical states. For example, 4-hydroxyglutamate exists as a white powder that is stable at room temperature; this compound can be purchased in forms suitable for research purposes in small amounts from some commercial suppliers (for example, from Sigma-Aldrich Corp., of St. Louis, MO). Other small molecule metabolites, or stereoisomers, or solvates, or esters, or salts or other derivatives thereof, may exist as oils, solids, crystalline solids, or gases.

A small molecule metabolite or the pharmaceutically acceptable salts or derivatives thereof, may be provided in a purity (e.g., a percentage of the small molecule metabolite, or its pharmaceutically acceptable salts or derivatives, in a bulk form) of at least about 10%, at least about 20%, at least about 30%, at least about 40%, at least about 50%, at least about 60%, at least about 70%, at least about 80%, at least about 90%, at least about 95%, at least about 98%, at least about 99%, at least about 99.9%, at least about 99.99%, or substantially pure, wherein substantially pure may include, but not be limited to, a product with impurities at a level such that no physiological effect from the presence of the impurities is detectable. A mixture of small molecule metabolites, such as, for example, an amino acid and/or lipid, or pharmaceutically acceptable salts or derivatives thereof, may be present in a purity of at least about 10%, at least about 20%, at least about 30%, at least about 40%, at least about 50%, at least about 60%, at least about 70%, at least about 80%, at least about 90%, at least about 95%, at least about 98%, at least about 99%, at least about 99.9%, at least about 99.99%, or substantially pure. The small molecule metabolite, or a mixture thereof, or a pharmaceutically acceptable salt or derivative thereof, may be free from other small molecule metabolites. Without limitation, a small molecule metabolite as provided herein may be substantially free from other small molecule metabolites, singly or taken as a group; small molecule metabolites to exclude, for example, can include palmitic acid (C16:0) or stearic acid (C18:0). In some embodiments, a small molecule metabolite as provided herein may be substantially free from other species of lipids not included herein.

A small molecule metabolite, such as an amino acid, peptide, carbohydrate, cofactor, vitamins, xenobiotic, or lipid, or a pharmaceutically acceptable salt or derivative thereof, may be from any source. In some embodiments, a small molecule metabolite, or its pharmaceutically acceptable salts or derivatives, may be present in natural sources, may be isolated from natural sources, may be semi-synthetic, may be synthetic, or may be a mixture of one or more of these. The small molecule metabolite, or its pharmaceutically acceptable salts or derivatives, may be produced in a laboratory, may be produced in nature, may be produced by enzymatic processes, may be produced by wild microbes, may be produced by genetically modified microbes, may be isolated from animal tissues, may be produced by chemical synthesis, or may be produced by a plurality of these processes.

The small molecule metabolite may be derived from natural sources, e.g., fish oils, or can be synthesized by methods as are known in the art. In some embodiments, the small molecule metabolite may be contaminated with undesired components present in unrefined or unpurified natural products. In such situations, it can be desirable to remove undesired components, or to increase the concentration of desired components using known separation or purification techniques.

In any compound described, all tautomeric forms are also intended to be included. Without limitation, all tautomers of carboxylic groups are intended to be included.

In any compound described herein having one or more double bond(s) generating geometrical isomers that can be defined as E or Z, each double bond may independently be E or Z, or a mixture thereof.

Where compounds disclosed herein have unfilled valencies, then the valencies are to be filled with hydrogens or isotopes thereof, e.g., hydrogen-1 (protium) and hydrogen-2 (deuterium).

The small molecule metabolite, such as an amino acid, peptide, carbohydrate, cofactors and vitamin, xenobiotics, or lipid, as described herein, includes crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

The compounds described herein can be labeled isotopically. In some circumstances, substitution with isotopes such as deuterium may afford certain therapeutic advantages resulting from greater metabolic stability, such as, for example, increased in vivo half-life or reduced dosage requirements. Isotopic substitution may be beneficial in monitoring subject response to administration of a compound, for example, by providing opportunity for monitoring of the fate of an atom in a compound. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Compositions Including One or More Small Molecule Metabolites

Formulations including a small molecule metabolite, such as an amino acid, peptide, carbohydrate, cofactor, vitamins, xenobiotic, or lipid, or a salt or derivative thereof, and at least one excipient are provided. It is generally preferred to administer the compounds of the embodiments in oral formulations; however, other routes of administration are also contemplated, such as topical. The formulations are suitable for use as consumer health and wellness products, including over the counter (OTC) products, as well as supplements and foodstuffs.

The compositions of the embodiments may be used in cosmetic, cosmeceutical and general skincare compositions or provided in pharmaceutical compositions, and can be employed in the promotion of healthy skin, skin regeneration and enhanced wound healing. Successful wound healing occurs when the tissue remodeling process alleviates the inflammatory response of the innate immune system and minimizes the scar forming process that occurs when fibrous tissue replaces normal skin after an injury. Less efficient or delayed wound healing often produces unsightly, irritating, and painful scars such as keloids or hypertrophic scars. The compositions can help treat or prevent dermatologic conditions such as skin dryness, dullness, loss of elasticity, lack of radiance, exaggerated lines and wrinkles, stretch marks, spider vessels, red blotchiness, smile lines, deep nasolabial fold lines, crow's feet, fine lines/wrinkles, vertical lines between the eyebrows, horizontal forehead lines, sagging thin/frail skin, skin redness, dullness, the appearance of photodamaged skin, the appearance of fine lines and wrinkles, hyperpigmentation, age spots, aged skin, and generally increasing the quality of skin.

The compositions of the embodiments can also be employed in the connection with mucous membranes, e.g., the lips and the vaginal mucosa. When applied to the vaginal mucosa, a vaginal applicator can be employed as are commercially available. Suitable applicators can be in a form of a pre-filled syringe, a tube attached to a prefilled squeezable reservoir, a prepackaged wand including a preselected amount of composition, or a universal vaginal applicator including perforations along its length for dispensing the composition through the perforations.

Certain of the compositions can contain further therapeutic agents., e.g., locally acting drugs such as antibacterial drugs, antiprotozoal drugs, antifungal drugs, antiviral drugs, spermicidal agents, prostaglandins, and steroids. Drugs suitable for delivery include bromocriptine, sildenafil, oxytocin, calcitonin, luteinizing hormone-releasing hormone and analogues, insulin, human growth hormone, oxybutynin, and steroids used in hormone replacement therapy or for contraception. Antifungal drugs include clotrimazole, econazole, miconazole, terbinafine, fluconazole, ketoconazole, and amphotericin. Antibiotics include amoxicillin, doxycycline, cephalexin, ciprofloxacin, clindamycin, metronidazole, azithromycin, sulfamethoxazole/trimethoprim, amoxicillin/clavulanate, and levofloxacin. Classes of antibiotics include penicillins, tetracyclines, cephalosporins, quinolones, lincomycins, macrolides, sulfonamides, glycopeptides, aminoglycosides, and carbapenems. Types of hormones include 5-alpha-reductase inhibitors, adrenal cortical steroids, corticotropin, glucocorticoids, mineralocorticoids, adrenal corticosteroid inhibitors, antiandrogens, antidiuretic hormones, antigonadotropic agents, antithyroid agents, aromatase inhibitors, calcitonin, estrogen receptor antagonists, gonadotropin-releasing hormone antagonists, growth hormone receptor blockers, growth hormones, insulin-like growth factor, parathyroid hormone and analogs, progesterone receptor modulators, prolactin inhibitors, selective estrogen receptor modulators, sex hormones, androgens and anabolic steroids, contraceptives, estrogens, gonadotropin releasing hormones, gonadotropins, progestins, sex hormone combinations, somatostatin and somatostatin analogs, synthetic ovulation stimulants, and thyroid drugs. Antiviral agents include adamantane antivirals, antiviral boosters, antiviral combinations, antiviral interferons, chemokine receptor antagonist, integrase strand transfer inhibitor, miscellaneous antivirals, neuraminidase inhibitors, NNRTIs, NS5A inhibitors, nucleoside reverse transcriptase inhibitors (NRTIs), protease inhibitors, and purine nucleosides. Drugs for treating skin conditions include acne drugs (isotretinoin), atopic dermatitis drugs (topical steroids), herpes zoster drugs (antivirals such as valacyclovir), hives (antihistamines like loratadine or fexofenadine, omalizumab), sunburn (lidocaine), contact dermatitis (antihistamines, topical steroids), diaper rash (zinc oxide), rosacea (metronidazole, doxycycline, azelaic acid, isotretinoin, beta blockers, estrogen), athlete's foot (antifungals), and basal cell carcinoma (imiquimod, fluorouracil, vismodegib).

The compositions of the embodiments include topical formulations containing at least one excipient. Excipients can include a nonaqueous or aqueous carrier, and one or more agents selected from moisturizing agents, pH adjusting agents, deodorants, fragrances, chelating agents, preservatives, emulsifiers, thickeners, solubilizing agents, penetration enhancers, anti-irritants, colorants, surfactants, beneficial agents, pharmaceutical agents, and other components as known in the art for use in connection with topical formulations for treatment of the skin. The composition can be formulated such that preservatives need not be employed.

To facilitate application, the composition may be provided as an ointment, an oil, a lotion, a paste, a powder, a gel, or a cream. The composition may also include additional ingredients such as a protective agent, an emollient, an astringent, a humectant, a sun screening agent, a sun tanning agent, a UV absorbing agent, an antibiotic agent, an antifungal agent, an antiviral agent, an antiprotozoal agent, an anti-acne agent, an anesthetic agent, a steroidal anti-inflammatory agent, a non-steroidal anti-inflammatory agent, an antipruritic agent, an additional antioxidant agent, a chemotherapeutic agent, an anti-histamine agent, a vitamin or vitamin complex, a hormone, an anti-dandruff agent, an anti-wrinkle agent, an anti-skin atrophy agent, a skin whitening agent, a cleansing agent, and combinations thereof. In a further embodiment, the composition may avoid animal or cellular-based materials to avoid skin irritation. The composition can be applied to the dermis, or to mucous membranes.

The compositions can be employed to promote healthy skin, skin regeneration, enhanced wound healing, and to treat skin conditions such as inflammation, redness, soreness, skin sensitivity, dry skin, bruising, and similar conditions. Suitable methods for objectively measuring improvement in skin redness and inflammation may include tristimulus colorimetry, narrow-band reflectance spectroscopy, diffuse reflectance spectroscopy, skin reflectance spectroscopy, and/or UV photography.

Some embodiments include administering the small molecule metabolite, such as an amino acid, peptide, carbohydrate, cofactor, vitamins, xenobiotic, or lipid, or a salt or derivative thereof in topical formulations; however, other routes of administration are also contemplated (e.g., mucosal, subdermal, oral, or the like) in addition to oral administration. Contemplated routes of administration include but are not limited to topical, mucosal, and subcutaneous. Suitable liquid forms include suspensions, emulsions, solutions, and the like. Unit dosage forms can also be provided, e.g., individual packets with a premeasured amount of the formulation, configured for administration to a body part on a predetermined schedule pre-procedure and post-procedure. Unit dosage forms configured for administration twice or three times a day are particularly preferred; however, in certain embodiments it can be desirable to configure the unit dosage form for administration once a day, four times a day, or more.

In some embodiments, the topical and other formulations typically comprise from about 0.001 wt. % or less to about 50 wt. % or more of active ingredient, such as the small molecule metabolite, such as an amino acid, peptide, carbohydrate, cofactor, vitamins, xenobiotic, or lipid, or a salt or derivative thereof, preferably from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %.

Compositions and formulations for topical administration can include transdermal patches, ointments, lotions, creams, gels, drops, sprays, liquids, aerosols, and powders. Conventional pharmaceutical carriers, aqueous, powder or oily bases, thickeners and the like may be employed. In certain applications, an ointment, lotion, cream, gel or similar formulation can be provided that can be applied to the skin using the fingers. Such formulations are typically provided in a squeeze tube or bottle or a pot, or in a roll-on, wherein a ball is secured in the top of a container of the formulation, wherein the ball is permitted to roll. By rolling the ball over the skin surface, liquid in the container is transferred to the skin in a controlled manner. An alternative delivery mechanism includes a container with a perforated lid with a mechanism for advancing an extrudable formulation through the lid. In another form, a gel formulation with sufficient structural integrity to maintain its shape is provided, which is advanced up a tube and applied to the skin (e.g., in a stick form). An advantage of the stick form is that only the formulation contacts the skin in the application process, not the fingers or a portion of a container. A liquid or gel can also be placed using an applicator, e.g., a wand, a sponge, a syringe, or other suitable method.

In some embodiments, the small molecule metabolite, such as an amino acid, peptide, carbohydrate, cofactor, vitamins, xenobiotic, or lipid, or a salt or derivative thereof, can be in combination therapy, or in admixture with a suitable carrier, diluent, or excipient, and can contain auxiliary substances such as wetting or emulsifying agents, pH buffering agents, gelling or viscosity enhancing additives, preservatives, scenting agents, colors, and the like, depending upon the route of administration and the preparation desired. Techniques for formulation and administration of the compounds described herein are known to those skilled in the art. See, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulations include, without limitation, monoglycerides, diglycerides, sulfatides, lysolecithin, phospholipids, saponin, bile acids, and the like. The presence of such additional components can influence the physical state, solubility, stability, rate of release, rate of clearance, and penetration of active ingredients.

The compositions for topical administration comprise the small molecule metabolite, such as an amino acid, peptide, carbohydrate, cofactor, vitamins, xenobiotic, or lipid, or a salt or derivative thereof and a dermatologically acceptable vehicle. The vehicle may be aqueous or nonaqueous. The dermatologically acceptable vehicle used in the topical composition may be in the form of a lotion, a gel, an ointment, a liquid, a cream, or an emulsion. If the vehicle is an emulsion, the emulsion may have a continuous aqueous phase and a discontinuous nonaqueous or oil phase (oil-in-water emulsion), or a continuous nonaqueous or oil phase and a discontinuous aqueous phase (water-in-oil emulsion). When administered topically in liquid or gel form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or *arachis* oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain coloring and scenting agents.

In certain embodiments, a silicone elastomer (e.g., dimethicone crosspolymer) is employed to increase delivery and penetration of the small molecule metabolite, such as an amino acid, peptide, carbohydrate, cofactor, vitamins, xenobiotic, or lipid, or a salt or derivative thereof, into the skin. The pharmaceutical excipients used in the topical preparations of the compositions may be selected from the group consisting of solvents, emollients and/or emulsifiers, oil bases, preservatives, antioxidants, tonicity adjusters, penetration enhancers and solubilizers, chelating agents, buffering agents, surfactants, one or more polymers, and combinations thereof.

Suitable solvents for an aqueous or hydrophilic topical formulation include water; ethyl alcohol; isopropyl alcohol; mixtures of water and ethyl and/or isopropyl alcohols; glycerin; ethylene, propylene or butylene glycols; DMSO; and mixtures thereof. Suitable solvents for hydrophobic topical formulations include mineral oils, vegetable oils, and silicone oils. If desired, the compositions as described herein may be dissolved or dispersed in a hydrophobic oil phase, and the oil phase may then be emulsified in an aqueous phase comprising water, alone or in combination with lower alcohols, glycerin, and/or glycols. Anhydrous formulations may also be employed; however, in certain embodiments it may be acceptable to provide water based compositions, or to permit a limited amount of water to be present.

Viscosity of the compositions can be maintained at the selected level using a pharmaceutically acceptable thickening agent. Suitable viscosity enhancers or thickeners which may be used to prepare a viscous gel or cream with an aqueous base include sodium polyacrylate, xanthan gum, polyvinyl pyrrolidone, acrylic acid polymer, carragenans, hydroxyethyl cellulose, hydroxypropyl cellulose, methyl cellulose, ethyl cellulose, propyl cellulose, hydroxypropyl methyl cellulose, polyethoxylated polyacrylamides, polyethoxylated acrylates, and polyethoxylated alkane thiols. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the thickening agent selected. An amount is preferably used that will achieve the selected viscosity. Viscous compositions are normally prepared from solutions by the addition of such thickening agents, or by employing a base that has an acceptable level of viscosity.

Suitable emollients include hydrocarbon oils and waxes such as mineral oil, petrolatum, paraffin, ceresin, ozokerite, microcrystalline wax, polyethylene, squalene, perhydrosqualene, silicone oils, triglyceride esters, acetoglyceride esters, such as acetylated monoglycerides; ethoxylated glycerides, such as ethoxylated glyceryl monostearate; alkyl esters of fatty acids or dicarboxylic acids.

Suitable silicone oils for use as emollients include dimethyl polysiloxanes, methyl(phenyl) polysiloxanes, and water-soluble and alcohol-soluble silicone glycol copolymers. Suitable triglyceride esters for use as emollients include vegetable and animal fats and oils including castor oil, safflower oil, cotton seed oil, corn oil, olive oil, cod liver oil, almond oil, avocado oil, palm oil, sesame oil, and soybean oil.

Suitable esters of carboxylic acids or diacids for use as emollients include methyl, isopropyl, and butyl esters of fatty acids. Specific examples of alkyl esters including hexyl laurate, isohexyl laurate, iso-hexyl palmitate, isopropyl palmitate, decyl oleate, isodecyl oleate, hexadecyl stearate, decyl stearate, isopropyl isostearate, dilauryl lactate, myristyl lactate, and cetyl lactate; and alkenyl esters of fatty acids such as oleyl myristate, oleyl stearate, and oleyl oleate. Specific examples of alkyl esters of diacids include diisopropyl adipate, diisohexyl adipate, bis(hexyldecyl) adipate, and diisopropyl sebacate.

Other suitable classes of emollients or emulsifiers which may be used in the topical formulations include fatty acids, fatty alcohols, fatty alcohol ethers, ethoxylated fatty alcohols, fatty acid esters of ethoxylated fatty alcohols, and waxes.

Specific examples of fatty acids for use as emollients include pelargonic, lauric, myristic, palmitic, stearic, isostearic, hydroxystearic, oleic, linoleic, ricinoleic, arachidic, behenic, and erucic acids. Specific examples of fatty alcohols for use as emollients include lauryl, myristyl, cetyl, hexadecyl, stearyl, isostearyl, hydroxystearyl, oleyl, ricinoleyl, behenyl, and erucyl alcohols, as well as 2-octyl dodecanol.

Specific examples of waxes suitable for use as emollients include lanolin and derivatives thereof including lanolin oil, lanolin wax, lanolin alcohols, lanolin fatty acids, isopropyl lanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols esters, hydrogenolysates of lanolin, hydrogenated lanolin, ethoxylated hydrogenated lanolin, ethoxylated sorbitol lanolin, and liquid and semisolid lanolin. Also usable as waxes include hydrocarbon waxes, ester waxes, and amide waxes. Useful waxes include wax esters such as beeswax, spermaceti, myristyl myristate and stearyl stearate; beeswax derivatives, e.g., polyoxyethylene sorbitol beeswax; and vegetable waxes including carnauba and candelilla waxes.

Polyhydric alcohols and polyether derivatives may be used as solvents and/or surfactants in the topical formulations. Suitable polyhydric alcohols and polyethers include propylene glycol, dipropylene glycol, polypropylene glycols 2000 and 4000, poly(oxyethylene-co-oxypropylene) glycols, glycerol, sorbitol, ethoxylated sorbitol, hydroxypropylsorbitol, polyethylene glycols 200-6000, methoxy polyethylene glycols 350, 550, 750, 2000 and 5000, poly[ethylene oxide] homopolymers (100,000-5,000,000), polyalkylene glycols and derivatives, hexylene glycol, 2-methyl-2,4-pentanediol, 1,3-butylene glycol, 1,2,6-hexanetriol, 2-ethyl-1, 3-hexanediol, vicinal glycols having 15 to 18 carbon atoms, and polyoxypropylene derivatives of trimethylolpropane.

Polyhydric alcohol esters may be used as emulsifiers or emollients. Suitable polyhydric alcohol esters include ethylene glycol mono- and di-fatty acid esters, diethylene glycol mono- and di-fatty acid esters, polyethylene glycol (200-6000) mono- and di-fatty acid esters, propylene glycol mono- and di-fatty esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Suitable emulsifiers for use in topical formulations include anionic, cationic, nonionic, and zwitterionic surfactants. Preferred ionic emulsifiers include phospholipids, such as lecithin and derivatives.

The small molecule metabolite, such as an amino acid, peptide, carbohydrate, cofactor, vitamins, xenobiotic, or lipid contained herein, or a salt or derivative thereof, can be formulated as a liposome. The small molecule metabolite can be a component of the lipid portion of the liposome or can be encapsulated in the aqueous portion of the liposome. The small molecule metabolite, such as an amino acid, peptide, carbohydrate, cofactor, vitamins, xenobiotic, or lipid contained herein, or a salt or derivative thereof, can also be coformulated with a cyclodextrin. The cyclodextrin can be, for example, hydroxypropyl-β-cyclodextrin or a sulfobutylether cyclodextrin. Lecithin and other phospholipids may be used to prepare liposomes containing active ingredients as described herein. Formation of lipid vesicles occurs when phospholipids such as lecithin are placed in water and consequently form one bilayer or a series of bilayers, each separated by water molecules, once enough energy is supplied. Liposomes can be created by sonicating phospholipids in water. Low shear rates create multilamellar liposomes. Continued high-shear sonication tends to form smaller unilamellar liposomes. Hydrophobic chemicals can be dissolved into the phospholipid bilayer membrane. The lipid bilayers of the liposomes deliver the compositions as described herein.

The topical formulations may contain micelles, or an aggregate of surfactant molecules dispersed in an aqueous solution. Micelles may be prepared by dispersing an oil solvent in an aqueous solution comprising a surfactant, where the surfactant concentration exceeds the critical micelle concentration. The resulting formulation contains micelles, i.e., spherical oil droplets surrounded by a membrane of polar surfactant molecules, dispersed in the aqueous solvent.

Sterols including, for example, cholesterol and cholesterol fatty acid esters; amides such as fatty acid amides, ethoxylated fatty acid amides, and fatty acid alkanolamides may also be used as emollients and/or penetration enhancers.

A pharmaceutically acceptable preservative can be employed to increase the shelf life of the composition. Other suitable preservatives and/or antioxidants for use in topical formulations include benzalkonium chloride, benzyl alcohol, phenol, urea, parabens, butylated hydroxytoluene (BHT), butylated hydroxyanisole (BHA), tocopherol, thimerosal, chlorobutanol, or the like, and mixtures thereof, can be employed. If a preservative, such as an antioxidant, is employed, the concentration is typically from about 0.02% to about 2% based on the total weight of the composition, although larger or smaller amounts can be desirable depending upon the agent selected. Reducing agents, as described herein, can be advantageously used to maintain good shelf life of the formulation. It is generally observed that the anhydrous formulations of the embodiments exhibit satisfactory stability, such that a preservative can be omitted from the formulation.

Suitable chelating agents for use in topical formulations include ethylene diamine tetraacetic acid, alkali metal salts thereof alkaline earth metal salts thereof, ammonium salts thereof, and tetraalkyl ammonium salts thereof.

The carrier preferably has a pH of between about 4.0 and 10.0, more preferably between about 6.8 and about 7.8. The pH may be controlled using buffer solutions or other pH modifying agents. Suitable pH modifying agents include phosphoric acid and/or phosphate salts, citric acid and/or citrate salts, hydroxide salts (i.e., calcium hydroxide, sodium hydroxide, potassium hydroxide) and amines, such as triethanolamine. Suitable buffer solutions include a buffer comprising a solution of monopotassium phosphate and dipotassium phosphate, maintaining a pH of between 5.8 and 8; and a buffer comprising a solution of monosodium phosphate and disodium phosphate, maintaining a pH of between 6 and 7.5. Other buffers include citric acid/sodium citrate, and dibasic sodium phosphate/citric acid. The compositions of the embodiments are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. It can be desirable to include a reducing agent in the formulation, such as vitamin C, vitamin E, or other reducing agents as are known in the pharmaceutical arts.

Surfactants can also be employed as excipients, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

When the formulations of the embodiments are administered by subcutaneous injection, it is preferably in the form of a pyrogen-free, parenterally acceptable aqueous solution or oleaginous suspension, emulsion or solution. Suspensions can be formulated according to methods well known in the art using suitable dispersing or wetting agents and suspending agents. The preparation of acceptable aqueous or non-aqueous solutions with suitable properties, e.g., pH, isotonicity, stability, and the like, is within the skill in the art. For example, an isotonic vehicle such as 1,3-butanediol, water, isotonic sodium chloride solution, Ringer's solution, dextrose solution, dextrose and sodium chloride solution, lactated Ringer's solution, or other vehicles as are known in the art can be employed, or a fixed oil can be employed conventionally as a solvent or suspending medium, e.g., synthetic mono or diglycerides, fatty acids, or the like. The formulations can also contain stabilizers, preservatives, buffers, antioxidants, or other additives known to those of skill in the art.

In certain embodiments, it can be advantageous to include additional agents having pharmacological activity. Anti-infective agents include, but are not limited to, anthelmintic (mebendazole), antibiotics including aminoglycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin, clindamycin, colistimethate sodium, polymyxin b sulfate, vancomycin, antivirals including acyclovir, amantadine, didanosine, efavirenz, foscarnet, ganciclovir, indinavir, lamivudine, nelfinavir, ritonavir, saquinavir, stavudine, valacyclovir, valganciclovir, zidovudine, quinolones (ciprofloxacin, levofloxacin), sulfonamides (sulfadiazine, sulfisoxazole), sulfones (dapsone), furazolidone, metronidazole, pentamidine, sulfanilamidum *crystallinum*, gatifloxacin, and sulfamethoxazole/trimethoprim. Anesthetics can include, but are not limited to, ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and phenazopyridine. Anti-inflammatory agents include but are not limited to, nonsteroidal anti-inflammatory drugs (NSAIDs) such as aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinonide, betamethasone dipropionate, betamethasone valerate, desonide, desoximetasone, fluocinolone, triamcinolone, clobetasol propionate, and dexamethasone.

In certain embodiments, the addition of emollients, emulsion stabilizers, moisturizers, excipients, and other compounds may be modified to enhance the sensory properties of the topical compositions, including but not limited to: skin feel (silkiness, lightness, creaminess, etc.), absorbency (required time at which product loses wet feel and is no longer perceived on skin), consistency, firmness, spreadability (e.g. viscosity, flow onset, shear rates), stickiness, integrity of shape, glossiness, hydrophilicity or hydrophobicity, and others.

In certain embodiments systemic administration of the small molecule metabolite, such as an amino acid, peptide, carbohydrate, cofactor, vitamins, xenobiotic, or lipid, or a salt or derivative thereof, can be desirable. In such embodiments, the small molecule metabolite, such as an amino acid, peptide, carbohydrate, cofactor, vitamins, xenobiotic, or lipid, or a salt or derivative thereof are formulated into a composition suitable for oral administration, but other routes of administration are also contemplated.

The compositions described herein can be administered by themselves to a subject, or in compositions where they are mixed with other active agents, as in combination therapy, or with carriers, diluents, excipients or combinations thereof. Formulation is dependent upon the route of administration chosen. Techniques for formulation and administration of the compounds described herein are known to those skilled in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

The compositions disclosed herein may be manufactured into administrable forms by a process that is itself known, e.g., by means of conventional mixing, dissolving, granulating, dragee-making, levigating, emulsifying, encapsulating, entrapping, tableting, or extracting processes. Many of the compounds used in the pharmaceutical combinations disclosed herein may be provided as salts with pharmaceutically acceptable counterions.

Multiple techniques of administering a small molecule metabolite, such as an amino acid, peptide, carbohydrate, cofactor, vitamins, xenobiotic, or lipid, or a salt or derivative thereof, exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Contemplated herein is any combination of the forgoing, or other methods as would be known to one of ordinary skill in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

In practice, the small molecule metabolite, such as an amino acid, peptide, carbohydrate, cofactor, vitamins, xenobiotic, or lipid, or a salt or derivative thereof may be combined as the active ingredient in intimate admixture with a pharmaceutical carrier according to conventional pharmaceutical compounding techniques. The small molecule metabolite, such as an amino acid, peptide, carbohydrate, cofactor, vitamins, xenobiotic, or lipid, or a salt or derivative thereof can be added directly to, e.g., a gelatin capsule or a softgel capsule for consumption by the patient. In other embodiments, carriers can be employed. The carrier can take a wide variety of forms depending on the form of preparation desired for administration. Thus, the compositions provided herein can be presented as discrete units suitable for oral administration such as capsules, cachets or tablets each containing a predetermined amount of the active ingredient. Further, the compositions can be presented as an oil, a powder, as granules, as a solution, as a suspension in an aqueous liquid, as a non-aqueous liquid, as an oil-in-water emulsion, or as a water-in-oil liquid emulsion, similar to the topical formulations described elsewhere herein, but using components suitable for human consumption. In addition to the common dosage forms set out above, the compositions provided herein can also be administered by controlled release and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredients with liquid carriers or finely divided solid carriers or both. The product can then be conveniently shaped into the desired presentation.

A formulation may also be administered in a local rather than systemic manner, for example, via injection of the composition directly into a target area, e.g., in a depot or sustained release formulation. Furthermore, a targeted drug delivery system for the composition may be used, for example, in a liposome coated with a tissue specific antibody.

The compositions may contain the small molecule metabolite, such as an amino acid, peptide, carbohydrate, cofactor, vitamins, xenobiotic, or lipid, or a salt or derivative thereof in an amount effective for the desired therapeutic effect. In some embodiments, the compositions are in a unit dosage form and comprise from about 0.1 mg or less to about 5000 mg or more of small molecule metabolite, such as an amino acid, peptide, carbohydrate, cofactor, vitamins, xenobiotic, or lipid, or a salt or derivative thereof per unit dosage form. In further embodiments, the compositions comprise from about 1 to about 500 mg per unit dosage form or from about 500 to 5000 mg per unit dosage form of small molecule metabolite, such as an amino acid, peptide, carbohydrate, cofactor, vitamins, xenobiotic, or lipid, or a salt or derivative thereof. Such dosage forms may be solid, semisolid, liquid, an emulsion, or adapted for delivery via aerosol or the like for inhalation administration.

The carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, lower alcohols, and water. Examples of gaseous carriers include carbon dioxide and nitrogen.

The compositions provided herein can be prepared as solutions or suspensions of the small molecule metabolite, such as an amino acid, peptide, carbohydrate, cofactor, vitamins, xenobiotic, or lipid, or a salt or derivative thereof in water or nonaqueous liquids. A suitable surfactant can be included such as, for example, hydroxypropylcellulose. Dispersions can also be prepared in glycerol, liquid polyethylene glycols, and mixtures thereof in oils. Further, a preservative can be included to, for example, prevent the detrimental growth of microorganisms.

Compositions provided herein suitable for injectable use include sterile aqueous solutions or dispersions. Furthermore, the compositions can be in the form of sterile powders for the extemporaneous preparation of such sterile injectable solutions or dispersions. The compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

In addition to the aforementioned carrier ingredients, the formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood or other bodily fluids of the intended recipient. Compositions containing a compound provided herein, or pharmaceutically acceptable salt or derivative thereof, can also be prepared in powder or liquid concentrate form for dilution.

Contemplated herein are compositions including the small molecule metabolite, such as an amino acid, peptide, carbohydrate, cofactor, vitamins, xenobiotic, or lipid, or a salt or derivative thereof as described herein in combination with at least one additional active agent. The small molecule metabolite, such as an amino acid, peptide, carbohydrate, cofactor, vitamins, xenobiotic, or lipid, or a salt or derivative thereof and the at least one additional active agent(s) may be present in a single formulation or in multiple formulations provided together, or may be unformulated. In some embodiments, the small molecule metabolite, such as an amino acid, peptide, carbohydrate, cofactor, vitamins, xenobiotic, or lipid, or a salt or derivative thereof can be administered with one or more additional agents together in a single composition. For example, the small molecule metabolite, such as an amino acid, peptide, carbohydrate, cofactor, vitamins, xenobiotic, or lipid, or a salt or derivative thereof can be administered in one composition, and at least one of the additional agents can be administered in a second composition. In a further embodiment, the small molecule metabolite, such as an amino acid, peptide, carbohydrate, cofactor, vitamins, xenobiotic, or lipid, or a salt or derivative thereof and the at least one additional active agent(s) are co-packaged in a kit. For example, a drug manufacturer, a drug reseller, a physician, a compounding shop, or a pharmacist can provide a kit comprising the small molecule metabolite, such as an amino acid, peptide, carbohydrate, cofactor, vitamins, xenobiotic, or lipid, or a salt or derivative thereof in combination with another product or component for delivery to a patient. Such additional components can include anti-infective agents, anti-inflammatory agents, anesthetics, or the like.

Some embodiments described herein relate to oral compositions of small molecule metabolite, such as an amino acid, peptide, carbohydrate, cofactor, vitamins, xenobiotic, or lipid, or a salt or derivative thereof, which can include a therapeutically effective amount of the small molecule metabolite, such as an amino acid, peptide, carbohydrate, cofactor, vitamins, xenobiotic, or lipid, or a salt or derivative thereof described herein and a pharmaceutically acceptable carrier, diluent, excipient or combination thereof. The compositions can include the small molecule metabolite, such as an amino acid, peptide, carbohydrate, cofactor, vitamins, xenobiotic, or lipid, or a salt or derivative thereof in an amount for example, >1%, ≥2%, ≥3%, ≥4%, ≥5%, ≥6%, ≥7%, ≥8%, ≥9%, ≥10%, ≥20%, ≥30%, ≥40%, ≥50%, ≥60%, ≥70%, ≥80%, ≥90%, ≥95%, or ≥98% of the composition. In some embodiments, the pharmaceutical composition can include a plurality of small molecule metabolites, such as one or more of an amino acid, peptide, carbohydrate, cofactor, vitamins, xenobiotic, and/or lipid described herein, or salts or derivatives thereof in, for example, >1%, ≥2%, ≥3%, ≥4%, ≥5%, ≥6%, ≥7%, ≥8%, ≥9%, ≥10%, ≥20%, ≥30%, ≥40%, ≥50%, ≥60%, ≥70%, ≥80%, ≥90%, ≥95%, or ≥98% of the composition.

Foodstuffs

Foodstuffs and other comestibles including a small molecule metabolite, such as an amino acid, peptide, carbohydrate, cofactor, vitamins, xenobiotic, or lipid described herein, or a salt or derivative thereof, are provided, wherein an amount of the small molecule metabolite in the foodstuff has been fortified (e.g., enriched or concentrated). A small molecule metabolite, such as an amino acid, peptide, carbohydrate, cofactor, vitamins, xenobiotic, or lipid, provided herein may be added to foodstuffs for consumption by a subject. The small molecule metabolite, such as an amino acid, peptide, carbohydrate, cofactor, vitamins, xenobiotic, or lipid described herein, may be integrated into one or more ingredients of a foodstuff. The small molecule metabolite, such as an amino acid, peptide, carbohydrate, cofactor, vitamins, xenobiotic, or lipid described herein, may be prepared as an ingredient, or may be unprepared. The compound, or preparation including the compound, may be added prior to preparation, during preparation, or following preparation. Preparation may without limitation include cooking, mixing, flavoring, seasoning, blending, boiling, frying, baking, or other processes known in the art. Fortification is preferably at a level so as to provide a therapeutic daily dosage of the small molecule metabolite as described elsewhere herein; however, beneficial effects may also be obtained at amounts below such dosages.

A small molecule metabolite, such as an amino acid, peptide, carbohydrate, cofactor, vitamins, xenobiotic, or lipid, or salt or derivative thereof, as provided herein may be present as a constituency in foodstuffs by operation of processes known in nature, for example, by altering the metabolic processes of a plant, animal, bacteria, or fungus. Genetic alteration of a plant, animal, bacteria, or fungus to increase the concentration of a small molecule metabolite, such as an amino acid, peptide, carbohydrate, cofactor, vitamins, xenobiotic, or lipid as described herein, or a salt or derivative thereof, is contemplated. By way of example, the small molecule metabolite can be present in the foodstuff in a concentration of at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, or higher, for example, 1% to 2% or 3% or 4% or 5% or 6% or 7% or 8% or 9% or 10% or 20% or 30% or 40% or 50%. The small molecule metabolite, if naturally present in a foodstuff, can be present in an enriched amount above that which is naturally occurring for the foodstuff, e.g., a concentration of 10% or more above the average or highest naturally occurring observed concentration, e.g., 20% or 30% or 40% or 50% or 100% or 200% or 300% or 400% or 1000% or 2000% or 5000% or more above the average or highest naturally occurring observed concentration.

Indications

Provided are compositions and methods for treating conditions that negatively impact longevity and the quality of aging, including but not limited to inflammation (including but not limited to inflammation of aging, obesity-associated inflammation, chronic low-lying inflammation, and autoimmune disorders (such as, for example Crohn disease, systemic lupus erythematosus, rheumatoid arthritis, psoriasis, type 1 diabetes, multiple sclerosis, and ulcerative colitis), hemolytic anemias (including but not limited to thalassemias, hereditary spherocytosis, hereditary elliptocytosis, glucose-6-phosphate dehydrogenase deficiency, pyruvate kinase deficiency, immune hemolytic anemia, alloimmune hemolytic anemia, drug-induced hemolytic anemia, mechanical hemolytic anemias, and paroxysmal nocturnal hemoglobinuria), anemia of chronic disease, anemia, aplastic anemias (including but not limited to congenital hypoplastic anemia, Diamond-Blackfan anemia and Fanconi anemia), iron deficiency anemia, anemias of abnormal RBC size (including but not limited to megaloblastic anemia and microcytic anemia), vitamin deficiency anemias (including but not limited to pernicious anemia) anemia of RBC mutation (including but not limited to thalassemia, sideroblastic anemia and sickle cell anemia), components of metabolic syndrome, including diabetes type II, obesity, pre-diabetes, glucose intolerance, gestational diabetes mellitus (GDM), impaired fasting glycemia (IFG), impaired adiponectin production, postprandial hyperglycemia, dyslipidemia, post prandial dyslipidemia, hyperlipidemia, hypertriglyceridemia, post hypertriglyceridemia, insulin resistance, polycystic ovary syndrome (PCOS), non-alcoholic fatty liver disease (NAFLD), non-alcoholic steatohepatitis (NASH), hypoinsulinemia, fatty liver disease, elevated glucose levels, elevated insulin levels, elevated LDL-cholesterol levels, elevated triglyceride levels, low HDL-cholesterol levels, and dysmetabolic iron overload syndrome (DIOS)), liver diseases, conditions with iron overload and/or hyperferritinemia (including but not limited to infection, neoplasm, chronic or acute inflammation, autoimmune diseases, DIOS and other iron overload and iron storage disorders, Still's disease, idiopathic arthritis, hemophagocytic lymphohistiocytosis, macrophage activation syndrome, liver conditions including NAFLD NASH, and hepatocellular carcinoma, anemia of chronic inflammation, and neurodegenerative diseases, including Alzheimer's disease and other forms of dementia), and delayed impaired skin integrity, delayed wound healing, and delayed scarring and impaired skin integrity, wound healing, and scarring (including delayed impaired skin integrity, wound healing, and scarring due to aging, obesity, chronic diseases, immunosuppression, nutritional status, burns, or vascular insufficiency), pain, allergies, sleep disorders and problems, and gastrointestinal disorders and problems.

Aging refers to a series of morphological and functional changes in an organism which take place over time. The term also refers to the deterioration of the biological functions after an organism has attained its maximum reproductive potential. It is thought that inflammation may be related to aging through mutation to mitochondrial DNA and other processes.

In some embodiments, the compositions and methods provided herein are indicated for treatment, prophylaxis, prevention or maintenance of aging-associated conditions, including hypercholesterolemia, obesity, thrombosis, fibrosis, impaired skin integrity, wound healing, scarring, hyperglobulinemia, hypersensitivity, cancer, pain, allergies, sleep disorders and problems, and gastrointestinal disorders and problems.

Without wishing to be limited by theory, it is thought that increasing odd chain saturated small molecule metabolite free small molecule metabolite or phospholipid levels in the serum, plasma, and cells to targeted concentrations may decrease aging-associated conditions.

In some embodiments, the methods provided herein increase levels of serum, plasma, or erythrocyte membrane odd chain small molecule metabolites.

In some embodiments, levels of serum, plasma, or erythrocyte membrane very long even chain small molecule metabolites may increase following administration of one or more odd chain small molecule metabolites, or a salt or derivative thereof.

In some embodiments, the condition treated is anemia of chronic disease.

In some embodiments, the condition treated is autoimmune disease.

In some embodiments, the compositions and methods provided herein modulate a marker of aging-associated conditions that impair longevity or quality of life. In certain embodiments, the marker is serum, plasma, or red blood cell membrane small molecule metabolite percentage; serum, plasma, or red blood cell membrane concentration of a small molecule metabolite contained herein; serum plasma, or red blood cell membrane total small molecule metabolite; cholesterol. In some embodiments, the small molecule metabolite is measured as a constituent of glycolipids. In further embodiments, the small molecule metabolite is measured as a constituent of phospholipids. In still further embodiments, the marker is serum or red blood cell membrane very long even chain small molecule metabolite percentage, serum concentration of a very long even chain small molecule metabolite, serum total very long even chain small molecule metabolites.

In some embodiments, the methods provided herein include the step of measuring the concentration of a marker of inflammation. One of skill in the art will be able to perform suitable methods for such measurements, including but not limited to those described herein.

Provided herein are methods for treating including the step of administering a dose of a small molecule metabolite, such as a small molecule metabolite or a very long even chain small molecule metabolite, at a predetermined interval, or at an interval left to the discretion of the subject.

In some embodiments, the compounds and methods provided herein may provide a threshold serum, plasma, or red blood cell membrane percentage of an small molecule metaboliterelative to all serum, plasma, or red blood cell membrane small molecule metabolites, respectively. For example, the threshold value may be a value of about 0.05% or lower to 90% or higher, e.g., a value of at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.1%, at least about 1.2%, at least about 1.3%, at least about 1.4%, at least about 1.5%, at least about 1.6%, at least about 1.7%, at least about 1.8%, at least about 1.9%, at least about 2.1%, at least about 2.2%, at least about 2.3%, at least about 2.4%, at least about 2.5%, at least about 2.6%, at least about 2.7%, at least about 2.8%, at least about 2.9%, at least about 3.0%, at least about 3.5%, at least about 4.0%, at least about 4.5%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or more than 90%.

In some embodiments, the compounds and methods provided herein may provide an increase above a baseline value (e.g., pretreatment value in a patient being treated, or general value observed in a particular patient population) in a serum or plasma concentration of an odd chain small molecule metabolite, or red blood cell membrane concentration of an odd chain small molecule metabolite. For example, a serum or plasma small molecule metabolite or red blood cell membrane concentration of an small molecule metabolite may be increased by at least about 1 μg/ml, at least about 2 μg/ml, at least about 3 μg/ml, at least about 4 μg/ml, at least about 5 μg/ml, at least about 6 μg/ml, at least about 7 μg/ml, at least about 8 μg/ml, at least about 9 μg/ml, at least about 10 μg/ml, at least about 15 μg/ml, at least about 20 μg/ml, at least about 25 μg/ml, at least about 30 μg/ml, at least about 35 μg/ml, at least about 40 μg/ml, at least about 45 μg/ml, at least about 50 μg/ml, or more than 50 μg/ml. In some embodiments, the serum concentration of an odd chain small molecule metabolite, or red blood cell membrane concentration of an small molecule metabolite may increase above a baseline value (e.g., pretreatment value in a patient being treated, or general value observed in a particular patient population) by at least about $0.01 \times 10^{-4}$ M, at least about $0.05 \times 10^{-4}$ M, at least about $0.1 \times 10^{-4}$ M, at least about $0.2 \times 10^{-4}$ M, at least about $0.3 \times 10^{-4}$ M, at least about $0.4 \times 10^{-4}$ M, at least about $0.5 \times 10^{-4}$ M, at least about $0.6 \times 10^{-4}$ M, at least about $0.7 \times 10^{-4}$ M, at least about $0.8 \times 10^{-4}$ M, at least about $0.9 \times 10^{-4}$ M, at least about $1 \times 10^{-4}$ M, at least about $2 \times 10^{-4}$ M, or at least about $3 \times 10^{-4}$ M.

In some embodiments, the compounds and methods provided herein may provide an increase in serum or plasma total odd chain small molecule metabolites, or red blood cell membrane total small molecule metabolites. For example, serum total odd chain small molecule metabolites, or red blood cell membrane total odd chain small molecule metabolites, may be increased above a baseline value (e.g., pretreatment value in a patient being treated, or general value observed in a particular patient population) by at least about 5 µg/ml, at least about 6 µg/ml, at least about 7 µg/ml, at least about 8 µg/ml, at least about 9 µg/ml, at least about 10 µg/ml, at least about 15 µg/ml, at least about 20 µg/ml, at least about 25 µg/ml, at least about 30 µg/ml, at least about 35 µg/ml, at least about 40 µg/ml, at least about 45 µg/ml, at least about 50 µg/ml, at least about 60 µg/ml, at least about 70 µg/ml, at least about 80 µg/ml, at least about 90 µg/ml, at least about 100 µg/ml, at least about 150 µg/ml, at least about 200 µg/ml, at least about 250 µg/ml, at least about 300 µg/ml, at least about 350 µg/ml, at least about 400 µg/ml, at least about 450 µg/ml, at least about 500 µg/ml, or more than 500 µg/ml.

In some embodiments, the compounds and methods provided herein may provide an increase above a baseline value (e.g., pretreatment value in a patient being treated, or general value observed in a particular patient population) in a serum, plasma, or red blood cell membrane odd chain small molecule metabolites relative to all serum or red blood cell membrane small molecule metabolites, respectively. For example, a serum, plasma, or red blood cell membrane small molecule metabolite may be increased above a baseline value (e.g., pretreatment value in a patient being treated, or general value observed in a particular patient population) by at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.1%, at least about 1.2%, at least about 1.3%, at least about 1.4%, at least about 1.5%, at least about 1.6%, at least about 1.7%, at least about 1.8%, at least about 1.9%, at least about 2%, at least about 2.1%, at least about 2.2%, at least about 2.3%, at least about 2.4%, at least about 2.5%, at least about 2.6%, at least about 2.7%, at least about 2.8%, at least about 2.9%, at least about 3%, at least about 3.5%, at least about 4%, at least about 4.5%, at least about 5%, or more than 5%.

In some embodiments, the compounds and methods provided herein may provide a reduction in elevated erythrocyte sedimentation rate.

In some embodiments, the compounds and methods provided herein may provide a reduction in elevated alkaline phosphatase.

In some embodiments, the compounds and methods provided herein may provide a reduction in serum ferritin. For example, serum ferritin may be reduced below a baseline value (e.g., pretreatment value in a patient being treated, or general value observed in a particular patient population) by at least about 10 ng/ml, at least about 100 ng/ml, at least about 200 ng/ml, at least about 300 ng/ml, at least about 400 ng/ml, at least about 500 ng/ml, at least about 600 ng/ml, at least about 700 ng/ml, at least about 800 ng/ml, at least about 900 ng/ml, at least about 1000 ng/ml, at least about 1100 ng/ml, at least about 1200 ng/ml, at least about 1300 ng/ml, at least about 1400 ng/ml, at least about 1500 ng/ml, at least about 2000 ng/ml, at least about 2500 ng/ml, at least about 3000 ng/ml, at least about 3500 ng/ml, at least about 4000 ng/ml, at least about 4500 ng/ml, at least about 5000 ng/ml, at least about 6000 ng/ml, at least about 7000 ng/ml, at least about 8000 ng/ml, at least about 9000 ng/ml, at least about 10000 ng/ml, or more than 10000 ng/ml.

In some embodiments, the compounds and methods provided herein may provide a reduction in serum ferritin below a specified level. For example, serum ferritin may be reduced below about 20000 ng/ml, about 15000 ng/ml, about 12000 ng/ml, about 10000 ng/ml, about 8000 ng/ml, about 5000 ng/ml, about 2000 ng/ml, about 1000 ng/ml, or about 500 ng In some embodiments, a small molecule metabolite is administered to maintain serum or plasma total percent of the odd chain small molecule metabolite, or all odd chain small molecule metabolites, above a predetermined threshold value. In variations of these embodiments, the small molecule metabolite is heptadecanoic acid. In further variations, the small molecule metabolite is administered to maintain serum phospholipid percent of the odd chain small molecule metabolite, or all odd chain small molecule metabolites, above about 0.1%, about 0.2%, about 0.3%, about 0.4%, about 0.5%, about 0.6%, about 0.7%, about 0.8%, about 0.9%, about 1%, about 1.2%, about 1.4%, about 1.6%, about 1.8%, about 2%, about 2.2%, about 2.4%, or about 2.6%.

In some embodiments, the compounds and methods provided herein may provide a threshold serum, plasma, or red blood cell membrane percentage of a very long even chain small molecule metabolite relative to all serum or red blood cell membrane small molecule metabolites, respectively. For example, the threshold value may be a value of about 0.05% or lower to 90% or higher, e.g., a value of at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.1%, at least about 1.2%, at least about 1.3%, at least about 1.4%, at least about 1.5%, at least about 1.6%, at least about 1.7%, at least about 1.8%, at least about 1.9%, at least about 2.1%, at least about 2.2%, at least about 2.3%, at least about 2.4%, at least about 2.5%, at least about 2.6%, at least about 2.7%, at least about 2.8%, at least about 2.9%, at least about 3.0%, at least about 3.5%, at least about 4.0%, at least about 4.5%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or more than 90%.

In some embodiments, the compounds and methods provided herein may provide an increase above a baseline value (e.g., pretreatment value in a patient being treated, or general value observed in a particular patient population) in a serum or plasma concentration of a small molecule metabolite, or red blood cell membrane concentration of a small molecule metabolite. For example, a serum very long even chain small molecule metabolite or red blood cell membrane concentration of a very long even chain small molecule metabolite may be increased by at least about 0.01 µg/ml, at least about 0.05 µg/ml, at least about 0.1 µg/ml, at least about 0.4 µg/ml, 1 µg/ml, at least about 2 µg/ml, at least about 3 µg/ml, at least about 4 µg/ml, at least about 5 µg/ml, at least about 6 µg/ml, at least about 7 µg/ml, at least about 8 µg/ml, at least about 9 µg/ml, at least about 10 µg/ml, at least about 15 µg/ml, at least about 20 µg/ml, at least about 25 µg/ml, at least about 30 µg/ml, at least about 35 µg/ml, at least about 40 µg/ml, at least about 45 µg/ml, at least about 50 µg/ml, or more than 50 µg/ml. In some embodiments, the serum concentration of a very long even chain small molecule metabolite, or red blood cell membrane concentration of a very long even chain small molecule metabolite may increase above a baseline value (e.g., pretreatment value in a patient being treated, or general value observed in a particular patient population) by at least about $0.001 \times 10^{-4}$ M, at least about $0.005 \times 10^{-4}$ M, at least about $0.05 \times 10^{-4}$ M, at least about $0.01 \times 10^{-4}$ M, at least about $0.05 \times 10^{-4}$ M, at least about $0.1 \times 10^{-4}$ M, at least about $0.2 \times 10^{-4}$ M, at least about $0.3 \times 10^{-4}$ M, at least about $0.4 \times 10^{-4}$ M, at least about $0.5 \times 10^{-4}$ M, at least about $0.6 \times 10^{-4}$ M, at least about $0.7 \times 10^{-4}$ M, at least about $0.8 \times 10^{-4}$ M, at least about $0.9 \times 10^{-4}$ M, at least about $1 \times 10^{-4}$ M, at least about $2 \times 10^{-4}$ M, or at least about $3 \times 10^{-4}$ M.

In some embodiments, the compounds and methods provided herein may provide an increase in serum or plasma total small molecule metabolites, or red blood cell membrane total small molecule metabolites. For example, serum total very long even chain small molecule metabolites, or red blood cell membrane total chain small molecule metabolites, may be increased above a baseline value (e.g., pretreatment value in a patient being treated, or general value observed in a particular patient population) by at least about 0.05 µg/ml, at least about 0.1 µg/ml, at least about 0.5 µg/ml, at least about 1 µg/ml, at least about 5 µg/ml, at least about 6 µg/ml, at least about 7 µg/ml, at least about 8 µg/ml, at least about 9 µg/ml, at least about 10 µg/ml, at least about 15 µg/ml, at least about 20 µg/ml, at least about 25 µg/ml, at least about 30 µg/ml, at least about 35 µg/ml, at least about 40 µg/ml, at least about 45 µg/ml, at least about 50 µg/ml, at least about 60 µg/ml, at least about 70 µg/ml, at least about 80 µg/ml, at least about 90 µg/ml, at least about 100 µg/ml, at least about 150 µg/ml, at least about 200 µg/ml, at least about 250 µg/ml, at least about 300 µg/ml, at least about 350 µg/ml, at least about 400 µg/ml, at least about 450 µg/ml, at least about 500 µg/ml, or more than 500 µg/ml.

In some embodiments, a composition or method provided herein may provide an increase in red blood cell count. For example, a red blood cell count level may be increased above a baseline value (e.g., pretreatment value in a patient being treated, or general value observed in a particular patient population) by at least about 0.1 cells/µL, at least about 0.2 cells/µL, at least about 0.3 cells/µL, at least about 0.4 cells/µL, at least about 0.5 cells/µL, at least about 0.6 cells/µL, at least about 0.7 cells/µL, at least about 0.8 cells/µL, at least about 0.9 cells/µL, at least about 1 cell/µL, at least about 1.2 cells/µL, at least about 1.4 cells/µL, at least about 1.6 cells/µL, or at least about 2 cells/µL.

Combination Therapies

In some embodiments, the compounds disclosed herein, such as a small molecule metabolite, or a salt or derivative thereof, or a very long even chain small molecule metabolite, or a salt or derivative thereof, or a pharmaceutical composition that includes a compound described herein, or a salt or derivative thereof, may be used in combination with one or more additional active agents. Examples of additional active agents that can be used in combination with a compound of an small molecule metabolite, or a salt or derivative thereof, or a composition that includes a compound of an small molecule metabolite, or a salt or derivative thereof, include, but are not limited to, agents currently used for treating conditions provided herein, and as otherwise known to medical science.

In some embodiments, a compound of an odd chain small molecule metabolite, or a salt or derivative thereof, or a composition that includes a compound of a small molecule metabolite, or a salt or derivative thereof, can be used with one, two, three or more additional active agents described herein. Such agents include, but are not limited to, a second small molecule metabolite, such as a small molecule metabolite, or a salt or derivative thereof.

In some embodiments, a compound of an small molecule metabolite, or a salt or derivative thereof, or a composition that includes a compound of a small molecule metabolite described herein, or a salt or derivative thereof, can be used (for example, administered or ingested) in combination with another agent or agents for treatment, prevention, maintenance, or prophylaxis of a condition provided herein including aging-associated conditions, including inflammation, anemia, hyperglycemia, dyslipidemia, hyperinsulinemia, liver disease, iron overload, impaired skin integrity, wound healing, scarring, pain, allergies, sleep disorders and problems, and gastrointestinal disorders and problems or for modulation of markers of the condition. In some embodiments, the condition can be inflammation (including but not limited to inflammation of aging, obesity-associated inflammation, chronic low-lying inflammation, and autoimmune disorders (such as, for example Crohn disease, systemic lupus erythematosus, rheumatoid arthritis, psoriasis, type 1 diabetes, multiple sclerosis, and ulcerative colitis), hemolytic anemias (including but not limited to thalassemias, hereditary spherocytosis, hereditary elliptocytosis, glucose-6-phosphate dehydrogenase deficiency, pyruvate kinase deficiency, immune hemolytic anemia, alloimmune hemolytic anemia, drug-induced hemolytic anemia, mechanical hemolytic anemias, and paroxysmal nocturnal hemoglobinuria), anemia of chronic disease, anemia, aplastic anemias (including but not limited to congenital hypoplastic anemia, Diamond-Blackfan anemia and Fanconi anemia), iron deficiency anemia, anemias of abnormal RBC size (including but not limited to megaloblastic anemia and microcytic anemia), vitamin deficiency anemias (including but not limited to pernicious anemia) anemia of RBC mutation (including but not limited to thalassemia, sideroblastic anemia and sickle cell anemia), components of metabolic syndrome, including diabetes type II, obesity, pre-diabetes, glucose intolerance, gestational diabetes mellitus (GDM), impaired fasting glycemia (IFG), impaired adiponectin production, postprandial hyperglycemia, dyslipidemia, post prandial dyslipidemia, hyperlipidemia, hypertriglyceridemia, post hypertriglyceridemia, insulin resistance, polycystic ovary syndrome (PCOS), non-alcoholic fatty liver disease (NAFLD), non-alcoholic steatohepatitis (NASH), hypoinsulinemia, fatty liver disease, elevated glucose levels, elevated insulin levels, elevated LDL-cholesterol levels, elevated triglyceride levels, low HDL-cholesterol levels, and dysmetabolic iron overload syndrome (DIOS)), liver diseases, conditions with iron overload and/or hyperferritinemia (including but not limited to infection, neoplasm, chronic or acute inflammation, autoimmune diseases, DIOS and other iron overload and iron storage disorders, Still's disease, idiopathic arthritis, hemophagocytic lymphohistiocytosis, macrophage activation syndrome, liver conditions including NAFLD NASH, and hepatocellular carcinoma, anemia of chronic inflammation, and neurodegenerative diseases, including Alzheimer's disease and other forms of dementia), and delayed impaired skin integrity, delayed wound healing, delayed scarring, and impaired skin integrity, wound healing, scarring (including delayed impaired skin integrity, wound healing, and scarring due to aging, obesity, chronic diseases, immunosuppression, nutritional status, burns, or vascular insufficiency), pain, allergies, sleep disorders and problems, and gastrointestinal disorders and problems. For example, a compound of a small molecule metabolite, such as a small molecule metabolite disclosed herein can be used in combination with one or more agents selected from iron chelators, albiglutide, aleglitazar, balaglitazone, canagliflozin, CJ-30001 (CJ Cheiljedang Corporation), CJ-30002 (CJ Cheiljedang Corporation), Diamyd® (glutamic acid decarboxylase (rhGAD65)), dulaglutide, exendin 4, gemigliptin, lixisenatide, lobeglitazone, shengke I (Tibet Pharmaceuticals), SK-0403 (Sanwa Kagaku Kenkyusho), teneligliptin, teplizumab, tofogliflozin, acarbose, alogliptin benzoate, chlorpropamide, Diab II (Biotech Holdings), exenatide, glibenclamide, gliclazide, glimepiride, glipizide, gliquidone, glisentide, glisolamide, HL-002 (HanAll Biopharma), insulin (human), insulin, insulin analogue (Eli Lilly®), insulin aspart, insulin detemir, insulin glargine, insulin lispro, Janumet®, linagliptin, liraglutide, metformin, miglitol, mitiglinide, nateglinide, Novo Mix 30® (Novo Nordisk®) pioglitazone, pramlintide, repaglinide, rosiglitazone maleate, saxagliptin, sitagliptin, Tresiba, tolazamide, tolbutamide, vildagliptin, voglibose, bezafibrate, diflunisal, cinnamic acid, carbutamide, glyburide (glibenclamide), glibomuride, glyhexamide, phenbutamide, and tolcyclamide or with one or more agents selected from a class of agents, where the classes include sulfonylureas, non-sulfonylurea secretagogues, glucagon-like peptides, exendin-4 polypeptides, beta 3 adrenoceptor agonists, PPAR agonists, dipeptidyl peptidase IV inhibitors, biguanides, alpha-glucosidase inhibitors, immunomodulators, statins and statin-containing combinations, angiotensin converting enzyme inhibitors, adeno sine A1 receptor agonists, adenosine A2 receptor agonists, aldosterone antagonists, alpha 1 adrenoceptor antagonists, alpha 2 adrenoceptor agonists, alpha 2 adrenoceptor agonists, angiotensin receptor antagonists, antioxidants, ATPase inhibitors, atrial peptide agonists, beta adrenoceptor antagonists, calcium channel agonists, calcium channel antagonists, diguanides, diuretics, dopamine D1 receptor agonists, endopeptidase inhibitors, endothelin receptor antagonists, guanylate cyclase stimulants, phosphodiderivativease V inhibitors, protein kinase inhibitors, Cdc2 kinase inhibitors, renin inhibitors, thromboxane synthase inhibitors, vasopeptidase inhibitors, vasopressin I antagonists, vasopressin 2 antagonists, angiogenesis inhibitors, advanced glycation end product inhibitors, bile acid binding agents, bile acid transport inhibitors, bone formation stimulants, apolipoprotein A1 agonists, DNA topoisomerase inhibitors, cholesterol absorption inhibitors, cholesterol antagonists, cholderivativeyl derivative transfer protein antagonists, cytokine synthesis inhibitors, DNA polymerase inhibitors, dopamine D2 receptor agonists, endothelin receptor antagonists, growth hormone antagonists, insulin sensitizers, lipase inhibitors, lipid peroxidation inhibitors, lipoprotein A antagonists, microsomal transport protein inhibitors, microsomal triglyceride transfer protein inhibitors, nitric oxide synthase inhibitors, oxidizing agents, phospholipase A2 inhibitors, radical formation agonists, platelet aggregation antagonists, prostaglandin synthase stimulants, reverse cholesterol transport activators, rho kinase inhibitors, selective estrogen receptor modulators, squalene epoxidase inhibitors, squalene synthase inhibitors, thromboxane A2 antagonists, amylin agonists, cannabinoid receptor antagonists, cholecystokinin A agonists, corticotropin-releasing factor agonists, dopamine uptake inhibitors, G protein-coupled receptor modulators, glutamate antagonists, glucagon-like peptide-1 agonists lipase inhibitors, melanin-concentrating hormone receptor antagonists, nerve growth factor agonists, neuropeptide Y agonists, neuropeptide Y antagonists, SNRIs, protein tyrosine phosphatase inhibitors, serotonin 2C receptor agonists, or with other agents such as central nervous system agents that affect neurotransmitters or neural ion channels, including antidepressants (bupropion), noradrenalin reuptake inhibitors (GW320659), selective serotonin 2c receptor agonists, selective 5HT 2c receptor agonists, antiseizure agents (topiramate, zonisamide), dopamine antagonists, cannabinoid-1 receptor antagonists (CB-1 receptor antagonists) (rimonabant); leptin/insulin/central nervous system pathway agents, including leptin analogues, leptin transport and/or leptin receptor promoters, ciliary neurotrophic factor (Axokine), neuropeptide Y and agouti-related peptide antagonists, pro-opiomelanocortin and cocaine and amphetamine regulated transcript promoters, α-melanocyte-stimulating hormone analogues, melanocoritin-4 receptor agonists, and agents that affect insulin metabolism/activity, which include protein-tyrosine phosphatase-IB inhibitors, peroxisome proliferator activated receptor-.gamma. receptor antagonists, short-acting bromocriptine (ergoset), somatostatin agonists (octreotide), and adiponectin/Acrp30 (Famoxin or Small molecule metabolite Metabolic Oxidation Inducer); gastrointestinal-neural pathway agents, including those that increase cholecystokinin activity (CCK), PYY activity, NPY activity, and PP activity, increase glucagon-like peptide-1 activity (exendin 4, dipeptidyl peptidase IV inhibitors), and those that decrease ghrelin activity, as well as amylin analogues (pramlintide); agents that may increase resting metabolic rate (selective β-3 stimulators/agonist, uncoupling protein homologues, and thyroid receptor agonists); other more diverse agents, including melanin concentrating hormone antagonists, phytostanol analogues, functional oils, P57, amylase inhibitors, growth hormone fragments, synthetic analogues of dehydroepiandrosterone sulfate, antagonists of adipocyte 11B-hydroxysteroid dehydrogenase type 1 activity, corticotropin-releasing hormone agonists, inhibitors of small molecule metabolite synthesis (cerulenin and C75), carboxypeptidase inhibitors, indanone/indanols, aminosterols (trodusquemine/trodulamine), and other gastrointestinal lipase inhibitors (ATL962); amphetamines, such as dextroamphetamine; other sympathomimetic adrenergic agents, including phentermine, benzphetamine, phendimetrazine, mazindol, and diethylpropion; or with one or more agents selected from ecopipam; oxyntomodulin (OM); inhibitors of glucose-dependent insulinotropic polypeptide (GIP); gastrin-releasing peptide; neuromedin B; enterostatin; amfebutamone, SR-58611; CP-045598; AOD-0604; QC-BT16; rGLP-1; 1426 (HMR-1426); N-5984; ISIS-1 13715; solabegron; SR-147778; Org-34517; melanotan-II; cetilistat; c-2735; c-5093; c-2624; APD-356; radafaxine; fluasterone; GP-389255; 856464; S-2367; AVE-1625; T-71; oleoyl-estrone; peptide YY [3-36] intranasal; androgen receptor agonists; PYY 3-36; DOV-102677; tagatose; SLV-319; 1954 (Aventis Pharma AG); oxyntomodulin, Thiakis; bromocriptine, PLIVA; diabetes/hyperlipidemia therapy, Yissum; CKD-502; thyroid receptor beta agonists; beta-3 adrenoceptor agonist; CDK-A agonists; galanin antagonist; dopamine D1 D2 agonists; melanocortin modulators; verongamine; neuropeptide Y antagonists; melanin-concentrating hormone receptor antagonists; dual PPAR alpha/gamma agonists; CGEN-P-4; kinase inhibitors; human MCH receptor antagonists; GHS-R antagonists; ghrelin receptor agonists; DG70 inhibitors; cotinine; CRF-BP inhibitors; urocortin agonists; UCL-2000; impentamine; β-3 adrenergic receptor; pentapeptide MC4 agonists; trodusquemine; GT-2016; C-75; CPOP; MCH-1 receptor antagonists; RED-103004; aminosterols; orexin-1 antagonists; neuropeptide Y5 receptor antagonists; DRF-4158; PT-15; PTPase inhibitors; A37215; SA-0204; glycolipid metabolites; MC-4 agonist; produlestan; PTP-1B inhibitors; GT-2394; neuropeptide Y5 antagonists; melanocortin receptor modulators; MLN-4760; PPAR gamma/delta dual agonists; NPYSRA-972; 5-HT2C receptor agonist; neuropeptide Y5 receptor antagonists (phenyl urea analogs); AGRP/MC4 antagonists; neuropeptide Y5 antagonists (benzimidazole); glucocorticoid antagonists; MCHR1 antagonists; Acetyl-CoA carboxylase inhibitors; R-1496; HOB 1 modulators; NOX-B11; peptide YY 3-36 (eligen); 5-HT 1 modulators; pancreatic lipase inhibitors; GRC-1087; CB-1 antagonists; MCH-1 antagonists; LY-448100; bombesin BRS3 agonists; ghrelin antagonists; MC4 antagonists; stearoyl-CoA desaturase modulators; PPAR pan agonists; EP-01492; hormone-sensitive lipase inhibitors; small molecule metabolite-binding protein 4 inhibitors; thiolactone derivatives; protein tyrosine phosphatase IB inhibitors; MCH-1 antagonist; P-64; PPAR gamma ligands; melanin concentrating hormone antagonists; thiazole gastroprokinetics; PA-452; T-226296; A-331440; immunodrug vaccines; diabetes/obesity therapeutics (Bioagency, Biofrontera Discovery GmbH); P-7 (Genfit); DT-011 M; PTP1B inhibitor; anti-diabetic peptide conjugates; KATP agonists; obesity therapeutics (Lexicon); 5-HT2 agonists; MCH-1 receptor antagonists; GMAD-1/GMAD-2; STG-a-MD; angiogenesis inhibitors; G protein-coupled receptor agonists; nicotinic therapeutics (ChemGenex); anti-obesity agents (Abbott); melanin concentrating hormone; GW-594884A; MC-4R agonist; histamine H3 antagonists; orphan GPCR modulators; MITO-3108; NLC-002; HE-2300; IGF/BBP-2-13; 5-HT2C agonists; ML-22952; neuropeptide Y receptor antagonists; AZ-40140; anti-obesity therapy (Nisshin Flour); GNTI; melanocortin receptor modulators; alpha-amylase inhibitors; beta-3 adrenoceptor agonists; ob gene products (Eli Lilly & Co.); SWR-0342-SA; SWR-0335; SP-18904; oral insulin mimetics; obesity therapeutics (7TM Pharma); beta-hydroxysteroid dehydrogenase (HSD) inhibitors; QRX-431; E-6776; RI-450; melanocortin-4 antagonists; melanocortin 4 receptor agonists; obesity therapeutics (CuraGen); leptin mimetics; A-74498; second-generation leptin; NBI-103; CL-314698; CP-114271; beta-3 adrenoceptor agonists; NMI-8739; UCL-1283; BMS-192548; CP-94253; PD-160170; nicotinic agonist; LG-100754; SB-226552; LY-355124; CKD-711; L-751250; PPAR inhibitors; G-protein therapeutics; obesity therapy (Amylin Pharmaceuticals Inc.); BW-1229; monoclonal antibody (ObeSys/CAT); L-742791; (5)-sibutramine; MBU-23; YM-268; BTS-78050; tubby-like protein genes; genomics (eating disorders; Allelix/Lilly); MS-706; GI-264879A; GW-409890; FR-79620 analogs; obesity therapy (Hybrigenics SA); ICI-198157; ESP-A; 5-HT2C agonists; PD-170292; AIT-202; LG-100641; GI-181771; anti-obesity therapeutics (Genzyme); leptin modulator; GHRH mimetics; obesity therapy (Yamanouchi Pharmaceutical Co. Ltd.); SB-251023; CP-331684; BIBO-3304; cholesten-3-ones; LY-362884; BRL-48962; PY-1 antagonists; A-71378; .RTM.-didesmethylsibutramine; obesity therapeutics (Bristol-Myers Squibb Co.); obesity therapeutics (Ligand Pharmaceuticals Inc.); LY-226936; NPY antagonists; CCK-A agonists; FPL-14294; PD-145942; ZA-7114; CL-316243; SR-58878; R-1065; BDBP-3226; HP-228; talibegron; FR-165914; AZM-008; AZM-016; AZM-120; AZM-090; AZM-131; AZM-132; AZM-134; AZM-127; AZM-083; AZM-1 15; AZM-140; vomeropherin; BMS-187257; D-3800; gene discovery (Axys/Glaxo); BRL-26830A; SX-013; ERR modulators; adipsin; AC-253; A-71623; A-68552; BMS-210285; TAK-677; MPV-1743; obesity therapeutics (Modex); GI-248573; exopipam; SSR-125180; obesity therapeutics (Melacure Therapeutics AB); BRL-35135; SR-146131; P-57; CGP-71583A; RF-1051; BMS-196085; manifaxine; DMNJ (Korea Research Institute of Bioscience and Biotechnology); BVT-5182; LY-255582; SNX-024; galanin antagonists; neurokinin-3 antagonists; dexfenfluramine; mazindol; diethylpropion; phendimetrazine; benzphetamine; amfebutmone; sertraline; AOD-9604; ATL-062; BVT-933; GT389-255; SLV319; HE-2500; PEG-axokine; L-796568; and ABT-239; rimonabant, sibutramine, orlistat, PYY or an analog thereof, CB-1 antagonist, leptin, phentermine, and exendin analogs; GPR1 19 agonists (e.g., anandamide; AR-231, 453; MBX-2982; Oleoylethanolamide; PSN-365,963; PSN-632,408; palmitoylethanolamide); GPR120 agonists; GPR 40 agonists; and SGLT2 inhibitors.

Additionally, a small molecule metabolite or salt or derivative as provided herein can be used in combination with one or more agents selected from Altoprev (lovastatin), Crestor (rosuvastatin), Lescol (fluvastatin), Lipitor (atorvastatin), Livalo (pitavastatin), Pravachol (pravastatin), Zocor (simvastatin), an anti-platelet medication, a beta blocker, an ACE inhibitor, a calcium channel blocker, a diuretic, anticoagulants, aspirin, bile acid sequestrants, Ezetimibe, Fibrates, Glycoprotein IIb/IIIa Receptor Inhibitors, Niacin (Nicotinic Acid), Nitrates, Platelet Inhibitors, Thrombolytics, lisinopril oral, atenolol oral, Bystolic oral, Diovan oral, hydrochlorothiazide oral, metoprolol succinate oral, amlodipine oral, Norvasc oral, Toprol XL oral, Benicar oral, metoprolol tartrate oral, losartan oral, lisinopril-hydrochlorothiazide oral, clonidine HCl oral, Diovan HCT oral, Cozaar oral, propranolol oral, spironolactone oral, Azor oral, carvedilol oral, Coreg oral, Benicar HCT oral, Exforge oral, Avapro oral, Lotrel oral, verapamil oral, furosemide oral, Lasix oral, Hyzaar oral, Tekturna oral, enalapril maleate oral, Micardis oral, losartan-hydrochlorothiazide oral, ramipril oral, Lopressor oral, Altace oral, Micardis HCT oral, Avalide oral, diltiazem oral, triamterene-hydrochlorothiazide oral, labetalol oral, terazosin oral, amlodipine-benazepril oral, hydralazine oral, Atacand oral, benazepril oral, Tribenzor oral, triamterene oral, doxazosin oral, nifedipine oral, Ziac oral, Aldactone oral, Maxzide oral, Cartia XT oral, prazosin oral, Cardizem CD oral, Zestril oral, Dyazide oral, bisoprolol fumarate oral, Tenex oral, Tenormin oral, Coreg CR oral, Prinivil oral, valsartan oral, atenolol-chlorthalidone oral, Edarbyclor oral, benazepril-hydrochlorothiazide oral, ferrous sulfate oral, Ferrlecit intravenous, Feraheme intravenous, Feosol oral, Infed injection, Integra oral, Ferrex 150 Forte oral, Tandem Dual Action oral, Ferrex 150 oral, ferrous gluconate oral, Corvite 150 oral, Integra F oral, NovaFerrum oral, Iron (ferrous sulfate) oral, Vitron-C oral, Folic acid, corticosteroids, rituximab, IVIG, prednisone, methylprednisolone oral, Kenalog injection, Medrol (Pak) oral, Medrol oral, dexamethasone oral, Depo-Medrol injection, prednisolone oral, DexPak 13 Day oral, Solu-Medrol intravenous, hydrocortisone oral, Cortef oral, Deltasone oral, triamcinolone acetonide injection, cortisone oral, cholinesterase inhibitors such as Donepezil (Aricept), Rivastigmine (Exelon), and Galantamine (Razadyne), Memantine, Aricept, Namenda, Namenda XR, Razadyne ER, Alpha E, vitamin E, Hydergine, Namzaric, Dopamine Agonists such as pramipexole (Mirapex), ropinirole (Requip), rotigotine (Neupro patch) and apomorphine (Apokyn), Anticholinergics such as benztropine (Cogentin) and trihexyphenidyl, MAO-B Inhibitors such as (Eldepryl, Zelapar) and rasagiline (Azilect), COMT Inhibitors such as Entacapone (Comtan), Carbidopa/Levodopa (Sinemet®), amantadine, Tetrabenazine (Xenazine), haloperidol (Haldol), chlorpromazine, risperidone (Risperdal), quetiapine (Seroquel), olanzapine (Zyprexa), indomethacin, sulindac, etodolac, mefenamic acid, meclofenamic acid, meclofenamate sodium, flufenamic acid, tolmetin, ketorolac, diclofenac, diclofenac sodium, ibuprofen, naproxen, naproxen sodium, fenoprofen, ketoprofen, flurbiprofen, oxaprozin piroxicam, meloxicam, ampiroxicam, droxicam, lornoxicam, cinnoxicam, sudoxicam, and tenoxicam.

Additionally, a compound of a small molecule metabolite disclosed herein can be used in combination with one or more agents selected from iron dextran, iron sumalate, polysaccharide iron, ferrus fumarate, carbonyl iron, ferrous asparto glycinate, heme iron polypeptide can be sometimes indicated, ferrus bisglycinate as can be the administration of other medicaments such as androgen hormones, such as erythropoietin, folic acid, vitamin B12, vitamin C, succinic acid, niacin, pyridoxine, riboflavin, biotin, thiamine, calcium formate, Aminoxin, Anadrol-50, Chromagen Forte, Epoetin alfa, Epogen, Fe C Tab Plus, FeRiva, FeRivaFA, Ferocon, Ferotrin, Ferralet 90, Ferrex 28, Ferrogels Forte, FoliTab 500, Fumatinic, Hematogen Forte, Hemetab, Integra Plus, Irospan 42/6, Lenalidomide, Maxaron Forte, Myferon 150 Forte, MyKidz Iron, NovaFerrum, Oxymetholone, Procrit, Proferrin-Forte, Pyridoxine, Repliva 21/7, Revlimid, and Tricon.

Dosing

As will be readily apparent to one skilled in the art, the useful in vivo dosage to be administered and the particular mode of administration will vary depending upon the age, weight, the severity of the condition, and mammalian species treated, the particular forms of the compounds employed, and the specific use for which these compounds are employed. The determination of effective dosage levels, that is the dosage levels necessary to achieve the desired result, can be accomplished by one skilled in the art using routine methods, for example, in vivo studies. Reference may be made to, for example, "Estimating the Maximum Safe Starting Dose in Initial Clinical Trials for Therapeutics in Adult Healthy Volunteers," U.S. Food and Drug Administration, July 2005.

In some embodiments, a method provided herein may comprise administering a therapeutically effective amount of a composition provided herein. In some embodiments, a therapeutically effective amount may be determined by reference to the modulation of a marker of a condition provided herein including inflammation, anemia, hyperglycemia, dyslipidemia, hyperinsulinemia, liver disease, iron overload, impaired skin integrity, wound healing, scarring, pain, allergies, sleep disorders and problems, and gastrointestinal disorders and problems. In some embodiments, a therapeutically effective amount may be determined by reference to the modulation of a symptom of a condition provided herein. In still other embodiments, reference may be made to established guidelines for the conditions described herein, including, but not limited to, guidelines for the treatment of a condition provided herein including inflammation.

The dosage may vary broadly, depending upon the desired effects and the therapeutic indication, such as marker values. Alternatively, dosages may be based and calculated upon the surface area or weight of the patient, as understood by those of skill in the art. The exact dosage will be determined on a case-by-case basis, or, in some cases, will be left to the informed discretion of the subject. The daily dosage regimen for an adult human patient may be, for example, an oral dose of a small molecule metabolite, such as an small molecule metabolite or a very long even chain small molecule metabolite, or a salt or derivative thereof, or a mixture of a plurality of small molecule metabolites, or a salt or derivative thereof, from about 0.01 mg to about 10000 mg, from about 1 mg to about 5000 mg, from about 5 mg to about 2000 mg, from about 10 mg to about 1000 mg, or from about 50 mg to about 500 mg. A single dose may include a small molecule metabolite, or a salt or derivative thereof, in about 0.01 mg, about 0.1 mg, about 1 mg, about 5 mg, about 10 mg, about 20 mg, about 50 mg, about 100 mg, about 200 mg, about 300 mg, about 400 mg, about 500 mg, about 600 mg, about 800 mg, about 900 mg, about 1000 mg, about 2000 mg, about 5000 mg, or more. The dosage may be adjusted according to the body mass of the subject, for example, the dosage may be about 0.001 mg/kg, about 0.01 mg/kg, about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 15 mg/kg, about 20 mg/kg, about 25 mg/kg, about 30 mg/kg, or higher. The dosage may be a single one or a series of two or more given in the course of one or more days, as is appropriate for the individual subject. In some embodiments, the compounds will be administered for a period of continuous therapy, for example for about a week or more (e.g., one week, two weeks, three weeks, four weeks, five weeks, six weeks, seven weeks, eight weeks, or more), for several weeks, for about a month or more (e.g., one month, two months, three months, four months, five months, six months, seven months, eight months, nine months, ten months, eleven months, twelve months, or more), for about a year or more, or for a plurality of years. In some embodiments, a small molecule metabolite, such as an small molecule metabolite or a very long even chain small molecule metabolite, or a salt or derivative thereof, can be administered or ingested one time per day, two times per day, three times per day, or more.

As will be understood by those of skill in the art, in certain situations it may be necessary to administer the compounds disclosed herein in amounts that exceed the above-stated, preferred dosage range in order to effectively treat a subject.

Unit dosage forms can also be provided, e.g., individual packages with a premeasured amount of the composition, configured for administration on a predetermined schedule. Unit dosage forms configured for administration one to three times a day are preferred; however, in certain embodiments it may be desirable to configure the unit dosage form for administration more than three times a day, or less than one time per day.

Dosage amount and interval may be adjusted to the individual subject to provide plasma levels of the active moiety which are sufficient to maintain predetermined parameters, indicators, or marker values, or minimal effective concentration (MEC). Dosages necessary to achieve the desired result will depend on individual characteristics and route of administration. However, assays, for example, HPLC assays or bioassays, may be used to determine serum concentrations.

In some embodiments, the compounds and methods provided herein may be used in conjunction with devices and methods of using devices, for example, as provided in U.S.

Pat. Nos. 7,651,845; 8,251,904; 8,251,904; 4,985,015; 8,827,957; 4,252,159; 5,318,521; 4,718,430; 9,713,600, 9,707,199, 9,687,461, 9,662,306, 9,561,206, U.S. Publ. No. 2011/0190702; U.S. Publ. No. 2017/0266144, U.S. Publ. No. 2016/0324814, U.S. Publ. No. 2016/0195559, U.S. Publ. No. 2016/0195558, U.S. Publ. No. 2016/0193172, 2 U.S. Publ. No. 016/0193171, U.S. Publ. No. 2016/0193170, WO 2016/111843, DE 2615061; and in conjunction with diagnostic devices, for example, as provided in U.S. Publ. No. 2012/0072236. The contents of each of the foregoing patent documents is incorporated herein by reference in its entirety.

Diagnosis and Monitoring

Provided herein are methods for the diagnosis and monitoring of conditions provided herein including inflammation.

In some embodiments, the method of diagnosis or monitoring may comprise the step of measuring a percentage of a small molecule metabolite, such as an amino acid, peptide, carbohydrate, cofactor and vitamin, xenobiotic, or lipid as described herein, in a bodily fluid. In some embodiments, the method of diagnosis or monitoring may comprise the step of measuring a marker of a condition provided herein including inflammation in a subject. In some embodiments, the method of diagnosis or monitoring may comprise the step of measuring a marker of anemia of chronic disease. In some embodiments, a correlation between one marker and another may prove instructive. In some embodiments, inflammation or a related condition may be diagnosed by reference to a threshold level of erythrocyte sedimentation rate, for example, or serum small molecule metabolite or serum very long even chain small molecule metabolite. In some embodiments, a condition provided herein including inflammation may be diagnosed by reference to a threshold level of a marker of the condition, for example, serum small molecule metabolite percentage, serum concentration of a small molecule metabolite, serum total small molecule metabolite, serum small molecule metabolite, serum total very long even chain small molecule metabolites, or a ratio between two serum small molecule metabolites. For example, the threshold may be determined by reference to a symptom or marker of a condition provided herein including inflammation. For example, the condition can be metabolic syndrome.

The percentage of a small molecule metabolite, such as an small molecule metabolite or a very long even chain small molecule metabolite, or a marker of a condition provided herein including inflammation, in a subject may be monitored by any means. Samples for analysis may be derived any fluid or tissue of the subject. For example, from serum, plasma, erythrocyte membranes, urine, and feces.

EXAMPLES

Example 1

Small molecule metabolites can serve as biomarkers, therapeutic targets, natural supplements, or therapeutics. The most promising metabolites are expected to 1) be detectable in blood, 2) have demonstrable differences between case and control populations, 3) have the ability to increase in concentration with interventions, and 4) have these increased levels correlated with clinical benefits. It was hypothesized that small molecule metabolite biomarkers, therapeutic targets, natural supplements, and therapeutics could be discovered by identifying metabolites that met at least three of four of the criteria above, using samples from bottlenose dolphin populations.

Bottlenose dolphins (Tursiops truncatus) are large-brained, long-lived mammals that develop aging-associated conditions similar to humans, including inflammation, anemia, hyperglycemia, dyslipidemia, hyperinsulinemia, liver disease, and iron overload (Venn-Watson S (2013) Blood-based indicators of insulin resistance and metabolic syndrome in bottlenose dolphins (Tursiops truncatus). Frontiers Endo 4:136, Venn-Watson S (2013) Associations of ceruloplasmin and haptoglobin with inflammation and glucose in bottlenose dolphins (Tursiops truncatus) J Comp Clin Path DOI: 10.1007/s00580-013-1738-0, Venn-Watson S (2012) Hemochromatosis and fatty change: building evidence for insulin resistance in bottlenose dolphins (Tursiops truncatus). J Zoo Wildlf Med 43:S35-S47, Venn-Watson S (2011) Physiology of aging among healthy, older bottlenose dolphins (Tursiops truncatus): comparisons with aging humans. J Comp Phys B 181:667-680, Venn-Watson S (2008) Clinical relevance of elevated transaminases in a bottlenose dolphin (Tursiops truncatus) population. J Wildlf Dis 44: 318-330). For over 60 years, the U.S. Navy has cared for a population of approximately 100 dolphins. While the average lifespan of dolphins in the wild is 20 years, Navy dolphins on average live 32 years, more than fifty percent longer than wild dolphins. Approximately one-third of Navy dolphins are between 30 to 50 years old. Due in part to these populations' age differences, Navy dolphins have higher mean glucose, cholesterol, triglycerides, GGT, insulin, iron, and ferritin levels compared to wild dolphins living in Sarasota Bay, Florida.

In addition to differences in mean age, Navy and wild dolphins ingest different fish-based diets. Historically, Navy dolphins have been fed a diet of small, low-fat species, such as capelin and squid. Wild dolphins in Sarasota Bay ingest a large variety of fish, including larger, high-fat species, such as mullet and pinfish. It has been previously demonstrated that feeding Navy dolphins a modified diet resembling that of wild dolphins resulted in improved clinical indices of aging-associated conditions, including lowered ferritin and normalized glucose, insulin, and triglycerides.

Routine, fasted serum samples collected throughout 26 Navy dolphins' lifespans and archived at −80° C. were submitted for global metabolomics and complex lipid profiling. The sample set targeted one sample for each dolphin's year of life, resulting in 355 samples for the study with paired clinical pathology data. In addition, single serum samples from 38 wild dolphins living in Sarasota Bay, Florida were included in the sample set.

Navy dolphins were categorized based on the presence or absence of the following criteria during the most recent year of life (if alive) or during the year preceding death (if dead): at least 50% of routine and fasted blood samples with elevated glucose (greater than 95 mg/dl), elevated cholesterol (greater than 250 mg/dl), elevated triglycerides (greater than 137 mg/dl), elevated erythrocyte sedimentation rate (greater than 19 mm/hr), elevated liver enzymes (ALT, AST, or GGT levels greater than 41, 255, and 31 U/L respectively), or elevated iron (greater than 300 µg/dl). Animals were categorized as Early Cases (presence of two or three of the criteria), Advanced Cases (presence of more than three criteria), and Controls (presence of one or less of the criteria). Wild dolphins were considered a second Control group.

Serum samples were analyzed for small molecules using global metabolomics and complex lipid profiling. Briefly, serum extracts were prepared and analyzed using three methods: ultrahigh performance liquid chromatography-tandem mass spectroscopy (UPLC-MS/MS) with positive ion mode electrospray ionization (ESI), UPLC-MS/MS with negative ion mode ESI, and hydrophilic interaction liquid chromatography (UPLC-MS/MS).

The informatics system consisted of four major components, the Laboratory Information Management System (LIMS), the data extraction and peak-identification software, data processing tools for QC and compound identification, and a collection of information interpretation and visualization tools for use by data analysts. The hardware and software foundations for these informatics components were the LAN backbone, and a database server running Oracle 10.2.0.1 Enterprise Edition.

Raw data were extracted, peak-identified and QC processed using proprietary hardware and software. Compounds were identified by comparison to library entries of purified standards or recurrent unknown entities. Biochemical identifications were based on three criteria: retention index within a narrow RI window of the proposed identification, accurate mass match to the library +/−10 ppm, and the MS/MS forward and reverse scores between the experimental data and authentic standards. Peaks were quantified using area-under-the-curve. A data normalization step was performed to correct variation resulting from instrument inter-day tuning differences.

Serum samples were also analyzed for complex lipids. Briefly, lipids were extracted from samples in methanol: dichloromethane in the presence of internal standards. The extracts were concentrated under nitrogen and reconstituted in 0.25 mL of 10 mM ammonium acetate dichloromethane: methanol (50:50). The extracts were transferred to inserts and placed in vials for infusion-MS analysis, performed on a Shimazdu LC with nano PEEK tubing and the Sciex Selexlon-5500 QTRAP. The samples were analyzed via both positive and negative mode electrospray. The 5500 QTRAP scan was performed in MRM mode with the total of more than 1,100 MRMs. Individual lipid species were quantified by taking the peak area ratios of target compounds and their assigned internal standards, then multiplying by the concentration of internal standard added to the sample. Lipid class concentrations were calculated from the sum of all molecular species within a class, and small molecule metabolite compositions were determined by calculating the proportion of each class comprised by individual small molecule metabolites.

Several statistical models were used to identify targeted biochemicals. Welch's two-sample t-Tests were performed to compare metabolite quantities between Navy dolphins and wild dolphins. Table 1 summarizes small molecule metabolites that were significantly higher in wild dolphins compared to Navy dolphins.

TABLE 1

| Small molecule metabolites | Ratio of serum-based levels in wild versus Navy dolphins |
|---|---|
| 2-methylserine | 2.58 |
| 4-hydroxyglutamate | 4.78 |
| Trans-urocanate | 4.36 |
| Imidazole propionate | 4.52 |
| 4-imidazoleacetate | 5.94 |
| N-acetylhistamine | 8.93 |
| Hydantoin 5-propionic acid | 1.83 |
| 5-hydroxylysine | 5.60 |
| 5-aminovalerate | 6.46 |
| 2-oxoadipate | 6.51 |
| Xanthurenate | 2.64 |
| Methionine sulfone | 1.35 |
| Homocitrulline | 1.25 |
| Trans-4-hydroxyproline | 4.17 |
| Prolyl-hydroxyproline | 2.66 |
| Gamma-glutamylglycine | 1.31 |
| N6-carboxymethyllysine | 2.3 |
| N1-Methyl-2-pyridone-5-carboxamide | 1.39 |
| 2,3-dihydroxyisovalerate | 1.72 |
| Docosadioate (C22-DC) | 2.32 |
| Propionylglycine | 3.35 |
| Lignoceroylcarnitine (C24) | 4.60 |
| Cerotoylcarnitine (C26) | 5.93 |
| Behenoylcarnitine (C22) | 2.73 |
| 2-hydroxymyristate | 1.23 |
| 16-hydroxypalmitate | 1.35 |
| PC (20:0/14:1) | 3.44 |
| PC (20:0/20:3) | 2.63 |
| PC (20:0/22:4) | 1.53 |
| PE (16:0/16:0) | 1.54 |
| FFA (20:0) | 2.62 |
| DAG (14:1/18:1) | 1.42 |
| TAG 44:2-FA18:2 | 2.01 |

Linear correlations were used to test for associations between specific biochemicals and clinical pathology indices, specifically glucose, neutrophils, cholesterol, triglycerides, GGT, lymphocytes, iron, and red blood cells. Table 2 summarizes small molecule metabolites that negatively correlated with glucose, neutrophils, cholesterol, triglycerides, GGT, lymphocytes, and/or iron; and/or positively correlated with red blood cells.

TABLE 2

| Small molecule metabolites in serum and correlations with clinical indices in dolphins | Anemia (RBCs) | | Inflammation (Neutrophils) | | Dyslipidemia (Cholesterol) | | Dyslipidemia (Triglycerides) | |
|---|---|---|---|---|---|---|---|---|
| | P value | $R^2$ | P value | $R^2$ | P value | $R^2$ | P value | $R^2$ |
| 2-methylserine | <0.001 | 0.25 | | | 0.015 | −0.2 | | |
| 4-hydroxyglutamate | 0.0009 | 0.17 | 0.0009 | −0.2 | 0.015 | −0.2 | | |
| N-acetyl-aspartyl-glutamate | 0.005 | 0.26 | | | | | | |
| 2-pyrrolidinone | 0.002 | 0.29 | | | 0.042 | −0.2 | | |
| Trans-urocanate | 0.001 | 0.17 | | | | | | |
| Imidazole propionate | 0.006 | 0.25 | | | | | 0.042 | −0.11 |
| 1-ribosyl-imidazoleacetate | 0.004 | 0.26 | 0.042 | −0.1 | 0.01 | −0.2 | | |
| 4-imidazoleacetate | 0.005 | 0.26 | 0.006 | −0.1 | 0.046 | −0.1 | | |
| N-acetylhistamine | <0.001 | 0.39 | | | 0.005 | −0.2 | 0.006 | −0.15 |
| Hydantoin 5-propionic acid | 0.016 | 0.22 | | | | | | |
| 5-hydroxylysine | 0.0001 | 0.35 | | | 0.0006 | −0.2 | | |
| 5-aminovalerate | | | 0.0004 | −0.2 | 0.004 | −0.2 | 0.0002 | −0.2 |
| 2-oxoadipate | <0.001 | 0.4 | | | | | | |

TABLE 2-continued

| Metabolite | | | | | | | | |
|---|---|---|---|---|---|---|---|---|
| Xanthurenate | | | 0.007 | −0.1 | 0.0004 | −0.2 | | |
| Methionine sulfone | <0.001 | 0.22 | 0.032 | −0.1 | <0.001 | −0.6 | | |
| Homocitrulline | <0.001 | 0.24 | <0.001 | −0.2 | | | | |
| Trans-4-hydroxyproline | 0.007 | 0.14 | <0.001 | −0.3 | <0.001 | −0.3 | | |
| Prolyl-hydroxyproline | <0.001 | 0.39 | <0.001 | −0.3 | 0.054 | −0.2 | | |
| Guanidinosuccinate | 0.002 | 0.28 | 0.027 | −0.1 | 0.002 | −0.3 | 0.001 | −0.17 |
| Gamma-glutamylglutamine | 0.02 | 0.13 | 0.033 | −0.1 | 0.033 | −0.1 | <0.001 | −0.27 |
| Gamma-glutamylglycine | <0.001 | 0.21 | <0.001 | −0.2 | | | | |
| N6-carboxymethyllysine | 0.0004 | 0.32 | | | 0.003 | −0.3 | | |
| N1-Methyl-2-pyridone-5-carboxamide | 0.012 | 0.23 | | | | | | |
| 2,3-dihydroxyisovalerate | 0.0001 | 0.36 | | | | | | |
| 2-hydroxyoctanoate | <0.001 | 0.25 | | | | | | |
| 2-hydroxydecanoate | 0.002 | 0.16 | | | | | | |
| 8-hydroxyoctanoate | 0.02 | 0.12 | | | | | 0.045 | −0.11 |
| Heptanoate (C7:0) | <0.001 | 0.39 | | | | | | |
| Caprylate (C8:0) | 0.012 | 0.23 | | | | | | |
| Pelargonate (C9:0) | <0.001 | 0.47 | | | | | | |
| Undecanoate (C11:0) | <0.001 | 0.45 | | | | | | |
| Docosadioate (C22-DC) | 0.008 | 0.24 | | | | | | |
| Propionylglycine | 0.011 | 0.23 | | | 0.039 | −0.2 | | |
| Lignoceroylcarnitine (C24) | 0.0005 | 0.18 | <0.001 | −0.2 | | | | |
| Cerotoylcarnitine (C26) | <0.001 | 0.22 | 0.0002 | −0.2 | | | | |
| N-palmitoylglycine | 0.0001 | 0.36 | | | | | | |
| Cis-4-decenoylcarnitine (C10:1) | 0.0001 | 0.35 | | | 0.05 | −0.2 | | |
| Behenoylcarnitine (C22) | 0.002 | 0.27 | | | | | | |
| Pentadecanoylcarnitine (C15) | <0.001 | 0.45 | | | | | | |
| Arachidonoylcholine | <0.001 | 0.45 | | | | | | |
| 2-hydroxymyristate | 0.004 | 0.26 | | | | | | |
| 16-hydroxypalmitate | 0.009 | 0.24 | | | | | | |
| PC (18:2/22:4) | | | <0.001 | −0.3 | 0.007 | −0.2 | | |
| PC (20:0/14:1) | 0.018 | 0.12 | <0.001 | −0.3 | | | | |
| PC (20:0/20:3) | 0.012 | 0.13 | 0.0008 | −0.2 | | | | |
| PC (20:0/22:4) | 0.003 | 0.16 | 0.018 | −0.1 | | | | |
| PE (16:0/16:0) | | | 0.021 | −0.1 | | | | |
| FFA (20:0) | | | 0.0002 | −0.2 | | | | |
| FFA (24:0) | 0.004 | −0.2 | 0.042 | −0.1 | 0.013 | −0.1 | | |
| FFA (24:1) | | | 0.038 | −0.1 | 0.008 | −0.1 | | |
| FFA (20:2) | | | | | 0.016 | −0.1 | 0.008 | −0.14 |
| CER (14:0) | | | 0.045 | −0.1 | | | | |
| HCER(26:1) | | | 0.047 | −0.1 | | | | |
| LCER (26:0) | | | 0.007 | −0.1 | 0.006 | −0.2 | | |
| DAG (14:1/18:1) | 0.003 | 0.16 | 0.002 | −0.2 | 0.04 | −0.1 | | |
| TAG 44:2-FA18:2 | 0.001 | 0.17 | | | | | | |
| MAG (12:0) | | | 0.002 | −0.2 | 0.01 | −0.1 | | |
| MAG (17:0) | 0.002 | −0.2 | | | | | | |
| MAG (20:0) | 0.0004 | −0.2 | 0.002 | −0.2 | 0.0004 | −0.2 | | |
| MAG (20:2) | 0.011 | −0.1 | 0.033 | −0.1 | 0.019 | −0.1 | | |

| Small molecule metabolites in serum and correlations with clinical indices in dolphins | Liver Disease (GGT) | | Iron Overload (Iron) | | Hyperglycemia (Glucose) | | |
|---|---|---|---|---|---|---|---|
| | $R^2$ | P value | $R^2$ | P value | $R^2$ | P value | $R^2$ |
| 2-methylserine | −0.2 | | | | | | |
| 4-hydroxyglutamate | −0.2 | 0.002 | −0.2 | | | <0.001 | −0.22 |
| N-acetyl-aspartyl-glutamate | | | | | | | |
| 2-pyrrolidinone | | | | | | | |
| Trans-urocanate | | | | | | 0.0006 | −0.18 |
| Imidazole propionate | −0.3 | 0.03 | −0.1 | | | | |
| 1-ribosyl-imidazoleacetate | −0.2 | | | | | | |
| 4-imidazoleacetate | −0.2 | | | | | 0.054 | −0.18 |
| N-acetylhistamine | −0.3 | | | 0.006 | −0.1 | | |
| Hydantoin 5-propionic acid | | | | | | | |
| 5-hydroxylysine | | | | | | 0.0001 | −0.21 |
| 5-aminovalerate | −0.2 | | | | | | |
| 2-oxoadipate | | | | | | | |
| Xanthurenate | −0.4 | 0.003 | −0.2 | | | 0.0001 | −0.21 |
| Methionine sulfone | | | | | | 0.017 | −0.12 |
| Homocitrulline | | | 0.019 | −0.1 | | | |
| Trans-4-hydroxyproline | −0.3 | 0.0006 | −0.2 | | | <0.001 | −0.41 |
| Prolyl-hydroxyproline | −0.3 | | | | | | |
| Guanidinosuccinate | −0.3 | <0.001 | −0.2 | <0.001 | −0.3 | | |
| Gamma-glutamylglutamine | | <0.001 | −0.3 | | | 0.021 | −0.12 |
| Gamma-glutamylglycine | | | | | | <0.0001 | −0.23 |
| N6-carboxymethyllysine | | | | | | | |
| N1-Methyl-2-pyridone-5-carboxamide | −0.3 | | | | | | |
| 2,3-dihydroxyisovalerate | | | | | | | |

TABLE 2-continued

| Biochemical | | | | | | |
|---|---|---|---|---|---|---|
| 2-hydroxyoctanoate | −0.4 | | | | | |
| 2-hydroxydecanoate | −0.3 | | | | | |
| 8-hydroxyoctanoate | | | | | | |
| Heptanoate (C7:0) | −0.2 | | | | | |
| Caprylate (C8:0) | | | | | | |
| Pelargonate (C9:0) | −0.2 | | | | | |
| Undecanoate (C11:0) | −0.2 | | | | | |
| Docosadioate (C22-DC) | | | | | | |
| Propionylglycine | | | | | | |
| Lignoceroylcarnitine (C24) | −0.2 | 0.017 | −0.1 | | | |
| Cerotoylcarnitine (C26) | −0.3 | 0.037 | −0.1 | | | |
| N-palmitoylglycine | | | | | | |
| Cis-4-decenoylcarnitine (C10:1) | −0.3 | | | | | |
| Behenoylcarnitine (C22) | | | | | | |
| Pentadecanoylcarnitine (C15) | −0.2 | | | | | |
| Arachidonoylcholine | −0.3 | | | | | |
| 2-hydroxymyristate | | | | | | |
| 16-hydroxypalmitate | | | | | | |
| PC (18:2/22:4) | | | | | | |
| PC (20:0/14:1) | | | | | | |
| PC (20:0/20:3) | | | | | | |
| PC (20:0/22:4) | | | | | | |
| PE (16:0/16:0) | | | | | | |
| FFA (20:0) | | | | | | |
| FFA (24:0) | | <0.001 | −0.2 | | 0.002 | −0.16 |
| FFA (24:1) | | <0.001 | −0.3 | <0.001 | −0.3 | 0.0001 | −0.21 |
| FFA (20:2) | | 0.005 | −0.2 | | | |
| CER (14:0) | | 0.008 | −0.1 | | | |
| HCER(26:1) | | <0.001 | −0.2 | <0.001 | −0.2 | |
| LCER (26:0) | | 0.009 | −0.1 | | | |
| DAG (14:1/18:1) | | | | | | |
| TAG 44:2-FA18:2 | | 0.014 | −0.1 | | | |
| MAG (12:0) | | 0.018 | −0.1 | | | |
| MAG (17:0) | | 0.028 | −0.1 | | 0.024 | −0.12 |
| MAG (20:0) | | 0.0002 | −0.2 | | | |
| MAG (20:2) | | | | | | |

The relevance of the presence of age category to each biochemical was assessed using two-way ANOVA main effects considering disease category, age, and a mixed disease:age bin calculation. Table 3 summarizes significant (P value≤0.05) effects of age, disease, and/or age+disease on small molecule metabolites in the animal study population.

TABLE 3

| Biochemical | Age Effect | Disease Effect | Age + Disease Effect |
|---|---|---|---|
| 2-methylserine | — | 0.002 | 0.006 |
| 4-hydroxyglutamate | 0.001 | — | — |
| N-acetyl-aspartyl-glutamate (NAAG) | <0.0001 | 0.002 | 0.0004 |
| 2-pyrrolidinone | — | 0.019 | — |
| Trans-urocanate | 0.024 | <0.0001 | 0.003 |
| 1-ribosyl-imidazoleacetate | 0.03 | — | — |
| 4-imidazoleacetate | 0.017 | — | — |
| N-acetylhistamine | 0.017 | 0.001 | — |
| Hydantoin 5-propionic acid | 0.001 | <0.0001 | <0.0001 |
| 5-hydroxylysine | 0.035 | 0.013 | — |
| 5-aminovalerate | 0.01 | 0.007 | — |
| 2-oxoadipate | 0.02 | — | — |
| Xanthurenate | <0.0001 | 0.012 | 0.018 |
| Methionine sulfone | <0.0001 | — | — |
| Homocitrulline | — | 0.012 | 0.001 |
| Trans-4-hydroxyproline | 0.0006 | 0.0003 | — |
| Prolyl-hydroxyproline | <0.0001 | 0.0002 | — |
| Guanidinosuccinate | — | — | <0.0001 |
| Gamma-glutamylglutamine | 0.012 | — | — |
| N6-carboxymethyllysine | — | — | 0.0005 |
| N1-Methyl-2-pyridone-5-carboxamide | 0.013 | — | — |
| 2-hydroxyoctanoate | <0.0001 | 0.008 | — |
| 2-hydroxydecanoate | <0.0001 | 0.016 | 0.017 |
| 8-hydroxyoctanoate | 0.011 | 0.031 | |
| Heptanoate (C7:0) | 0.0009 | — | — |
| Caprylate (C8:0) | 0.003 | — | 0.016 |
| Pelargonate (C9:0) | — | — | 0.013 |
| Undecanoate (C11:0) | <0.0001 | — | 0.0002 |
| Docosadioate (C22-DC) | 0.004 | 0.0001 | 0.011 |
| Propionylglycine | 0.034 | — | — |
| Lignoceroylcarnitine (C24) | <0.0001 | — | 0.003 |
| Cerotoylcarnitine (C26) | <0.0001 | — | <0.0001 |
| N-palmitoylglycine | — | 0.019 | — |
| Cis-4-decenoylcarnitine (C10:1) | — | — | 0.008 |
| Behenoylcarnitine (C22) | 0.002 | 0.023 | 0.016 |
| Arachidonoylcholine | — | 0.048 | 0.001 |
| 2-hydroxymyristate | 0.001 | 0.017 | — |
| 16-hydroxypalmitate | — | 0.009 | — |
| PC (18:2/22:4) | — | 0.002 | <0.0001 |
| PC (20:0/14:1) | 0.003 | 0.004 | — |
| PC (20:0/20:3) | 0.052 | 0.014 | — |
| FFA (20:0) | <0.0001 | <0.0001 | — |
| FFA (24:0) | 0.009 | <0.0001 | 0.029 |
| FFA (24:1) | — | <0.0001 | 0.002 |
| FFA (20:2) | 0.015 | 0.016 | — |
| CER (14:0) | — | 0.005 | — |
| HCER (26:1) | 0.007 | 0.046 | — |
| DAG (14:1/18:1) | 0.001 | <0.0001 | 0.003 |
| TAG 44:2-FA18:2 | 0.039 | — | — |
| MAG (12:0) | — | 0.026 | <0.0001 |
| MAG (17:0) | — | 0.001 | 0.255 |
| MAG (20:0) | — | 0.0001 | 0.02 |
| MAG (20:2) | — | 0.0006 | — |

Example 2

Bottlenose dolphins (*Tursiops truncatus*) are large-brained, long-lived mammals that develop aging-associated conditions similar to humans, including inflammation, anemia, hyperglycemia, dyslipidemia, hyperinsulinemia, liver disease, and iron overload. For over 60 years, the U.S. Navy has cared for a population of approximately 100 dolphins. While the average lifespan of dolphins in the wild is 20 years, Navy dolphins on average live 32 years, more than fifty percent longer than wild dolphins. Approximately one-third of Navy dolphins are between 30 to 50 years old. Due in part to these populations' age differences, Navy dolphins have higher mean glucose, cholesterol, triglycerides, GGT, insulin, iron, and ferritin levels compared to wild dolphins living in Sarasota Bay, Florida Proposed risk factors for these conditions in MMP dolphins include advanced age and diet (see Venn-Watson S, Smith C R, Gomez F, Jensen E D (2011) Physiology of aging among healthy, older bottlenose dolphins (*Tursiops truncatus*): comparisons with aging humans. *J Comp Phys B* 181:667-680). It can be hypothesized that differences in dietary fish (and differences in certain small molecule metabolites associated with fish-based dietary changes) can be responsible for the risk of exacerbating conditions that negatively impact longevity and quality of life, including anemia, hypercholesterolemia, and hyperinsulinemia.

This study examined the impact on anemia by modifying serum metabolites through a modified fish diet in 20 MMP dolphins ("Modified Diet"). The dolphins lived in netted enclosures within San Diego Bay. The diets of the 20 modified diet dolphins were modified from a 75% capelin (plus 25% mix of squid, herring or mackerel) baseline diet to a diet consisting of 25% capelin, 50% mullet, and 25% mix of squid, herring, or mackerel while maintaining the same kilocalories. On blood collection days, modified diet dolphins were fed one-third of their daily diet in the morning after their routine overnight fast and 2 h postprandial, in-water, and trained blood samples were drawn (typically near 10:00 a.m.). An additional ten MMP dolphins ("Baseline Diet") were maintained on the baseline capelin diet throughout the study period. There were no differences in age, sex, or body weight when comparing the two groups (Table 4).

Table 4 provides comparisons of blood-based clinical values among modified diet dolphins and baseline diet dolphins. *=p value≤0.05.

Two-hour post-prandial samples were collected from modified diet dolphins and baseline diet dolphins at baseline (month 0) and at three time points following the switch to the modified diet: months 1, 3, and 6. Dolphins were assessed for changes in serum metabolites, cholesterol, insulin, and indices of anemia, including hematocrit, packed cell volume, red blood cell count, hemoglobin, and red blood cell distribution.

Changes in serum metabolites, as well as cholesterol, insulin, and indices of anemia, including hematocrit, packed cell volume, red blood cell count, hemoglobin, and red blood cell distribution, were compared in study dolphins during months 1, 3, and 6 and compared to month 0 using repeated Wilcoxon rank sum tests. Outcomes for clinical markers for modified diet dolphins and baseline diet dolphins are provided in Table 4. Cholesterol, insulin and all indicators of anemia improved in modified diet dolphins by Month 1 and through Month 6. No changes were identified in baseline diet dolphins. It is apparent in FIG. 1. that individual modified diet dolphins with low hematocrit had resolving anemia while on the modified diet.

Small molecule metabolite concentrations in serum were successfully and significantly raised in this study (Table 5). In most cases, increases in serum metabolite concentrations ranged from 1.1 to 3.0-fold higher than baseline (Month 0). In most cases, significant fold-increases in serum were achieved by Month 1 on the diet. Table 5 summarizes small molecule metabolites in serum that increased significantly among dolphins on the modified diet at Month 1 compared to 1) baseline diet dolphins at Month 1 and 2) modified diet dolphins at Month 0.

TABLE 4

| | Month 0 | | Month 1 | | Month 3 | | Month 6 | |
|---|---|---|---|---|---|---|---|---|
| | Modified Diet (n = 20) | Baseline Diet (n = 10) | Modified Diet (n = 20) | Baseline Diet (n = 10) | Modified Diet (n = 20) | Baseline Diet (n = 10) | Modified Diet (n = 20) | Baseline Diet (n = 10) |
| Age (years) | 22 ± 14 | 26 ± 10 | | | | | | |
| Body weight (lbs) | 389 ± 49 | 402 ± 45 | | | | | | |
| Female (%) | 45% | 40% | | | | | | |
| Insulin | 9.8 ± 6.1 | 9.4 ± 4.8 | 7.5 ± 4.0* | 14.8 ± 14.0 | 8.9 ± 4.4* | 16.3 ± 13.6 | 6.8 ± 4.6* | 10.3 ± 6.2 |
| Cholesterol | 183 ± 35 | 187 ± 23 | 160 ± 26* | 186 ± 24 | 167 ± 28* | 199 ± 33 | 160 ± 31* | 188 ± 28 |
| Hemoglobin | 13 ± 1 | 13 ± 1 | 14 ± 1 | 13 ± 1 | 15 ± 1* | 14 ± 1 | 15 ± 1* | 13 ± 1 |
| Hematocrit | 44 ± 5 | 44 ± 3 | 46 ± 3* | 44 ± 3 | 47 ± 2* | 45 ± 2 | 47 ± 2* | 44 ± 2 |
| RDW | 15 ± 2 | 15 ± 2 | 14 ± 1 | 15 ± 2 | 13 ± 1* | 15 ± 2 | 13 ± 1* | 16 ± 3 |
| RBC | 3.0 ± 0.3 | 3.0 ± 0.2 | 3.2 ± 0.2 | 3.0 ± 0.2 | 3.4 ± 0.2* | 3.2 ± 0.2 | 3.3 ± 0.3* | 3.1 ± 0.2 |
| NRBC | 1.8 ± 2.9 | 1.4 ± 2.5 | 0.5 ± 0.9* | 1.2 ± 1.5 | 0.2 ± 0.6* | 1.1 ± 1.0 | 0.2 ± 0.5 | 0.7 ± 1.3 |

TABLE 5

| Small molecule metabolite | Significant fold differences in serum between Baseline and Modified Diet groups at Month 1 | Significant fold differences in serum between Month 0 and Month 1 in Modified Diet group |
|---|---|---|
| 2-methylserine | 1.52 | 1.62 |
| 4-hydroxyglutamate | 1.74 | 1.75 |
| N-acetyl-aspartyl-glutamate (NAAG) | — | — |
| 2-pyrrolidinone | 1.16 | 1.12 |
| Trans-urocanate | 1.06 (Month 3) | 1.30 (Month 3) |
| Imidazole propionate | 2.29 (Month 3) | 3.48 |
| 1-ribosyl-imidazoleacetate | 2.47 | 3.29 |
| 4-imidazoleacetate | 2.74 (Month 3) | 3.94 |
| N-acetylhistamine | 5.36 | 7.68 |
| Hydantoin 5-propionic acid | 1.56 (Month 3) | 1.26 (Month 3) |
| 5-hydroxylysine | 1.28 | 1.28 |
| 5-aminovalerate | 1.35 | 1.68 |
| 2-oxoadipate | — | 1.25 |
| Xanthurenate | 1.20 (Month 6) | 1.33 (Month 6) |
| Methionine sulfone | 1.42 | 1.48 |
| Homocitrulline | 1.34 (Month 3) | 1.32 |
| Trans-4-hydroxyproline | 1.46 | 1.52 |
| Prolyl-hydroxyproline | 1.44 | 1.25 |
| Guanidinosuccinate | 1.84 | 1.53 |
| Gamma-glutamylglutamine | — | — |
| Gamma-glutamylglycine | — | — |
| N6-carboxymethyllysine | 1.78 | 2.11 |
| N1-Methyl-2-pyridone-5-carboxamide | 1.38 | 1.18 (Month 6) |
| N1-Methyl-4-pyridone-3-carboxamide | — | 1.18 (Month 6) |
| 2,3-dihydroxyisovalerate | 2.02 | 1.89 |
| 2-hydroxyoctanoate | 1.29 | 1.29 |
| 2-hydroxydecanoate | — | 1.17 (Month 3) |
| 8-hydroxyoctanoate | 1.28 (Month 3) | 1.17 (Month 3) |
| Heptanoate (C7:0) | 1.25 (Month 3) | 1.13 (Month 3) |
| Caprylate (C8:0) | — | 1.21 |
| Pelargonate (C9:0) | 1.27 (Month 3) | 1.17 |
| Undecanoate (C11:0) | 1.29 (Month 3) | 1.15 |
| 10-undecanoate (C11:1n1) | 1.98 | 1.92 |
| Pentadecanoate (C15:0) | 2.73 | 2.62 |
| Margarate (C17:0) | 2.4 | 2.52 |
| 10-heptadecanoate (C17:1n7) | 2.31 | 2.2 |
| 10-nonadecanoate (19:1n9) | 1.34 | 1.37 |
| 15-methylpalmitate (i17:0) | 1.23 | 1.18 |
| 17-methylstearate (i19:0) | 1.37 | 1.36 |
| 2-hydroxyphytanate | — | — |
| Dodecadienoate (C12:2) | 2.91 | 1.82 |
| Docosadioate (C22-DC) | 1.21 (Month 3) | 1.39 |
| Propionylglycine | 1.58 (Month 6) | 1.30 (Month 6) |
| Lignoceroylcarnitine (C24) | 2.8 | 2.81 |
| Cerotoylcarnitine (C26) | 3.38 | 2.88 |
| N-palmitoylglycine | — | 1.15 |
| Cis-4-decenoylcarnitine (C10:1) | 2.13 | 2.7 |
| Behenoylcarnitine (C22) | 1.32 | 1.48 |
| Pentadecanoylcarnitine (C15) | 2.63 | 2.92 |
| Arachidonoylcholine | 2.54 | 2.57 |
| 2-hydroxymyristate | — | 1.26 (Month 6) |
| 16-hydroxypalmitate | — | 1.26 |
| 1-stearoyl-2-arachidonoyl-GPC (18:0/20:4) | 1.71 | 1.92 |
| 1-palmitoyl-2-arachidonoyl-GPC (16: 0/20: 4n6) | 1.83 | 1.94 |
| 1-palmitoyl-2-arachidonoyl-GPE (16:0/20:4) | 2.22 | 2.48 |
| 1-stearoyl-2-arachidonoyl-GPE (18:0/20:4) | 1.92 | 2.08 |
| 1-stearoyl-2-oleoyl-GPS (18:0/18:1) | 1.92 | — |
| 1-arachidonoyl-GPC (20:4n6) | 2.22 | 2.33 |
| 1-lignoceroyl-GPC (24:0) | 2.96 | 2.86 |
| 1-arachidonoyl-GPE (20:4n6) | 2.06 | 2.2 |
| 1-(1-enyl-palmitoyl)-2-arachidonoyl-GPE (P-16:0/20:4) | 2.01 | 1.93 |
| 1-(1-enyl-palmitoyl)-2-oleoyl-GPC (P-16:0/18:1) | 1.30 (Month 6) | 1.16 (Month 3) |
| 1-(1-enyl-palmitoyl)-2-arachidonoyl-GPC (P-16:0/20:4) | 2.92 | 2.71 |
| 1-(1-enyl-stearoyl)-2-arachidonoyl-GPE (P-18:0/20:4) | 2.26 | 2.29 |
| 1-(1-enyl-palmitoyl)-GPC (P-16:0) | 1.42 | 1.27 |
| 1-arachidonylglycerol (20:4) | 2.43 | 2.25 |
| 1-heptadecenoylglycerol (17:1) | 2.34 | 2.27 |
| stearoyl-arachidonoyl-glycerol (18:0/20:4) [2] | 1.79 | 1.7 |
| oleoyl-arachidonoyl-glycerol (18:1/20:4) [1] | 1.68 | 1.65 |
| oleoyl-arachidonoyl-glycerol (18:1/20:4) [2] | 3.37 | 2.93 |
| Stearoyl sphingomyelin (d18:1/18:0) | 1.24 | 1.21 |
| Behenoyl sphingomyelin (d18:1/22: 0) | 1.63 | 1.46 |

TABLE 5-continued

| Small molecule metabolite | Significant fold differences in serum between Baseline and Modified Diet groups at Month 1 | Significant fold differences in serum between Month 0 and Month 1 in Modified Diet group |
|---|---|---|
| Tricosanoyl sphingomyelin (d18:1/23:0) | 3.02 | 2.82 |
| Lignoceroyl sphingomyelin (d18:1/24:0) | 2.73 | 2.3 |
| Sphingomyelin (d18:2/23:1) | 1.32 | 1.16 |
| Sphingomyelin (d18:2/24:2) | 1.51 | 1.31 |
| Sphingomyelin (d17:1/14:0, d16:1/15:0) | 2.88 | 2.9 |
| Sphingomyelin (d17:1/16:0, d18:1/15:0, d16:1/17:0) | 2.88 | 2.56 |
| Sphingomyelin (d17:2/16:0, d18:2/15:0) | 1.76 | 1.61 |
| Sphingomyelin (d18:1/17:0, d17:1/18:0, d19:1/16:0) | 1.99 | 1.82 |
| Sphingomyelin (d18:1/19:0, d19:1/18:0) | 1.95 | 1.83 |
| Sphingomyelin (d18:1/21:0, d17:1/22:0, d16:1/23:0) | 2.05 | 1.93 |
| Sphingomyelin (d18:2/21:0, d16:2/23:0) | 1.22 | 1.08 |
| Sphingomyelin (d18:2/23:0, d18:1/23:1, d17:1/24:1) | 1.97 | 1.69 |

Demonstrated increased serum concentrations of specific small molecule metabolites in Group A dolphins on the modified diet correlated with lowered cholesterol, lowered insulin, and improved anemia (Table 6). Thus, these data support that raising serum concentrations of specific small molecule metabolites lowered cholesterol, lowered insulin, and resolved anemia. Table 6 summarizes small molecule metabolites that significantly increased among modified diet dolphins and correlated with demonstrated clinical benefits, specifically lower cholesterol, lower insulin and/or raised red blood cells (RBCs).

TABLE 6

Associations between serum metabolite levels and aging-associated conditions that impact quality of life and longevity

| Small molecule metabolite | Anemia (RBCs) | | Dyslipidemia (Cholesterol) | | Elevated Insulin (Insulin) | |
|---|---|---|---|---|---|---|
| | P value | $R^2$ | P value | $R^2$ | P value | $R^2$ |
| 2-methylserine | <0.001 | 0.25 | 0.015 | −0.22 | 0.031 | −0.2 |
| 4-hydroxyglutamate | 0.0009 | 0.17 | 0.015 | −0.22 | 0.038 | −0.19 |
| N-acetyl-aspartyl-glutamate (NAAG) | 0.005 | 0.26 | | | | |
| 2-pyrrolidinone | 0.002 | 0.29 | 0.042 | −0.19 | | |
| Imidazole propionate | 0.006 | 0.25 | | | 0.003 | −0.27 |
| 1-ribosyl-imidazoleacetate | 0.004 | 0.26 | 0.01 | −0.23 | 0.046 | −0.18 |
| 4-imidazoleacetate | 0.005 | 0.26 | 0.046 | −0.11 | 0.025 | −0.2 |
| N-acetylhistamine | <0.001 | 0.39 | 0.005 | −0.15 | 0.001 | −0.29 |
| Hydantoin 5-propionic acid | 0.016 | 0.22 | | | | |
| 5-hydroxylysine | 0.0001 | 0.35 | 0.0006 | −0.18 | | |
| 5-aminovalerate | | | 0.004 | −0.15 | 0.013 | −0.23 |
| 2-oxoadipate | <0.001 | 0.4 | | | | |
| Xanthurenate | | | 0.0004 | −0.19 | <0.001 | −0.41 |
| Methionine sulfone | <0.001 | 0.22 | <0.001 | −0.56 | | |
| Trans-4-hydroxyproline | 0.007 | 0.14 | <0.001 | −0.27 | 0.005 | −0.25 |
| Prolyl-hydroxyproline | <0.001 | 0.39 | 0.054 | −0.18 | 0.0004 | −0.32 |
| Guanidinosuccinate | 0.002 | 0.28 | 0.002 | −0.29 | 0.002 | −0.28 |
| N6-carboxymethyllysine | 0.0004 | 0.32 | 0.003 | −0.27 | | |
| N1-Methyl-2-pyridone-5-carboxamide | 0.012 | 0.23 | | | 0.0004 | −0.32 |
| N1-Methyl-4-pyridone-3-carboxamide | 0.014 | 0.22 | | | 0.009 | −0.24 |
| 2,3-dihydroxyisovalerate | 0.0001 | 0.36 | | | | |
| 2-hydroxyoctanoate | <0.001 | 0.25 | | | 0.0001 | −0.36 |
| 2-hydroxydecanoate | 0.002 | 0.16 | | | 0.001 | −0.29 |
| 8-hydroxyoctanoate | 0.02 | 0.12 | | | | |
| Heptanoate (C7:0) | <0.001 | 0.39 | | | 0.01 | −0.23 |
| Caprylate (C8:0) | 0.012 | 0.23 | | | | |
| Pelargonate (C9:0) | <0.001 | 0.47 | | | 0.021 | −0.21 |
| Undecanoate (C11:0) | <0.001 | 0.45 | | | 0.012 | −0.23 |
| 10-undecanoate (C11:1n1) | <0.001 | 0.52 | 0.04 | −0.19 | 0.0001 | −0.35 |
| Pentadecanoate (C15:0) | <0.001 | 0.53 | 0.007 | −0.25 | 0.002 | −0.28 |
| Margarate (C17:0) | <0.001 | 0.51 | 0.01 | −0.23 | 0.02 | −0.21 |
| 10-heptadecanoate (C17:1n7) | <0.001 | 0.53 | 0.05 | −0.18 | 0.003 | −0.27 |
| 10-nonadecanoate (19:1n9) | <0.001 | 0.45 | | | 0.039 | −0.19 |
| 15-methylpalmitate (i17:0) | <0.001 | 0.39 | | | | |
| 17-methylstearate (i19:0) | <0.001 | 0.46 | | | | |
| 2-hydroxyphytanate | 0.017 | 0.22 | | | 0.0001 | −0.35 |
| Dodecadienoate (C12:2) | 0.01 | 0.23 | | | 0.028 | −0.2 |
| Docosadioate (C22-DC) | 0.008 | 0.24 | | | | |

TABLE 6-continued

Associations between serum metabolite levels and aging-associated conditions that impact quality of life and longevity

| Small molecule metabolite | Anemia (RBCs) P value | R² | Dyslipidemia (Cholesterol) P value | R² | Elevated Insulin (Insulin) P value | R² |
|---|---|---|---|---|---|---|
| Propionylglycine | 0.011 | 0.23 | 0.039 | −0.19 | | |
| Lignoceroylcarnitine (C24) | 0.0005 | 0.18 | | | 0.008 | −0.24 |
| Cerotoylcarnitine (C26) | <0.001 | 0.22 | | | 0.002 | −0.28 |
| N-palmitoylglycine | 0.0001 | 0.36 | | | | |
| Cis-4-decenoylcarnitine (C10:1) | 0.0001 | 0.35 | 0.05 | −0.18 | 0.002 | −0.28 |
| Behenoylcarnitine (C22) | 0.002 | 0.27 | | | | |
| Pentadecanoylcarnitine (C15) | <0.001 | 0.45 | | | 0.007 | −0.24 |
| Arachidonoylcholine | <0.001 | 0.45 | | | 0.005 | −0.25 |
| 2-hydroxymyristate | 0.004 | 0.26 | | | | |
| 16-hydroxypalmitate | 0.009 | 0.24 | | | | |
| 1-stearoyl-2-arachidonoyl-GPC (18:0/20:4) | <0.001 | 0.51 | 0.005 | −0.26 | | |
| 1-palmitoyl-2-arachidonoyl-GPC (16:0/20:4n6) | <0.001 | 0.54 | 0.002 | −0.28 | 0.03 | −0.2 |
| 1-palmitoyl-2-arachidonoyl-GPE (16:0/20:4) | <0.001 | 0.42 | <00001 | −0.42 | | |
| 1-stearoyl-2-arachidonoyl-GPE (18:0/20:4) | <0.001 | 0.38 | 0.0001 | −0.34 | | |
| 1-stearoyl-2-oleoyl-GPS (18:0/18:1) | 0.0007 | 0.31 | 0.053 | −0.18 | | |
| 1-arachidonoyl-GPC (20:4n6) | <0.001 | 0.54 | | | 0.0009 | −0.3 |
| 1-lignoceroyl-GPC (24:0) | <0.001 | 0.52 | 0.051 | −0.18 | 0.003 | −0.27 |
| 1-arachidonoyl-GPE (20:4n6) | <0.001 | 0.56 | 0.05 | −0.18 | 0.001 | −0.29 |
| 1-(1-enyl-palmitoyl)-2-arachidonoyl-GPE (P-16:0/20:4) | <0.001 | 0.48 | 0.043 | −0.19 | 0.002 | −0.28 |
| 1-(1-enyl-palmitoyl)-2-oleoyl-GPC (P-16:0/18:1) | <0.001 | 0.49 | | | 0.003 | −0.27 |
| 1-(1-enyl-palmitoyl)-2-arachidonoyl-GPC (P-16:0/20:4) | <0.001 | 0.53 | 0.005 | −0.25 | 0.003 | −0.27 |
| 1-(1-enyl-stearoyl)-2-arachidonoyl-GPE (P-18:0/20:4) | <0.001 | 0.49 | 0.033 | −0.19 | | |
| 1-(1-enyl-palmitoyl)-GPC (P-16:0) | <0.001 | 0.48 | | | <0.001 | −0.41 |
| 1-arachidonylglycerol (20:4) | 0.005 | 0.25 | 0.035 | −0.19 | | |
| 1-heptadecenoylglycerol (17:1) | 0.003 | 0.27 | 0.02 | −0.21 | | |
| stearoyl-arachidonoyl-glycerol (18:0/20:4) [2] | <0.001 | 0.47 | | | | |
| oleoyl-arachidonoyl-glycerol (18:1/20:4) | 0.02 | 0.21 | 0.0009 | −0.3 | | |
| oleoyl-arachidonoyl-glycerol (18:1/20:4) | 0.014 | 0.22 | 0.004 | −0.26 | | |
| Stearoyl sphingomyelin (d18:1/18:0) | <0.001 | 0.4 | 0.045 | 0.18 | | |
| Behenoyl sphingomyelin (d18:1/22:0) | <0.001 | 0.5 | | | 0.0009 | −0.3 |
| Tricosanoyl sphingomyelin (d18:1/23:0) | <0.001 | 0.55 | | | 0.0009 | −0.3 |
| Lignoceroyl sphingomyelin (d18:1/24:0) | <0.001 | 0.51 | | | 0.0002 | −0.33 |
| Sphingomyelin (d18:2/23:1) | <0.001 | 0.41 | | | 0.002 | −0.28 |
| Sphingomyelin (d18:2/24:2) | | | 0.0005 | −0.31 | 0.004 | −0.26 |
| Sphingomyelin (d17:1/14:0, d16:1/15:0) | <0.001 | 0.51 | | | 0.002 | −0.28 |
| Sphingomyelin (d17:1/16:0, d18:1/15:0, d16:1/17:0) | <0.001 | 0.52 | 0.001 | −0.29 | 0.003 | −0.27 |
| Sphingomyelin (d17:2/16:0, d18:2/15:0) | <0.001 | 0.48 | | | <0.001 | −0.37 |
| Sphingomyelin (d18:1/17:0, d17:1/18:0, d19:1/16:0) | <0.001 | 0.51 | 0.032 | −0.2 | 0.012 | −0.23 |
| Sphingomyelin (d18:1/19:0, d19:1/18:0) | <0.001 | 0.56 | | | 0.0002 | −0.34 |
| Sphingomyelin (d18:1/21:0, d17:1/22:0, d16:1/23:0) | <0.001 | 0.58 | | | 0.0004 | −0.32 |
| Sphingomyelin (d18:2/21:0, d16:2/23:0) | <0.001 | 0.43 | | | 0.002 | −0.28 |
| Sphingomyelin (d18:2/23:0, d18:1/23:1, d17:1/24:1) | <0.001 | 0.56 | | | 0.033 | −0.2 |

In summary, results from the dolphin study demonstrated that 1) serum-based metabolites can be altered by dietary interventions, 2) in most cases, metabolite concentrations in the serum increased between 1.1 to 3-fold higher than baseline, pre-intervention levels, 3) increased serum concentrations of specific small molecule metabolites correlated with demonstrated clinical benefits, including lower cholesterol, lower insulin, and/or alleviated anemia.

Sample Collection and Transport

Blood was collected into BD Vacutainer serum separator tubes (for serum fatty acid profiles). Serum separator tubes were centrifuged at 3000 rpm for 10 minutes within 30 to 60 minutes of collection and chilled during processing until shipment. Serum was transferred to cryovials and stored at −80° C. until shipment on dry ice via overnight courier to the reference laboratories.

Sample Analysis

Red blood cell indices, including red blood cell count and hemoglobin, were performed by the Naval Medical Center San Diego. Betadine and alcohol swabs were used to clean the ventral aspect of the dolphin's fluke using the appropriate aseptic technique. Blood was then drawn with a 21 g×¾ in. winged infusion set with a luer adapter and vacutainer hub. A BD vacutainer blood tube with 7.2 mg EDTA was then applied to the luer adapter and blood was evacuated using the vacuum from the tubes. The blood was then shipped on ice packs to reference laboratories. A 4 ml EDTA vacutainer was shipped on an ice pack and analyzed by the Naval Medical Center of San Diego. The automated HCT, hemoglobin and red blood cell count were analyzed using the Sysmex XE-5000 (Sysmex Canada Inc., Mississauga, Ontario) per the manufacturer's protocol. For in-house packed cell volume, whole blood was taken from a 4 mL BD Vacutainer tube with 7.2 mg EDTA and used to fill a heparinized mylar wrapped 75 MM hematocrit tubes. Clay was packed into one end to prevent leakage during centrifugation. Once the hematocrit tube was sealed, it was placed into the Thermo IEC MICRO-MB centrifuge (Thermo Fisher Scientific, Waltham, Ma. 02451). The blood sample was spun at 11,500 rpm for 5 minutes. The hematocrit tube was then removed and placed into the micro-capillary reader to determine results.

Serum samples were analyzed for small molecules using global metabolomics and complex lipid profiling. Briefly, serum extracts were prepared and analyzed using three methods: ultrahigh performance liquid chromatography-tandem mass spectroscopy (UPLC-MS/MS) with positive ion mode electrospray ionization (ESI), UPLC-MS/MS with negative ion mode ESI, and hydrophilic interaction liquid chromatography (UPLC-MS/MS).

The informatics system consisted of four major components, the Laboratory Information Management System (LIMS), the data extraction and peak-identification software, data processing tools for QC and compound identification, and a collection of information interpretation and visualization tools for use by data analysts. The hardware and software foundations for these informatics components were the LAN backbone, and a database server running Oracle 10.2.0.1 Enterprise Edition.

Raw data were extracted, peak-identified and QC processed using proprietary hardware and software. Compounds were identified by comparison to library entries of purified standards or recurrent unknown entities. Biochemical identifications were based on three criteria: retention index within a narrow RI window of the proposed identification, accurate mass match to the library +/−10 ppm, and the MS/MS forward and reverse scores between the experimental data and authentic standards. Peaks were quantified using area-under-the-curve. A data normalization step was performed to correct variation resulting from instrument inter-day tuning differences.

Serum samples were also analyzed for complex lipids. Briefly, lipids were extracted from samples in methanol: dichloromethane in the presence of internal standards. The extracts were concentrated under nitrogen and reconstituted in 0.25 mL of 10 mM ammonium acetate dichloromethane: methanol (50:50). The extracts were transferred to inserts and placed in vials for infusion-MS analysis, performed on a Shimadzu LC with nano PEEK tubing and the Sciex Selexlon-5500 QTRAP. The samples were analyzed via both positive and negative mode electrospray. The 5500 QTRAP scan was performed in MRM mode with the total of more than 1,100 MRMs. Individual lipid species were quantified by taking the peak area ratios of target compounds and their assigned internal standards, then multiplying by the concentration of internal standard added to the sample. Lipid class concentrations were calculated from the sum of all molecular species within a class, and small molecule metabolite compositions were determined by calculating the proportion of each class comprised by individual small molecule metabolites.

Statistical analyses were conducted using World Programming System software (World Programming Ltd., Hampshire, United Kingdom). Significance was defined as a P value less than or equal to 0.05. Red blood cell index values (hematocrit, packed cell volume, hemoglobin, and red blood cell counts) and serum small molecule metabolite concentrations (total and individual classes) from Month 1, 3, and 6 were compared with Month 0 for both modified diet and baseline diet dolphins using ANOVA contrasts.

Red Blood Cell Index Values

Comparisons of red blood cell index values in bottlenose dolphins (*Tursiops truncatus*) fed a Modified Diet versus baseline diet over 6 months. The Modified Diet is described above. Table 7 (depicted graphically in FIG. 1) provides data on improving hematocrit among individual dolphins while on the Modified Diet.

TABLE 7

| Variable | Month 0 | | Month 1 | | Month 3 | | Month 6 | |
|---|---|---|---|---|---|---|---|---|
| | Modified Diet | Baseline Diet | Modified Diet | Baseline Diet | Modified Diet | Baseline Diet | Modified Diet | Baseline Diet |
| Hemoglobin | 13 ± 1 | 13 ± 1 | 14 ± 1 | 13 ± 1 | 15 ± 1* | 14 ± 1 | 15 ± 1* | 13 ± 1 |
| Hematocrit | 44 ± 5 | 44 ± 3 | 46 ± 3* | 44 ± 3 | 47 ± 2* | 45 ± 2 | 47 ± 2* | 44 ± 2 |
| RDW | 15 ± 2 | 15 ± 2 | 14 ± 1 | 15 ± 2 | 13 ± 1* | 15 ± 2 | 13 ± 1* | 16 ± 3 |
| RBC | 3.0 ± 0.3 | 3.0 ± 0.2 | 3.2 ± 0.2 | 3.0 ± 0.2 | 3.4 ± 0.2* | 3.2 ± 0.2 | 3.3 ± 0.3* | 3.1 ± 0.2 |
| MCV | 145 ± 5 | 145 ± 5 | 144 ± 5 | 143 ± 5 | 142 ± 5 | 141 ± 5 | 141 ± 5 | 142 ± 6 |
| MCH | 44 ± 1 | 44 ± 2 | 44 ± 2 | 44 ± 2 | 44 ± 2* | 43 ± 2 | 44 ± 2 | 43 ± 2 |
| MCHC | 31 ± 1 | 30 ± 1 | 31 ± 0.8 | 30 ± 1 | 31 ± 1* | 30 ± 1 | 31 ± 1* | 30 ± 1 |
| NRBC | 1.8 ± 2.9 | 1.4 ± 2.5 | 0.5 ± 0.9* | 1.2 ± 1.5 | 0.2 ± 0.6* | 1.1 ± 1.0 | 0.2 ± 0.5 | 0.7 ± 1.3 |
| PCV | 38 ± 4 | 38 ± 3 | 41 ± 2* | 39 ± 2 | 42 ± 2* | 40 ± 3 | 42 ± 2* | 39 ± 2 |

Small molecule (defined as less than 900 daltons in molecular weight) metabolites described herein can be present in serum due to either ingestion of food products or endogenous production. Thousands of small molecule metabolites can be detected and measured in serum of animals, including dolphins and humans. Metabolomics, the study of metabolites and their biologically relevant roles, is a relatively novel field of study. Due to the large number of metabolites present and high potential variation of metabolites driven by complex diets, environments, genetics, and long-term medications in human populations, identifying metabolites with the greatest biomarker and therapeutic potential has been complicated. Based upon the results using the methods of the embodiments, it can be proposed that small molecule metabolites described herein may be key players in detecting, preventing, and treating aging-associated conditions that impact quality of life and longevity.

To take advantage of these benefits, small molecule metabolites described herein can be used in a supplement, medical food, food additive, food fortifier, beverage additive, beverage fortifier, or pharmaceutical in any form, including as a tablet, encapsulated pill, gelcap pill, liquid suspension, spray, and powder. Additionally, diagnostic tests and assays for small molecule metabolites described herein in human and animal samples (including blood (serum, plasma, and erythrocyte membranes), urine, and feces) can be used to detect low small molecule metabolites and to continually monitor small molecule metabolite levels in patients. The use of small molecule metabolites can prevent, stem, and treat: aging and aging-associated conditions that impact quality of life and/or longevity, including inflammation, anemia, hyperglycemia, dyslipidemia, hyperinsulinemia, liver disease, iron overload, impaired skin integrity, wound healing, scarring, pain, allergies, sleep disorders and problems, and gastrointestinal disorders and problems, and other related conditions.

The data demonstrate a direct effect for raised levels of small molecule metabolites described herein on lowering inflammation, cholesterol, triglycerides, glucose, insulin, liver enzymes, and iron, and treating or attenuating anemia.

The data demonstrate beneficial activity of small molecule metabolites at dose-dependent (i.e. linear) concentrations ranging 1.1- to 6-fold increases above baseline serum levels, with most beneficial effects detected by at least 4-fold increases in serum levels. Dosing of small molecule metabolites to achieve these serum, plasma, cell, or tissue levels is expected to confer the observed beneficial effects.

Methods and compositions related to or applicable to aging or related conditions are discussed in the following references, which are incorporated by reference herein in their entirety: Venn-Watson S, Parry C, Baird M, Stevenson S, Carlin K, Daniels R, Smith C R, Jones R, Wells R S, Ridgway S, Jensen E D (2015) Increased dietary intake of saturated fatty acid heptadecanoic acid (C17:0) associated with decreasing ferritin and alleviated metabolic syndrome in dolphins. PLOS ONE 10(7):e0132117, Collino S (2013) Metabolic signatures of extreme longevity in Northern Italian centenarians reveal a complex remodeling of lipids, amino acids, and gut microbiota metabolism. PLOS ONE 8:e56564, Siming M (2015) Organization of the mammalian metabolome according to organ function, lineage specialization, and longevity. Cell Metab 22:332-343, Cheng (2015) Distinct metabolomic signatures are associated with longevity in humans. Nat Comm doi:10.1039/ncomms7791, Gonzalez-Covarrubias V (2013) Lipidomics of familial longevity. Aging Cell 12:426-434, Montoliu I (2014) Serum profiling of healthy aging identifies phosphor- and sphingolipid species as markers of human longevity. Aging 6:9-25, Evans C (2010) NAD+ metabolite levels as a function of vitamins and calorie restriction: evidence for different mechanisms of longevity. BMC Chem Biol 10:2, Gonzalez-Covarrubias V (2013) Lipidomics in longevity and healthy aging. Biogerontol 14:663-672, Kristal B S (2005) Metabolomics: opening another window into aging. Sci Aging Know Environ 26:pe19.

Example 3

This study examined activities of small molecules discovered in dolphin serum that had protective profiles against diseases of aging which can impact quality of life and longevity. These molecules were tested across 12 human primary cell-based systems as part of DiscoverX's BioMAP Diversity Plus program. These systems are designed to model complex human tissue and disease biology of the vasculature, skin, lung, and inflammatory tissues. Quantitative measurements of biomarker activities across this broad panel, along with comparative analysis of biological activities of known bioactive agents were used to predict and compare the efficacy and function of the four compounds. Compounds were tested at four concentrations (740 nm and 2.2, 6.7 and 20 µM).

BioMAP panels consist of human primary cell-based systems designed to model different aspects of the human body in an in vitro format. The 12 systems in the Diversity PLUS panel allow test agent characterization in an unbiased way across a broad set of systems modeling various human disease states. BioMAP systems are constructed with one or more primary cell types from healthy human donors, with stimuli (such as cytokines or growth factors) added to capture relevant signaling networks that naturally occur in human tissue or pathological conditions. Vascular biology is modeled in both a Th1 (3C system) and a Th2 (4H system) inflammatory environment, as well as in a Th1 inflammatory state specific to arterial smooth muscle cells (CASM3C system). Additional systems recapitulate aspects of the systemic immune response including monocyte-driven Th1 inflammation (LPS system) or T cell stimulation (SAg system), chronic Th1 inflammation driven by macrophage activation (lMphg system) and the T cell-dependent activation of B cells that occurs in germinal centers (BT system). The BE3C system (Th1) and the BF4T system (Th2) represent airway inflammation of the lung, while the MyoF system models myofibroblast-lung tissue remodeling. Lastly, skin biology is addressed in the KF3CT system modeling Th1 cutaneous inflammation and the HDF3CGF system modeling wound healing.

Each test agent generates a signature BioMAP profile that is created from the changes in protein biomarker readouts within individual system environments. Biomarker readouts (7-17 per system) are selected for therapeutic and biological relevance, are predictive for disease outcomes or specific drug effects and are validated using agents with known mechanism of action (MoA). Each readout is measured quantitatively by immune-based methods that detect protein (e.g., ELISA) or functional assays that measure proliferation and viability. BioMAP readouts are diverse and include cell surface receptors, cytokines, chemokines, matrix molecules and enzymes. In total, the Diversity PLUS panel contains 148 biomarker readouts that capture biological changes that occur within the physiological context of the particular BioMAP system. Specific BioMAP activities have been correlated to in vivo biology, and multiparameter BioMAP profiles have been used to distinguish compounds based on MoA and target selectivity across diverse physiological systems.

Figure 2:
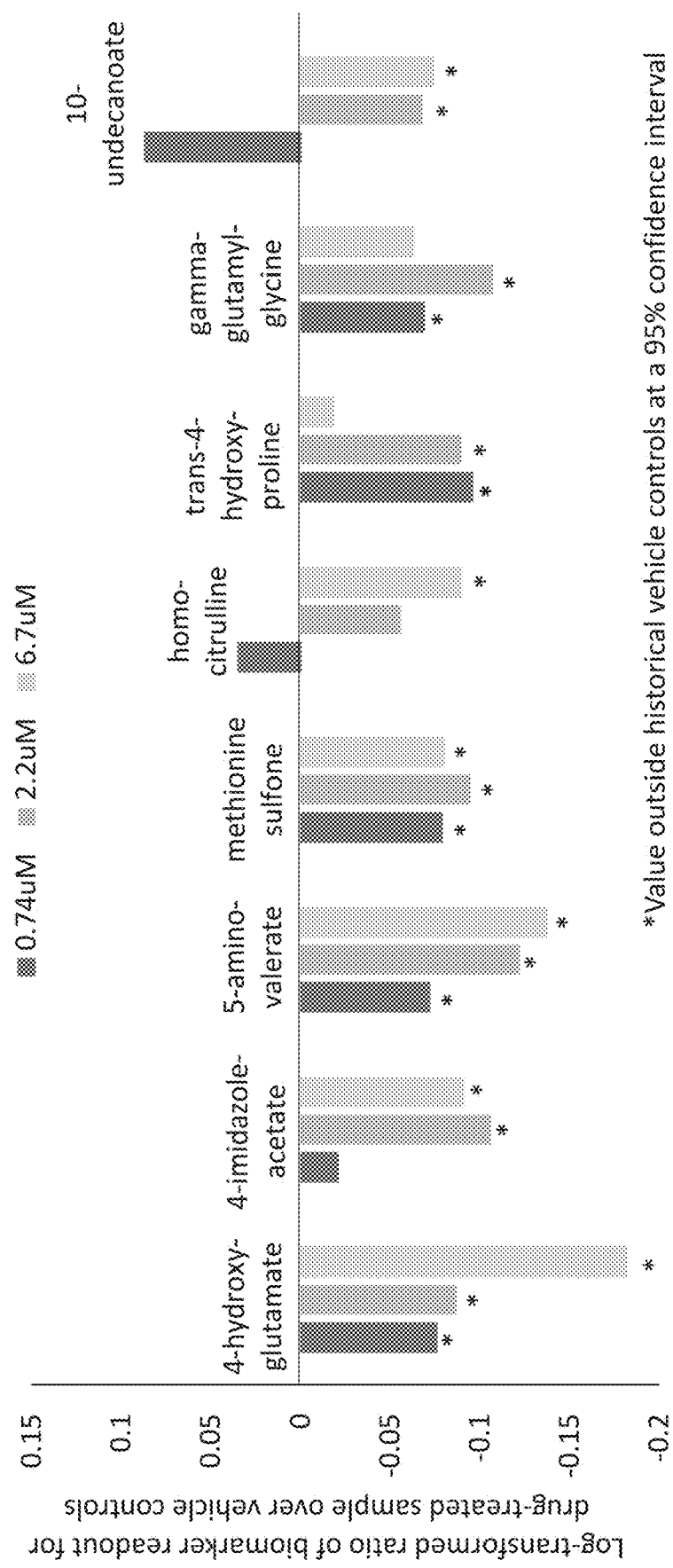
FIG. 2 provides data regarding the impact of dolphin serum-based compounds on t-cell proliferation in a human cell system mimicking t-cell driven chronic inflammation and autoimmune diseases.
Figure 3:
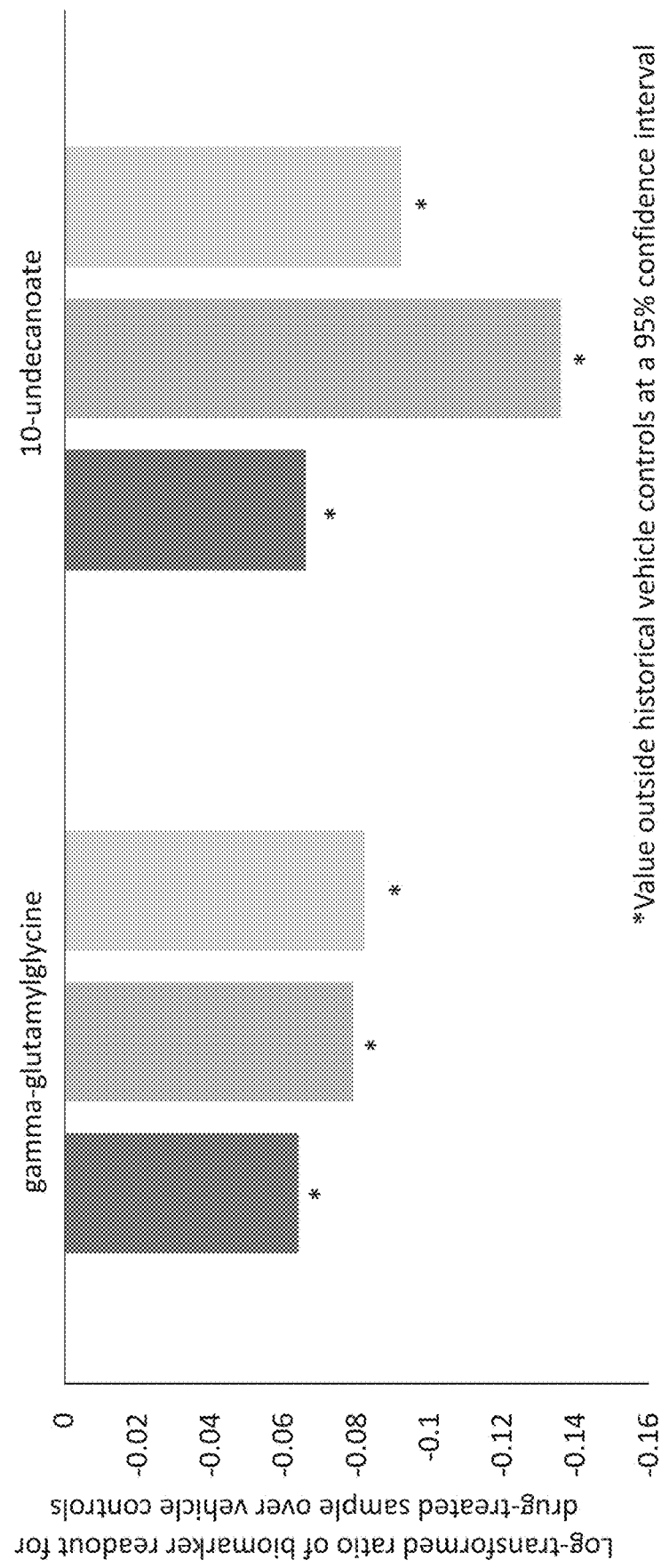
FIG. 3 provides data regarding the impact of dolphin serum-based compounds on CD40 in a human cell system mimicking t-cell driven chronic inflammation and autoimmune diseases.

All nine dolphin-based molecules tested for their potential impact on 148 disease biomarkers measured across 12 cell systems, seven (78%) successfully demonstrated activity across a variety of systems mimicking inflammation, which was consistent with their protective profiles in the dolphin model. Eight compounds (4-hydroxyglutamate, 4-imidazoleacetate, 5-aminovalerate, methionine sulfone, homocitrulline, trans-4-hydroxyproline, gamma-glutamylglycine, and 10-undecanoate), at concentrations ranging from 740 nm to 6.7 µM, decreased T cell proliferation in a human cell system mimicking T-cell driven chronic inflammation and autoimmune diseases (FIG. 2). Gamma-glutamylglycine and 10-undecanoate also lowered CD40 at concentrations of 740 nm, 2.2 µM, and 6.7 µM in this system (FIG. 3).

Figure 4:
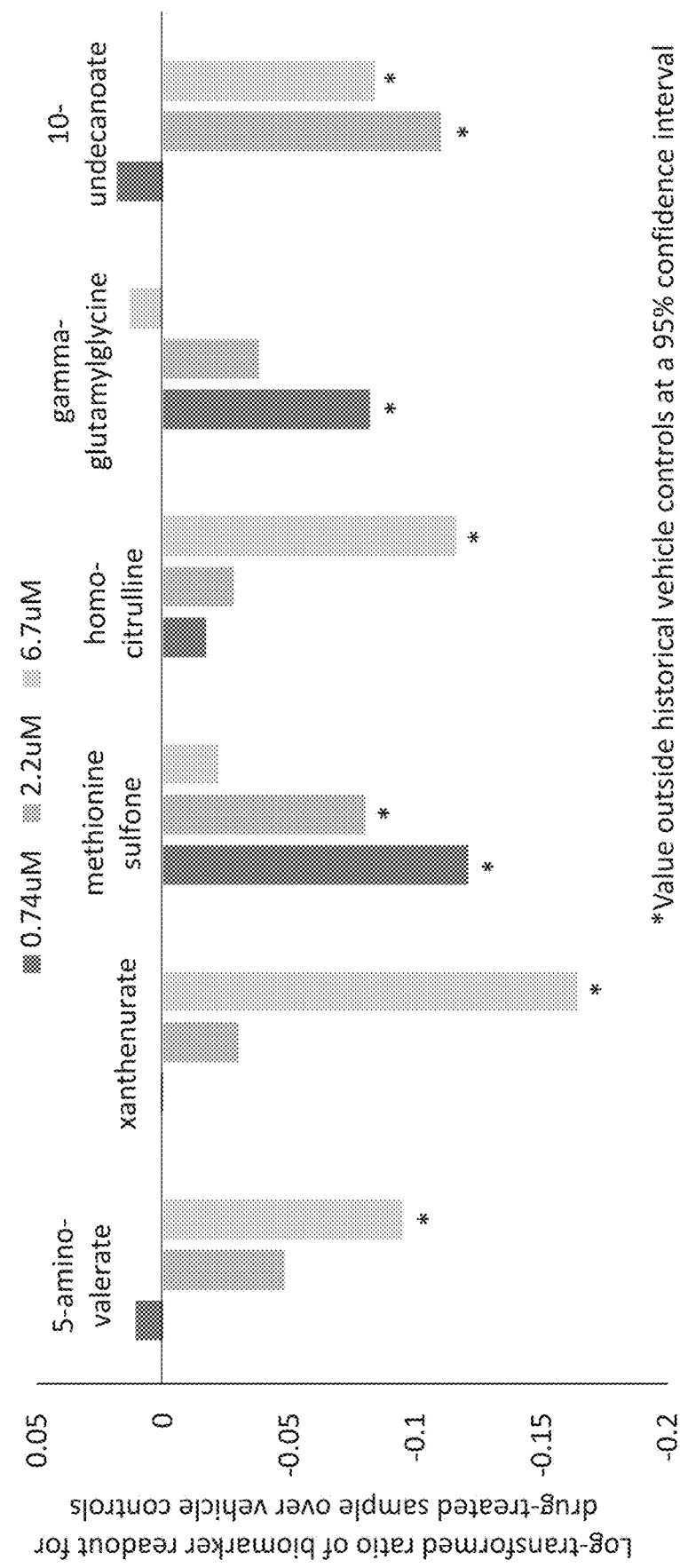
FIG. 4 provides data regarding the impact of dolphin serum-based compounds on prostaglandin E2 secretion in a human cell system mimicking t-cell and monocyte driven chronic inflammation and cardiovascular diseases.
Figure 5:
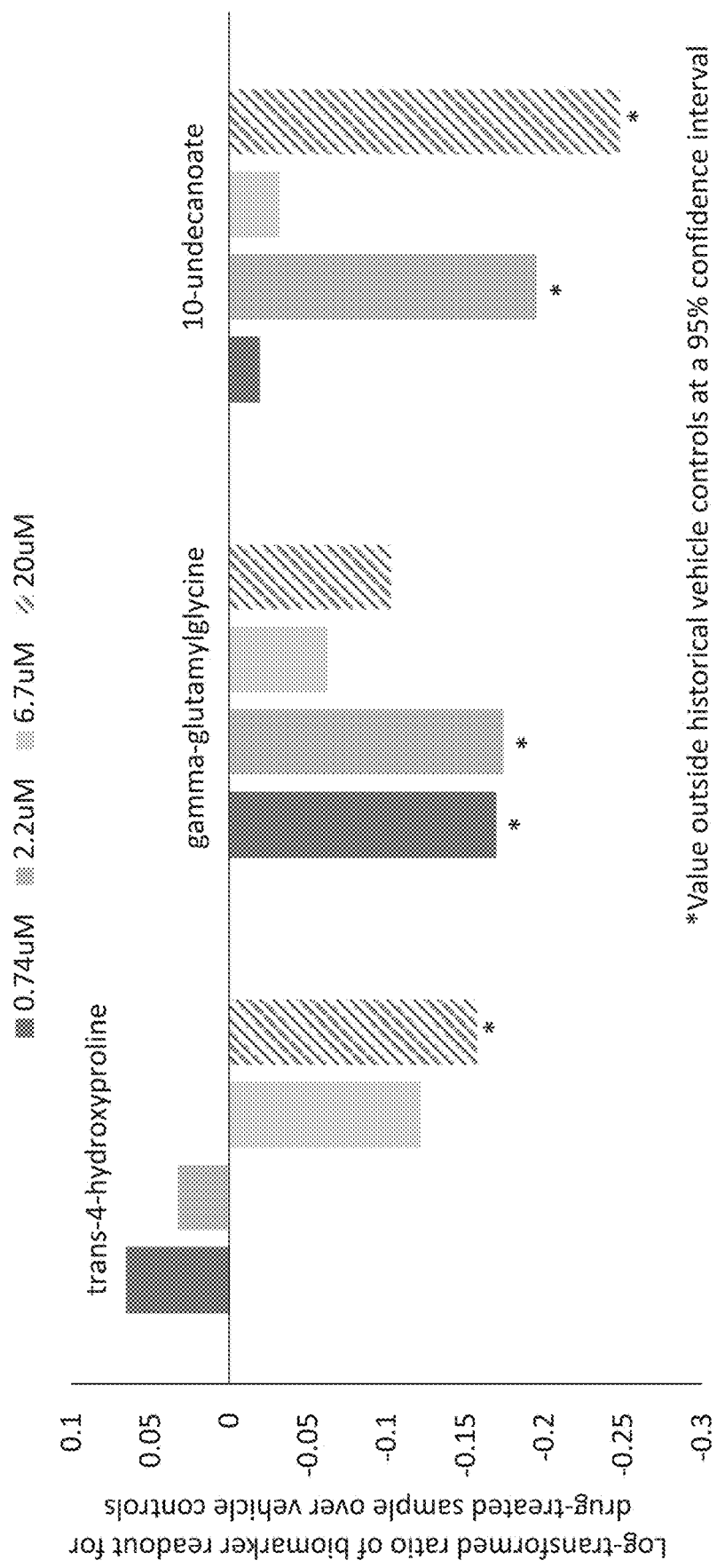
FIG. 5 provides data regarding the impact of dolphin serum-based compounds on IL-17A in a human cell system mimicking asthma, autoimmunity, and allergy.
Figure 6:
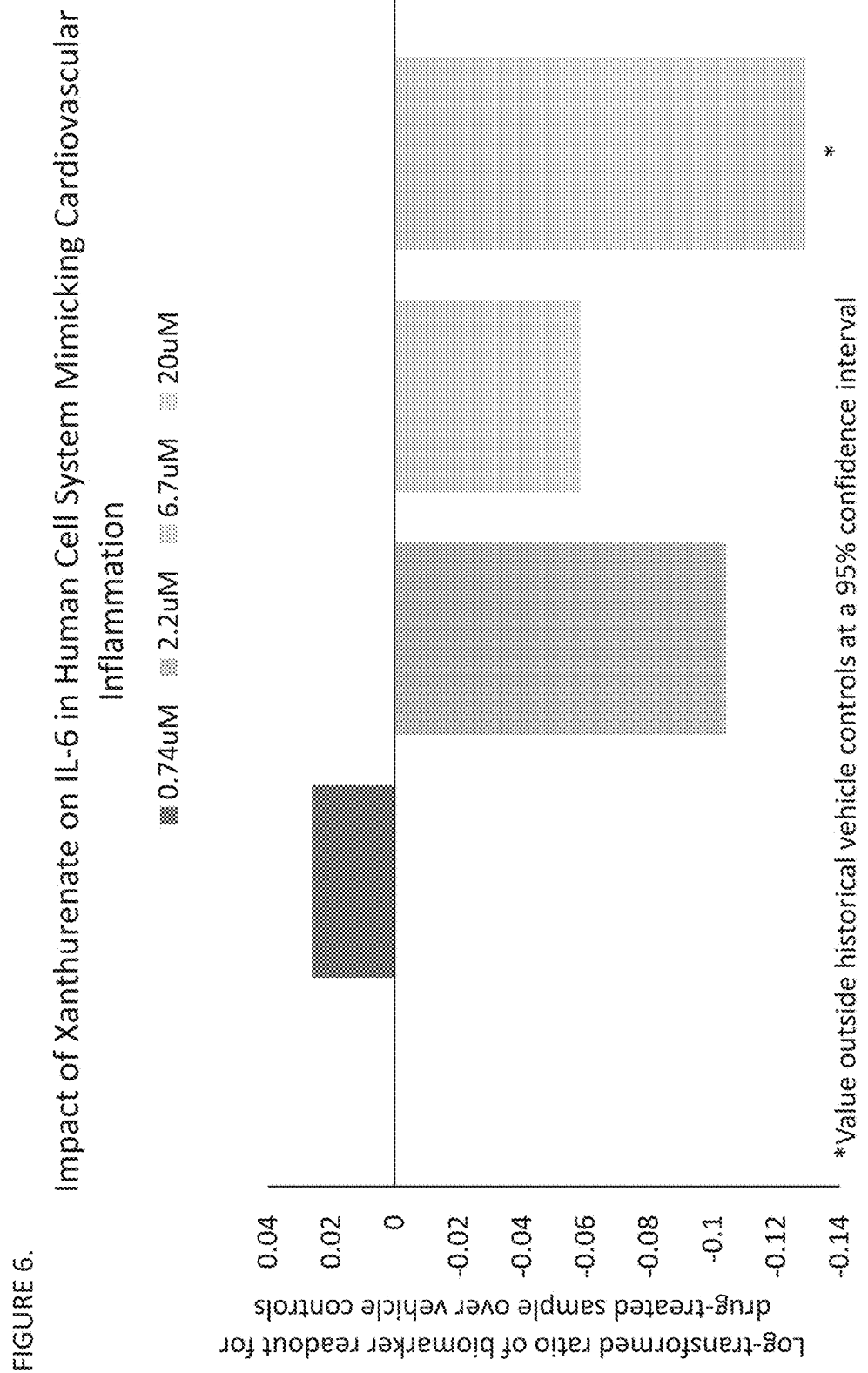
FIG. 6 provides data regarding the impact of xanthurenate on IL-6 in a human cell system mimicking cardiovascular inflammation.

Most of the tested compounds (5-aminovalerate, xanthurenate, methionine sulfone, homocitrulline, gamma-glutmylglycine, and 10-undecanoate) lowered secretion of prostaglandin E2 (PGE2) in a human cell system mimicking T-cell and monocyte driven chronic inflammation and cardiovascular diseases (FIG. 4). Trans-4-hydroxyproline, gamma-glutamylglycine, and 10-undecanoate lowered interleukin 17A (IL-17A) in a human cell system mimicking asthma, autoimmunity and allergies (FIG. 5). Xanthurenate lowered IL-6 in a human cell system mimicking cardiovascular inflammation (FIG. 6).

Figure 7:
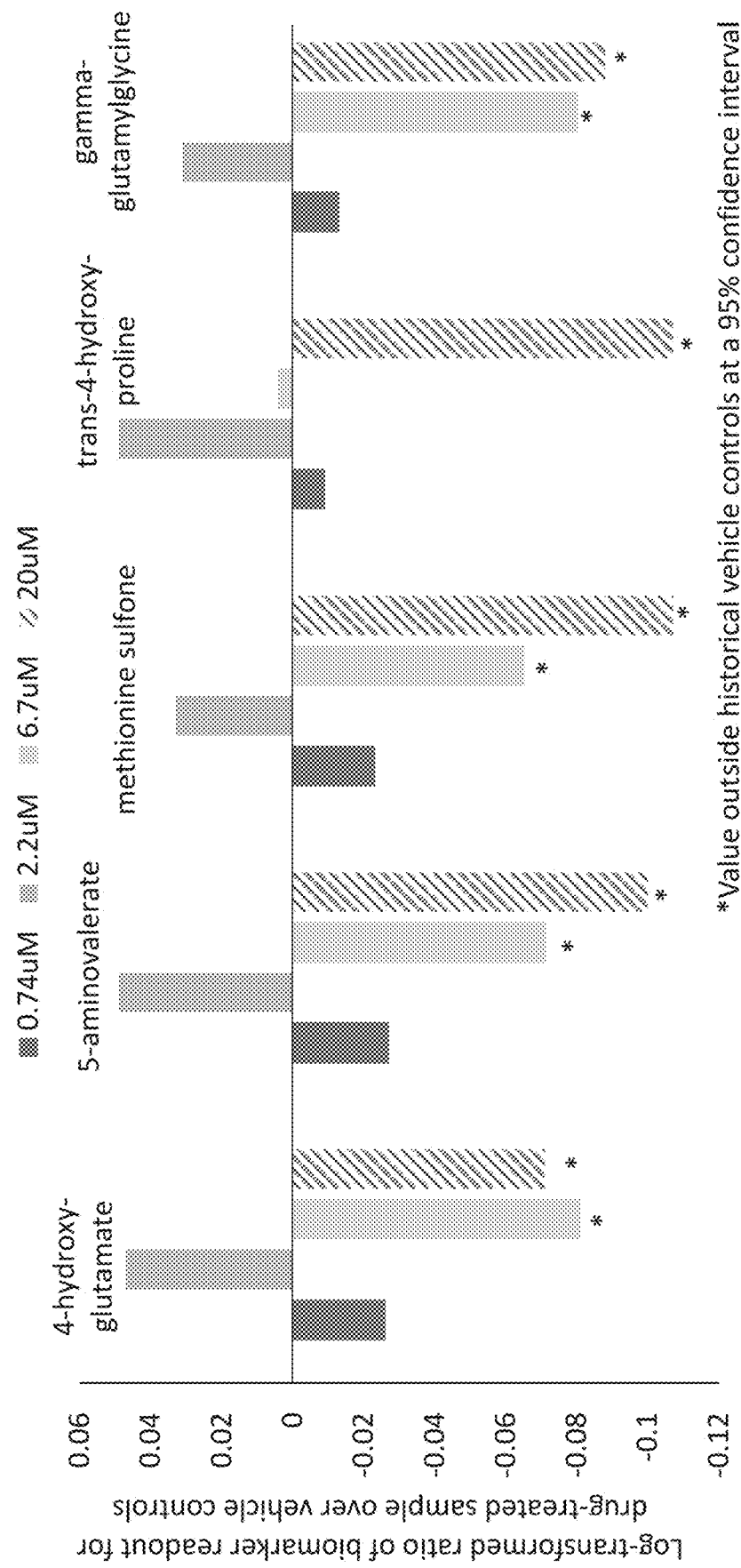
FIG. 7 provides data regarding the impact of dolphin serum-based compounds on decorin in a human cell system mimicking wound healing, remodeling, fibrosis, and chronic inflammation.
Figure 8:
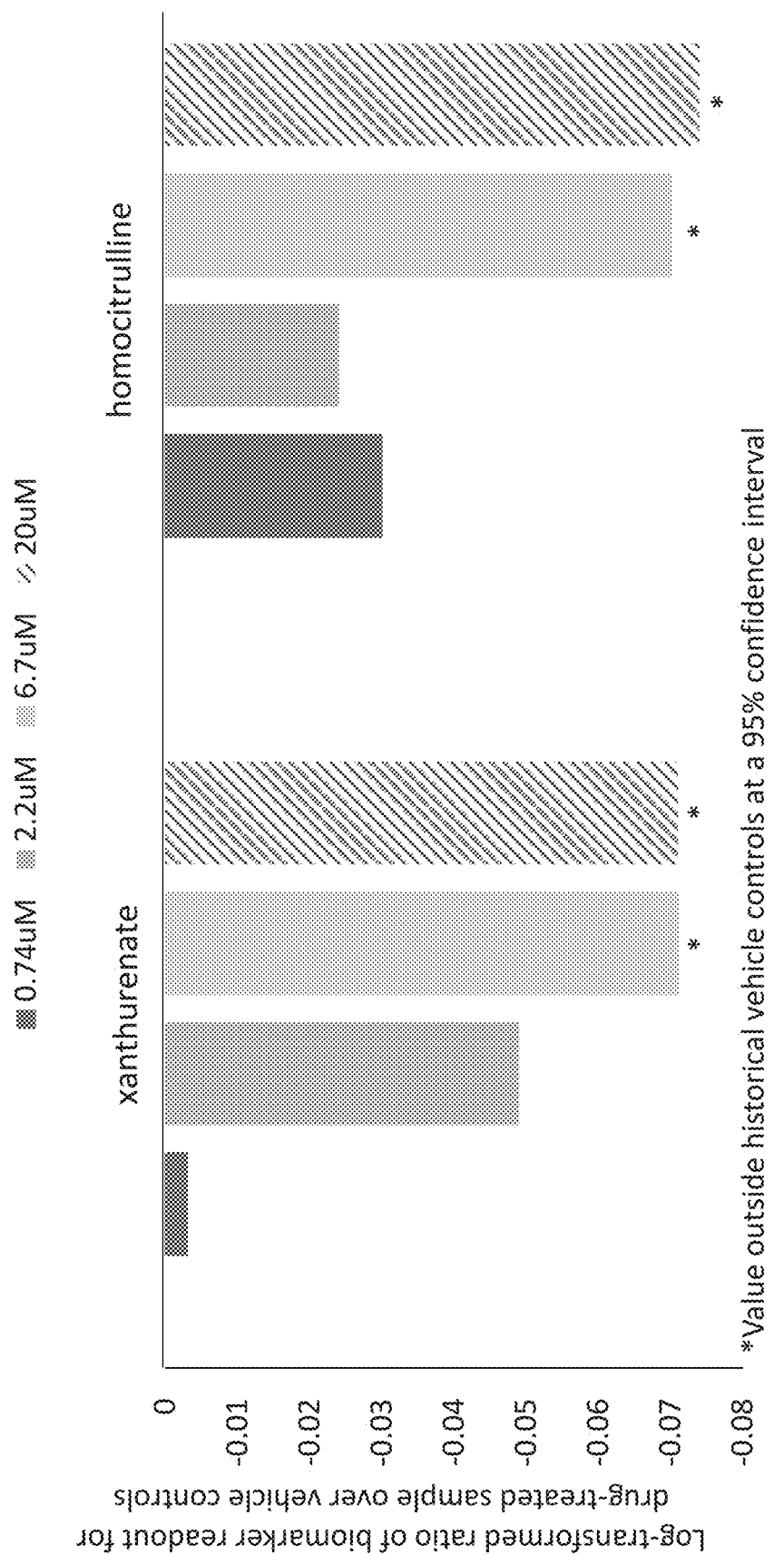
FIG. 8 provides data regarding the impact of dolphin serum-based compounds on IL-8 in a human cell system mimicking wound healing, remodeling, fibrosis, and chronic inflammation.

Seven of nine tested compounds demonstrated inhibitory activity of either decorin (4-hydroxyglutamate, 5-aminovalerate, methionine sulfone, trans-4-hydroxyproline and gamma-glutamylglycine) or interleukin 8 (IL-8) (xanthurenate and homocitrulline) in a human cell system mimicking wound healing, remodeling, fibrosis and chronic inflammation (FIGS. 7 and 8).

In summary, all molecules discovered to have protective profiles against inflammation and other diseases of aging in dolphins and that were also tested in human cell systems mimicking inflammation demonstrated in vitro anti-inflammatory activity. This study supports that molecules discovered in serum with protective profiles in dolphins effectively translate to clinically relevant and beneficial activity in human model diseases of aging. Further, different dolphin-based compounds may be selected as therapeutics based on specific diseases being targeted. As an example, a general summary of targeted diseases and mechanisms for selected compounds are provided in the table of FIG. 9.

Example 4

In order to demonstrate that our screened compounds have activity relevant to multiple aging-associated diseases, human cell-based studies were completed using a selected subset of synthesized compounds. As a proof of concept, 14 compounds were selected from our compound library based on predicted efficacy in lowering inflammation in dolphins. Pure synthetic forms of these compounds were screened for cell-based activities (relevant to multiple aging-associated diseases and diseases that may impact longevity) using twelve different human primary cell systems mimicking various disease states (TABLE 8—description of primary human cell systems used to screen selected compounds in library).

Methods

The Diversity PLUS panel allows test agent characterization in an unbiased way across a broad set of systems modeling various human disease states. These systems are designed to model complex human tissue and disease biology of the vasculature, skin, lung, and inflammatory tissues. Quantitative measurements of 148 biomarker activities across this broad panel, along with comparative analysis of biological activities from known bioactive agents, were used to predict and compare the efficacy and function of each selected compound at four concentrations (740 nm and 2.2, 6.7 and 20 µM).

BioMAP systems are constructed with one or more primary cell types from healthy human donors, with stimuli (such as cytokines or growth factors) added to capture relevant signaling networks that naturally occur in human tissue or pathological conditions. Vascular biology is modeled in both a Th1 (3C system) and a Th2 (4H system) inflammatory environment, as well as in a Th1 inflammatory state specific to arterial smooth muscle cells (CASM3C system). Additional systems recapitulate aspects of the systemic immune response including monocyte-driven Th1 inflammation (LPS system) or T cell stimulation (SAg system), chronic Th1 inflammation driven by macrophage activation (lMphg system) and the T cell-dependent activation of B cells that occurs in germinal centers (BT system). The BE3C system (Th1) and the BF4T system (Th2) represent airway inflammation of the lung, while the MyoF system models myofibroblast-lung tissue remodeling. Lastly, skin biology is addressed in the KF3CT system modeling Th1 cutaneous inflammation and the HDF3CGF system modeling wound healing.

Each test agent generates a signature BioMAP profile that is created from the changes in protein biomarker readouts within individual system environments. Biomarker readouts (7-17 per system) are selected for therapeutic and biological relevance, are predictive for disease outcomes or specific drug effects and are validated using agents with known mechanism of action (MoA). Each readout is measured quantitatively by immune-based methods that detect protein (e.g., ELISA) or functional assays that measure proliferation and viability. BioMAP readouts are diverse and include cell surface receptors, cytokines, chemokines, matrix molecules and enzymes. In total, the Diversity PLUS panel contains 148 biomarker readouts that capture biological changes that occur within the physiological context of the particular BioMAP system. Specific BioMAP activities have been correlated to in vivo biology, and multiparameter BioMAP profiles have been used to distinguish compounds based on MoA and target selectivity across diverse physiological systems.

Activated BioMAP systems were incubated with each compound for 24 to 72 hours. Protein-based biomarkers from activated cell systems were measured and compared with non-treated control systems. Biomarker activities were noted as 'significant' when at least one compound concentration was outside of the significance envelope and had an effect size >20% (log 10 ratio) >0.1. The BioMAP assays do not currently have cell systems to model metabolic diseases, including hyperinsulinemia, hyperglycemia, and dyslipidemia; thus, these assays were limited to assessing compounds' potential anti-inflammatory and antifibrotic properties.

Compounds included in this study represented a variety of amino acids, peptides and lipids across multiple pathways. Specifically, the following 14 compounds were tested for cell-based therapeutic activities: 4-hydroxyglutamate (amino acid, glutamate metabolism), 4-imidazoleacetate (amino acid, histidine metabolism), 5-aminovalerate (amino acid, lysine metabolism), xanthurenate (amino acid, tryptophan metabolism), methionine sulfone (amino acid, methionine metabolism), gamma-glutamylglycine (peptide, gamma-glutamyl amino acid), gamma-glutamylglutamine (peptide, gamma-glutamyl amino acid), 10-undecanoate (lipid, medium chain fatty acid), pentadecanoylcarnitine (lipid, fatty acid metabolism/acyl carnitine), lignoceroylcarnitine (lipid, fatty acid metabolism/acyl carnitine), 1-palmitoyl-2-arachidonoyl-GPC (16:0/20:4n6) (lipid, glycerophosphatidylcholine), N-acetylhistamine (amino acid, histidine metabolism), 10-heptanoate (lipid, long chain fatty acid), and pentadecanoic acid (lipid, long chain fatty acid).

Results

All compounds successfully demonstrated therapeutic activities, between concentrations of 0.7 and 20 µM, across multiple cell systems mimicking a variety of aging-associated diseases (TABLE 9—therapeutic activities of selected compounds in primary human cell systems mimicking various aging-associated diseases). Relevant cell-based disease systems that were successfully attenuated by our selected compounds represented Th1- and Th2-type inflammation, T-cell dependent B cell proliferation, allergy, asthma, atherosclerosis, autoimmunity, chronic inflammation, chronic obstructive pulmonary disease (COPD), Crohn's disease, cutaneous responses to tissue damage, fibrosis, hematological oncology, metabolic diseases, organ transplantation, psoriasis, pulmonary fibrosis, pulmonary responses to respiratory infections, restenosis, rheumatoid arthritis, sarcoidosis, stromal biology in tumors, systemic lupus erythematosus (SLE), ulcerative colitis, and vascular inflammation. Summary examples of diseases targeted by the selected compounds are provided (TABLE 10—Examples of diseases involving Th2 type inflammation or T-cell dependent B cell proliferation targeted by selected compounds, based on human primary cell phenotypic profiling activity data; TABLE 11—Examples of diseases involving Th1 type inflammation targeted by selected compounds, based on human primary cell phenotypic profiling activity data; TABLE 12—Examples of diseases targeted by selected compounds, based on human primary cell phenotypic profiling activity data).

Further, based on this study's findings, diseases that are driven or exacerbated by the following factors may be attenuated or treated by selected compounds: alpha smooth muscle actin (αSMA), CD40, CD69, collagen I, collagen III, decorin, e-selectin, eotaxin 3 (CCL26), fibroblast proliferation, human leukocyte antigen-DR isotype (HLA-DR), immunoglobulin G, interferon gamma-induced protein 10 (IP-10/CXCL10), interferon-inducible T cell alpha chemoattractant (I-TAC/CXCL11), interleukin (IL)-1, IL-1α, IL-2, IL-6, IL-8 (CXCL8), IL-10, IL-17A, IL-17F, keratin 8/81, macrophage colony-stimulating factor (M-CSF), matrix metalloproteinase (MMP)-1, MMP-9, monocyte chemoattractant protein 1 (MCP-1), monokine induced by gamma interferon (MIG/CXCL9), plasminogen activation inhibitor 1 (PAI-1), prostaglandin E2 (PGE2), serum amyloid A, T or B cell proliferation, tissue plasminogen activator (tPA), tumor necrosis factor alpha (TNFα), vascular cell adhesion molecule (VCAM-1), vascular endothelial growth factor 2 (VEGFR2).

In summary, this study demonstrated that multiple compounds, including amino acids, lipids, and peptides across multiple pathways that were identified in the dolphin metabolome and were predicted to have therapeutic activities relevant to aging-associated diseases, successfully demonstrated disease-modifying activities in human cell systems mimicking a variety of disease states.

TABLE 8

| Cell system name | Human cell types | Stimulation | Disease/tissue relevance | System description |
|---|---|---|---|---|
| 4H | Venular endothelial cells | IL-4, histamine | Th2-type inflammatory conditions: autoimmunity, allergy, asthma, ulcerative colitis | Models Th2 type vascular inflammation that promotes mast cell, basophil, eosinophil, T and B cell recruitment |
| LPS | Venular endothelial cells, peripheral blood mononuclear cells | TLR4 ligand | Chronic inflammatory conditions where monocytes play a key role: atherosclerosis, restenosis, rheumatoid arthritis, metabolic diseases | Models Th1 type chronic inflammation and monocyte activation process |
| SAg | Venular endothelial cells, peripheral blood mononuclear cells | TCR ligands (1X) | T-cell driven inflammatory conditions including organ transplantation, rheumatoid arthritis, psoriasis, Crohn's disease and hematological oncology | Models Th1 type chronic inflammation and T cell effector responses related to T cell proliferation and activation |
| BT | Peripheral blood mononuclear cells, B cells | α-IgM, TCR ligands (0.001X, sub-mitogenic levels) | Diseases driven by B-cell activation and antibody production: systemic lupus erythematosus, hematological oncology, autoimmune indications, asthma and allergy | Models T cell dependent B cell proliferation, activation and class switching that occurs in the germinal centers of secondary lymphoid organs |
| BF4T | Bronchial epithelial cells, dermal fibroblasts | IL-4, TNF-α | Allergy and asthma, pulmonary fibrosis, COPD exacerbations | Models Th2 type lung inflammation and environment that promotes recruitment of eosinophils, mast cells and basal cells as well as effector memory T cells |
| BE3C | Bronchial epithelial cells | IL-1β, IFNγ, TNFα | Sarcoidosis and pulmonary responses to respiratory infections | Models Th1 type lung inflammation and environment that promotes monocyte and T cell adhesion and recruitment |
| CASM3C | Coronary artery smooth muscle cells | IL-1β, TNFα, IFNγ | Chronic inflammatory diseases, vascular inflammation and restenosis | Models Th1 type vascular inflammation and environment that promotes monocyte and T cell recruitment |
| HDF3CGF | Dermal fibroblasts | IFNγ, TNFα, IL-1β, EGF, bFGF, PDGF-BB | Various diseases including fibrosis, rheumatoid arthritis, psoriasis and stromal biology in tumors | Models wound healing and matrix/tissue remodeling in the context of Th1-type inflammation |
| KF3CT | Keratinocytes, dermal fibroblasts | IL-1β, IFNγ, TGFβ, TNFα | Cutaneous responses to tissue damage caused by mechanical, chemical or infectious agents; certain states of psoriasis and dermatitis | Models Th1 type cutaneous inflammation and environment that promotes monocyte and T cell adhesion and recruitment |

TABLE 8-continued

| Cell system name | Human cell types | Stimulation | Disease/tissue relevance | System description |
|---|---|---|---|---|
| MyoF | Lung fibroblasts | TGFβ, TNFα | Multiple fibrotic diseases | Models general myofibroblast differentiation and tissue remodeling; readout captures impacts on translationally relevant matrix remodeling, tissue repair and inflammation related to responses in fibrotic tissue |
| /Mphg | Macrophages, venular endothelial cells | TLR2 ligand | Inflammatory conditions where monocytes play a key role including atherosclerosis, restenosis, rheumatoid arthritis, and other chronic inflammatory conditions | Models Th1 type chronic inflammation and macrophage activation responses |

TABLE 9

| Compound | Human primary cell-based system | Disease systems | Biomarkers significantly lowered by compound | Active concentrations (μM) | Significant log10 reduction of biomarkers in treated systems compared to nontreated controls |
|---|---|---|---|---|---|
| 1-palmitoyl-2-arachidonoyl-GPC | BT | Asthma, oncology, autoimmunity, allergy | Secreted interleukin 17F (IL-17F) | 2.2 | −0.12 |
| | | | | 20.0 | −0.24 |
| | | | Secreted interleukin 2 (IL-2) | 20.0 | −0.27 |
| | | | Secreted tumor necrosis factor alpha (TNFα) | 20.0 | −0.16 |
| | BF4T | Fibrosis, lung inflammation, asthma, allergy | Eotaxin 3 (CCL26) | 2.2 | −0.11 |
| | | | | 6.7 | −0.24 |
| | | | | 20.0 | −0.58 |
| | | | Plasminogen activation inhibitor 1 (PAI-1) | 6.7 | −0.07 |
| | | | | 20.0 | −0.19 |
| | BE3C | COPD, lung inflammation | Keratin 8/18 | 6.7 | −0.08 |
| | | | Interleukin 8 (IL-8)/CXCL8 | 20.0 | −0.12 |
| | | | Matrix metalloproteinase 9 (MMP-9) | 20.0 | −0.11 |
| | | | Plasminogen activation inhibitor 1 (PAI-1) | 20.0 | −0.12 |
| | HDF3CGF | Fibrosis, chronic inflammation | Plasminogen activation inhibitor 1 (PAI-1) | 20.0 | −0.11 |
| | MyoF | Wound healing, matrix remodeling, fibrosis, chronic inflammation | Alpha smooth muscle actin (αSMA) | 0.7 | −0.07 |
| | | | | 2.2 | −0.09 |
| | | | | 6.7 | −0.10 |
| | | | | 20.0 | −0.18 |
| | /Mphg | Chronic inflammation, restenosis, cardiovascular disease | Monocyte chemoattractant protein 1 (MCP-1) | 2.2 | −0.12 |
| | | | | 6.7 | −0.13 |
| | | | | 20.0 | −0.18 |
| | | | CD69 | 20.0 | −0.11 |
| | | | Secreted interleukin 10 (IL-10) | 6.7 | −0.18 |
| 4-hydroxyglutamate | SAg | Chronic inflammation, autoimmune disease | T cell proliferation | 0.7 | −0.08 |
| | | | | 2.2 | −0.09 |
| | | | | 6.7 | −0.18 |
| | BT | Asthma, oncology, autoimmunity, allergy | Secreted interleukin 17F (IL-17F) | 0.7 | −0.16 |
| 4-imidazoleacetate | SAg | Chronic inflammation, autoimmune disease | T cell proliferation | 2.2 | −0.11 |
| | | | | 6.7 | −0.09 |
| | | | | 20.0 | −0.09 |
| | BT | Asthma, oncology, autoimmunity, allergy | Secreted interleukin 17F (IL-17F) | 0.7 | −0.16 |
| 5-aminovalerate | SAg | Chronic inflammation, autoimmune disease | T cell proliferation | 0.7 | −0.7 |
| | | | | 2.2 | −0.12 |
| | | | | 6.7 | −0.14 |
| | LPS | Chronic inflammation, cardiovascular disease | Secreted prostaglandin E2 (PGE2) | 6.7 | −0.10 |

TABLE 9-continued

| Compound | Human primary cell-based system | Disease systems | Biomarkers significantly lowered by compound | Active concentrations (µM) | Significant log10 reduction of biomarkers in treated systems compared to nontreated controls |
|---|---|---|---|---|---|
| | BT | Asthma, oncology, autoimmunity, allergy | Tumor necrosis factor alpha (TNFα) | 6.7 | −0.11 |
| | MyoF | Wound healing, matrix remodeling, fibrosis, chronic inflammation | Decorin | 6.7 | −0.07 |
| | | | | 20.0 | −0.10 |
| 10-heptadecanoate | BT | Asthma, oncology, autoimmunity, allergy | Secreted interleukin 2 (IL-2) | 6.7 | −0.11 |
| | BF4T | Fibrosis, lung inflammation, asthma, allergy | Eotaxin 3 (CCL26) | 2.2 | −0.10 |
| | | | | 6.7 | −0.13 |
| | | | | 20.0 | −0.31 |
| | CASM3C | Cardiovascular inflammation, restenosis | Serum amyloid A | 2.2 | −0.13 |
| | HDF3CGF | Fibrosis, chronic inflammation | Vascular cell adhesion molecule 1 (VCAM-1) | 6.7 | −0.17 |
| | | | Macrophage colony-stimulating factor (M-CSF) | 6.7 | −0.1 |
| 10-undecanoate | LPS | Chronic inflammation, cardiovascular disease | Secreted prostaglandin E2 (PGE2) | 0.7 | −0.11 |
| | | | | 2.2 | −0.08 |
| | | | | 6.7 | −0.20 |
| | | | CD40 | 20.0 | −0.11 |
| | BT | Asthma, oncology, autoimmunity, allergy | Secreted interleukin 17A (IL-17A)? | 2.2 | −0.25 |
| | | | | 20.0 | −0.20 |
| | | | Tumor necrosis factor alpha (TNFα) | 20.0 | −0.12 |
| 10-undecanoate | SAg | Chronic inflammation, autoimmune disease | CD40 | 0.7 | −0.07 |
| | | | | 2.2 | −0.14 |
| | | | | 6.7 | −0.09 |
| | | | | 20.0 | −0.11 |
| | BE3C | COPD, lung inflammation | Tissue plasminogen activator (tPA) | 2.2 | −0.08 |
| | | | | 6.7 | −0.11 |
| | | | | 20.0 | −0.12 |
| | HDF3CGF | Fibrosis, chronic inflammation | Macrophage colony-stimulating factor (M-CSF) | 0.7 | −0.11 |
| | | | | 2.2 | −0.07 |
| | /Mphg | Chronic inflammation, restenosis, cardiovascular disease | Secreted interleukin 10 (IL-10) | 20.0 | −0.21 |
| Gamma-glutamylglutamine | /Mphg | Chronic inflammation, restenosis, cardiovascular disease | Monocyte chemoattractant protein 1 (MCP-1) | 0.7 | −0.18 |
| | | | | 2.2 | −0.10 |
| | | | Interleukin 1 alpha (IL-1α) | 20.0 | −0.16 |
| | SAg | Chronic inflammation, autoimmune disease | Monocyte chemoattractant protein 1 (MCP-1) | 0.7 | −0.10 |
| | BT | Asthma, oncology, autoimmunity, allergy | Secreted interleukin 6 (IL-6) | 20.0 | −0.13 |
| | CASM3C | Cardiovascular inflammation, restenosis | Serum amyloid A | 6.7 | −0.11 |
| | | | Vascular cell adhesion molecule 1 (VCAM-1) | 20.0 | −0.15 |
| | HDF3CGF | Fibrosis, chronic inflammation | Collagen III | 20.0 | −0.10 |
| Gamma-glutamylglycine | SAg | Chronic inflammation, autoimmune disease | T cell proliferation | 6.7 | −0.11 |
| | | | | 20.0 | −0.07 |
| | BT | Asthma, oncology, autoimmunity, allergy | Secreted interleukin 17A | 0.7 | −0.17 |
| | | | | 2.2 | −0.17 |
| Lignoceroylcarnitine | BT | Asthma, oncology, autoimmunity, allergy | B cell proliferation | 0.7 | −0.15 |
| | | | | 2.2 | −0.09 |
| | | | | 6.7 | −0.09 |
| | | | | 20.0 | −0.07 |
| | | | Secreted interleukin 17A (IL-17A) | 20.0 | −0.25 |
| | | | Secreted interleukin 2 (IL-2) | 6.7 | −0.11 |
| | | | Secreted interleukin 6 (IL-6) | 20.0 | −0.13 |
| | | | Secreted tumor necrosis factor alpha (TNFα) | 2.2 | −0.10 |
| | BF4T | Fibrosis, lung inflammation, asthma allergy | Keratin 8/18 | 0.7 | −0.07 |
| | | | | 2.2 | −0.07 |
| | | | | 6.7 | −0.09 |
| | | | | 20.0 | −0.11 |
| | BE3C | COPD, lung inflammation | Interferon-inducible T cell alpha chemoattractant (I-TAC)/CXCL11 | 0.7 | −0.05 |
| | | | | 2.2 | −0.12 |
| | MyoF | Wound healing, matrix remodeling, fibrosis, chronic inflammation | Alpha smooth muscle actin (αSMA) | 0.7 | −0.08 |
| | | | | 2.2 | −0.13 |
| | | | | 6.7 | −0.18 |
| | | | | 20.0 | −0.20 |

TABLE 9-continued

| Compound | Human primary cell-based system | Disease systems | Biomarkers significantly lowered by compound | Active concentrations (μM) | Significant log10 reduction of biomarkers in treated systems compared to nontreated controls |
|---|---|---|---|---|---|
| | /Mphg | Chronic inflammation, restenosis, cardiovascular disease | Monocyte chemoattractant protein 1 (MCP-1) | 2.2<br>6.7<br>20.0 | −0.29<br>−0.16<br>−0.11 |
| Methionine sulfone | LPS | Chronic inflammation, cardiovascular disease | Secreted prostaglandin E2 (PGE2) | 0.7<br>2.2 | −0.12<br>−0.08 |
| | CASM3C | Cardiovascular inflammation, restenosis | Vascular cell adhesion molecule 1 (VCAM-1) | 0.7<br>2.2 | −0.10<br>−0.09 |
| | HDF3CGF | Fibrosis, chronic inflammation | Monocyte chemoattractant protein 1 (MCP-1) | 6.7 | −0.24 |
| | MyoF | Wound healing, matrix remodeling, fibrosis, chronic inflammation | Decorin | 6.7<br>20.0 | −0.07<br>−0.11 |
| N-acetylhistamine | BT | Asthma, oncology, autoimmunity, allergy | B cell proliferation | 2.2<br>6.7<br>20.0 | −0.12<br>−0.06<br>−0.08 |
| | | | Secreted interleukin 17A (IL-17A) | 20.0 | −0.19 |
| | | | Secreted interleukin 17F (IL-17F) | 20.0 | −0.42 |
| | HDF3CGF | Fibrosis, chronic inflammation | Vascular cell adhesion molecule 1 (VCAM-1) | 6.7<br>20.0 | −0.08<br>−0.15 |
| | | | Collagen III | 20.0 | −0.13 |
| | MyoF | Wound healing, matrix remodeling, fibrosis, chronic inflammation | Alpha smooth muscle actin (αSMA) | 0.7<br>2.2<br>6.7<br>20.0 | −0.05<br>−0.06<br>−0.11<br>−0.09 |
| | /Mphg | Chronic inflammation, restenosis, cardiovascular disease | Monocyte chemoattractant protein 1 (MCP-1) | 2.2 | −0.26 |
| Pentadecanoic acid | SAg | Chronic inflammation, autoimmune disease | Monocyte chemoattractant protein 1 (MCP-1) | 6.7<br>20.0 | −0.18<br>−0.15 |
| | BT | Asthma, oncology, autoimmunity, allergy | Secreted immunoglobulin G (IgG) | 6.7<br>20.0 | −0.17<br>−0.55 |
| | | | Secreted interleukin 17A (IL-17A) | 2.2<br>20.0 | −0.25<br>−0.29 |
| | | | Secreted interleukin 17F (IL-17F) | 2.2<br>20.0 | −0.16<br>−0.18 |
| | | | Secreted interleukin 6 (IL-6) | 20.0 | −0.29 |
| | HD3CGF | Fibrosis chronic inflammation | Vascular cell adhesion molecule 1 (VCAM-1) | 20.0 | −0.28 |
| | | | Collagen I | 6.7<br>20.0 | −0.07<br>−0.13 |
| | | | Collagen III | 20.0 | −0.13 |
| | | | Interferon gamma-induced protein 10 (IP-10)/CXCL10 | 20.0 | −0.14 |
| | | | Interferon-inducible T cell alpha chemoattractant (I-TAC)/CXCL11 | 20.0 | −0.17 |
| | | | Monokine induced by gamma interferon (MIG)/CXCL9 | 20.0 | −0.10 |
| | | | Plasminogen activation inhibitor 1 (PAI-1) | 6.7<br>20.0 | −0.08<br>−0.13 |
| | | | 72-hour fibroblast proliferation | 6.7<br>20.0 | −0.67<br>−1.1 |
| Pentadecanoylcarnitine | 4H | Autoimmunity, allergy, asthma | Vascular endothelial growth factor s (VEGFR2) | 6.7 | −0.11 |
| | SAg | Chronic inflammation, autoimmune disease | E-selectin | 6.7 | −0.11 |
| | | | T cell proliferation | 6.7 | −0.17 |
| | BT | Asthma, oncology, autoimmunity, allergy | Secreted interleukin 2 (IL-1) | 2.2 | −0.11 |
| | | | Secreted interleukin 6 (IL-6) | 6.7 | −0.13 |
| | | | Tumor necrosis factor alpha (TNFα) | 6.7 | −0.10 |
| | BE3C | COPD, lung inflammation | Interferon gamma-induced protein 10 (IP-10)/CXCL10 | 6.7 | −0.1 |
| | | | Interferon-inducible T cell alpha chemoattractant (I-TAC)/CXCL11 | 0.7<br>2.2<br>6.7 | −0.13<br>−0.17<br>−0.54 |
| | | | Interleukin 8 (IL-8)/CXCL8 | 6.7 | −0.21 |
| | | | Monokine induced by gamma interferon (MIG)/CXCL9 | 6.7 | −0.60 |
| | | | Human leukocyte antigen-DR isotype (HLA-DR) | 6.7 | −0.63 |

TABLE 9-continued

| Compound | Human primary cell-based system | Disease systems | Biomarkers significantly lowered by compound | Active concentrations (μM) | Significant log10 reduction of biomarkers in treated systems compared to nontreated controls |
|---|---|---|---|---|---|
| | | | Interleukin 1 alpha (IL-1α) | 0.7 | −0.06 |
| | | | | 2.2 | −0.06 |
| | | | | 6.7 | −0.19 |
| | | | Matrix metalloproteinase 1 (MMP-1) | 2.2 | −0.05 |
| | | | | 6.7 | −0.27 |
| | | | Matrix metalloproteinase 9 (MMP-9) | 2.2 | −0.08 |
| | | | | 6.7 | −0.34 |
| | | | Plasminogen activation inhibitor 1 (PAI-1) | 2.2 | −0.08 |
| | | | | 6.7 | −0.24 |
| | | | Tissue plasminogen activator (tPA) | 2.2 | −0.11 |
| | | | | 6.7 | −0.43 |
| Pentadecanoylcarnitine | HDF3CGF | Fibrosis, chronic inflammation | Matrix metalloproteinase 1 (MMP-1) | 6.7 | −0.12 |
| | KF3CT | Dermatitis, psoriasis | Interferon gamma-induced protein 10 (IP-10)/CXCL10 | 0.7 | −0.14 |
| | | | | 2.2 | −0.09 |
| | | | | 6.7 | −0.10 |
| | MyoF | Wound healing, matrix remodeling, fibrosis, chronic inflammation | Alpha smooth muscle actin (αSMA) | 0.7 | −0.16 |
| | | | | 2.2 | −0.18 |
| | | | | 6.7 | −0.26 |
| | /Mphg | Chronic inflammation, restenosis, cardiovascular disease | Monocyte chemoattractant protein 1 (MCP-1) | 2.2 | −0.17 |
| | | | | 6.7 | −0.25 |
| | | | Secreted interleukin 10 (IL-10) | 6.7 | −0.13 |
| Xanthurenate | LPS | Chronic inflammation, cardiovascular disease | Secreted prostaglandin E2 (PGE2) | 6.7 | −0.16 |
| | | | | 20.0 | −0.09 |
| | BT | Asthma, oncology, autoimmunity, allergy | Tumor necrosis factor alpha (TNFα) | 20.0 | −0.19 |
| | | | Secreted interleukin 6 (IL-6) | 20.0 | −0.13 |

TABLE 10

Significantly reduced cell-based biomarkers relevant to specific diseases and conditions

| Clinical compound candidate | Th2 type inflammation | T-cell dependent B cell proliferation | Autoimmunity | Allergy | Asthma | Ulcerative colitis | Pulmonary fibrosis | COPD | SLE | Hematological oncology |
|---|---|---|---|---|---|---|---|---|---|---|
| 1-palmitoyl-2-arachidonoyl-GPC | x | x | x | x | x | | x | x | x | x |
| 10-heptadecanoate | x | x | x | x | x | | x | x | x | x |
| Lignoceroylcarnitine | x | x | x | x | x | | x | x | x | x |
| Pentadecanoylcarnitine | x | x | x | x | x | x | x | x | x | x |
| 4-hydroxyglutamate | | x | x | x | x | | | | x | x |
| 4-imidazoleacetate | | x | x | x | x | | | | x | x |
| 5-aminovalerate | | x | x | x | x | | | | x | x |
| 10-undecanoate | | x | x | x | x | | | | x | x |
| Gamma-glutamylglutamine | | x | x | x | x | | | | x | x |
| Gamma-glutamylglycine | | x | x | x | x | | | | x | x |
| N-acetylhistamine | | x | x | x | x | | | | x | x |
| Pentadecanoic acid | | x | x | x | x | | | | x | x |
| Xanthurenate | | x | x | x | x | | | | x | x |

TABLE 11

Significantly reduced cell-based biomarkers relevant to specific diseases and conditions

| Clinical compound candidate | Th1 type inflammation | Chronic inflammation | Atherosclerosis | Restenosis | Rheumatoid arthritis | Metabolic diseases | Organ transplantation | Psoriasis |
|---|---|---|---|---|---|---|---|---|
| 1-palmitoyl-2-arachidonoyl-GPC | x | x | x | x | x | | | x |
| 4-hydroxyglutamate | x | | | | x | | x | x |
| 4-imidazoleacetate | x | | | | x | | x | x |
| 5-aminovalerate | x | x | x | x | x | x | x | x |

TABLE 11-continued

Significantly reduced cell-based biomarkers relevant to specific diseases and conditions

| Clinical compound candidate | Th1 type inflammation | Chronic inflammation | Atherosclerosis | Restenosis | Rheumatoid arthritis | Metabolic diseases | Organ transplantation | Psoriasis |
|---|---|---|---|---|---|---|---|---|
| 10-heptadecanoate | x | x |  | x | x |  |  | x |
| 10-undecanoate | x | x | x | x | x | x | x | x |
| Gamma-glutamylglutamine | x | x | x | x | x |  | x | x |
| Gamma-glutamylglycine | x |  |  |  | x |  | x | x |
| Lignoceroylcarnitine | x | x | x | x | x |  |  |  |
| Methionine sulfone | x | x | x | x | x | x |  | x |
| N-acetylhistamine | x | x | x | x | x |  |  | x |
| Pentadecanoic acid | x | x |  |  | x |  | x | x |
| Pentadecanoylcarnitine | x | x | x | x | x |  | x | x |
| Xanthurenate | x | x | x | x | x | x |  |  |

TABLE 12

Significantly reduced cell-based biomarkers relevant to specific diseases and conditions

| Clinical compound candidate | Cutaneous responses to tissue damage | Crohn's disease | Hematological oncology | Sarcoidosis | Pulmonary responses to respiratory infections | Vascular inflammation | Fibrosis | Stromal biology in tumors |
|---|---|---|---|---|---|---|---|---|
| 1-palmitoyl-2-arachidonoyl-GPC |  |  |  | x | x |  | x | x |
| 4-hydroxyglutamate |  | x | x |  |  |  |  |  |
| 4-imidazoleacetate |  | x | x |  |  |  |  |  |
| 5-aminovalerate |  | x | x |  |  |  | x |  |
| 10-heptadecanoate |  |  |  |  |  | x | x | x |
| 10-undecanoate |  | x | x | x | x |  | x | x |
| Gamma-glutamylglutamine |  | x | x |  |  | x | x | x |
| Gamma-glutamylglycine |  | x | x |  |  |  |  |  |
| Lignoceroylcarnitine |  |  |  | x | x |  | x |  |
| Methionine sulfone |  |  |  |  |  | x | x | x |
| N-acetylhistamine |  |  |  |  |  |  | x | x |
| Pentadecanoic acid |  | x | x |  |  |  | x | x |
| Pentadecanoylcarnitine | x | x | x | x | x |  | x | x |

Exemplary Compositions, Uses, and Methods

Pharmaceutical Composition 1: A pharmaceutical composition for treatment or amelioration of aging or an aging-related condition negatively impacting longevity or quality of life, wherein the aging-related condition negatively impacting longevity or quality of life is selected from the group consisting of inflammation, anemia, hyperglycemia, dyslipidemia, hyperinsulinemia, liver disease, iron overload, hypertrigliceridemia, impaired skin integrity, wound healing, scarring, pain, allergies, sleep disorders and problems, gastrointestinal disorders and problems, Th1-type inflammation, Th2-type inflammation, an inflammatory disease involving T-cell dependent B cell proliferation, T-cell dependent B cell proliferation, allergy, asthma, atherosclerosis, autoimmunity, hypercholesterolemia, chronic inflammation, chronic obstructive pulmonary disease (COPD), Crohn's disease, cutaneous responses to tissue damage, fibrosis, hematological oncology, metabolic diseases, cardiovascular disease, organ transplantation, psoriasis, liver fibrosis, dermatitis, pulmonary fibrosis, pulmonary responses to respiratory infections, restenosis, rheumatoid arthritis, sarcoidosis, stromal biology in tumors, systemic lupus erythematosus (SLE), ulcerative colitis, vascular inflammation, and diseases that are driven or exacerbated by one or more factors selected from the group consisting of alpha smooth muscle actin (αSMA), CD40, CD69, collagen I, collagen III, decorin, e-selectin, eotaxin 3 (CCL26), fibroblast proliferation, human leukocyte antigen-DR isotype (HLA-DR), immunoglobulin G, interferon gamma-induced protein 10 (IP-10/CXCL10), interferon-inducible T cell alpha chemoattractant (I-TAC/CXCL11), interleukin (IL)-1, IL-1α, IL-2, IL-6, IL-8 (CXCL8), IL-10, IL-17A, IL-17F, keratin 8/81, macrophage colony-stimulating factor (M-CSF), matrix metalloproteinase (MMP)-1, MMP-9, monocyte chemoattractant protein 1 (MCP-1), monokine induced by gamma interferon (MIG/CXCL9), plasminogen activation inhibitor 1 (PAI-1), prostaglandin E2 (PGE2), serum amyloid A, T or B cell proliferation, tissue plasminogen activator (tPA), tumor necrosis factor alpha (TNFα), vascular cell adhesion molecule (VCAM-1), and vascular endothelial growth factor 2 (VEGFR2), the pharmaceutical composition comprising: one or more compounds selected from the group consisting of amino acids, peptides, carbohydrates, cofactors, vitamins, xenobiotics, lipids, and combinations thereof, or pharmaceutically acceptable salts, solvates, stereoisomers, or esters thereof; and a pharmaceutically acceptable carrier.

Pharmaceutical Composition 2: Pharmaceutical Composition 1, wherein the one or more compounds is pentadecanoylcarnitine.

Pharmaceutical Composition 3: Pharmaceutical Composition 2, wherein the aging-related condition negatively impacting longevity or quality of life is Th1-type inflammation.

Pharmaceutical Composition 4: Pharmaceutical Composition 3, wherein the Th1-type inflammation is lung inflammation.

Pharmaceutical Composition 5: Pharmaceutical Composition 3, wherein the Th1-type inflammation is chronic inflammation.

Pharmaceutical Composition 6: Pharmaceutical Composition 2, wherein the aging-related condition negatively impacting longevity or quality of life is dermatitis.

Pharmaceutical Composition 7: Pharmaceutical Composition 2, wherein the aging-related condition negatively impacting longevity or quality of life is psoriasis.

Pharmaceutical Composition 8: Pharmaceutical Composition 2, wherein the aging-related condition negatively impacting longevity or quality of life is cardiovascular disease.

Pharmaceutical Composition 9: Pharmaceutical Composition 2, wherein the aging-related condition negatively impacting longevity or quality of life is a fibrotic disease.

Pharmaceutical Composition 10: Pharmaceutical Composition 9, wherein the fibrotic disease is fibrotic liver disease.

Pharmaceutical Composition 11: Pharmaceutical Composition 9, wherein the fibrotic disease is fibrotic lung disease.

Pharmaceutical Composition 12: Pharmaceutical Composition 2, wherein the aging-related condition negatively impacting longevity or quality of life is anemia.

Pharmaceutical Composition 13: Pharmaceutical Composition 1, wherein the one or more compounds is methionine sulfone.

Pharmaceutical Composition 14: Pharmaceutical Composition 13, wherein the aging-related condition negatively impacting longevity or quality of life is Th1-type inflammation.

Pharmaceutical Composition 15: Pharmaceutical Composition 14, wherein the Th1-type inflammation is chronic inflammation.

Pharmaceutical Composition 16: Pharmaceutical Composition 13, wherein the aging-related condition negatively impacting longevity or quality of life is a fibrotic disease.

Pharmaceutical Composition 17: Pharmaceutical Composition 16, wherein the fibrotic disease is fibrotic liver disease.

Pharmaceutical Composition 18: Pharmaceutical Composition 13, wherein the aging-related condition negatively impacting longevity or quality of life is anemia.

Pharmaceutical Composition 19: Pharmaceutical Composition 13, wherein the aging-related condition negatively impacting longevity or quality of life is hypercholesterolemia.

Pharmaceutical Composition 20: Pharmaceutical Composition 1, wherein the one or more compounds is N-acetylhistamine.

Pharmaceutical Composition 21: Pharmaceutical Composition 20, wherein the aging-related condition negatively impacting longevity or quality of life is Th1-type inflammation.

Pharmaceutical Composition 22: Pharmaceutical Composition 21, wherein the Th1-type inflammation is chronic inflammation.

Pharmaceutical Composition 23: Pharmaceutical Composition 21, wherein the Th1-type inflammation is lung inflammation.

Pharmaceutical Composition 24: Pharmaceutical Composition 20, wherein the aging-related condition negatively impacting longevity or quality of life is an inflammatory disease involving T-cell dependent B cell proliferation.

Pharmaceutical Composition 25: Pharmaceutical Composition 20, wherein the aging-related condition negatively impacting longevity or quality of life is Th2-type inflammation.

Pharmaceutical Composition 26: Pharmaceutical Composition 25, wherein the Th2-type inflammation is lung inflammation.

Pharmaceutical Composition 27: Pharmaceutical Composition 20, wherein the aging-related condition negatively impacting longevity or quality of life is cardiovascular disease.

Pharmaceutical Composition 28: Pharmaceutical Composition 20, wherein the aging-related condition negatively impacting longevity or quality of life is a fibrotic disease.

Pharmaceutical Composition 29: Pharmaceutical Composition 28, wherein the fibrotic disease is fibrotic liver disease.

Pharmaceutical Composition 30: Pharmaceutical Composition 20, wherein the aging-related condition negatively impacting longevity or quality of life is anemia.

Pharmaceutical Composition 31: Pharmaceutical Composition 20, wherein the aging-related condition negatively impacting longevity or quality of life is hypercholesterolemia.

Pharmaceutical Composition 32: Pharmaceutical Composition 20, wherein the aging-related condition negatively impacting longevity or quality of life is hypertriglyceridemia.

Pharmaceutical Composition 33: Pharmaceutical Composition 20, wherein the aging-related condition negatively impacting longevity or quality of life is hyperinsulinemia.

Pharmaceutical Composition 34: Pharmaceutical Composition 1, wherein the one or more compounds is an amino acid.

Pharmaceutical Composition 35: Pharmaceutical Composition 34, wherein the amino acid is selected from the group consisting of 2-methylserine, 4-hydroxyglutamate, N-acetyl-aspartyl-glutamate, 2-pyrrolidinone, trans-urocanate, imidazole proprionate, 1-ribosyl-imidazoleacetate, 5-imidazoleacetate, N-acetylhistamine, hydantoin 5-prorionic acid, 5-hydroxylysine, 5-aminovalerate, 2-oxoadipate, xanthurenate, methionine sulfone, homocitrulline, trans-4-hydroxyproline, prolyl-hydroxyproline, guanidinosuccinate, and combinations thereof.

Pharmaceutical Composition 36: Pharmaceutical Composition 1, wherein the one or more compounds is a peptide.

Pharmaceutical Composition 37: Pharmaceutical Composition 36, wherein the peptide is selected from the group consisting of gamma-glutamylglutamine, gamma-glutamylglycine, and combinations thereof.

Pharmaceutical Composition 38: Pharmaceutical Composition 1, wherein the one or more compounds is a carbohydrate.

Pharmaceutical Composition 39: Pharmaceutical Composition 38, wherein the carbohydrate is N6-carboxymethyllysine.

Pharmaceutical Composition 40: Pharmaceutical Composition 1, wherein the one or more compounds is a cofactor or a vitamin.

Pharmaceutical Composition 41: Pharmaceutical Composition 40, wherein the cofactor or the vitamin is selected from the group consisting of N1-methyl-2-pyridone-5-carboxamide, N1-methyl-4-pyridone-3-carboxamide, and combinations thereof.

Pharmaceutical Composition 42: Pharmaceutical Composition 1, wherein the one or more compounds is a xenobiotic.

Pharmaceutical Composition 43: Pharmaceutical Composition 42, wherein the xenobiotic is 2,3-dihydroxyisovalerate.

Pharmaceutical Composition 44: Pharmaceutical Composition 1, wherein the one or more compounds is a monohydroxy acid.

Pharmaceutical Composition 45: Pharmaceutical Composition 44, wherein the monohydroxy acid is selected from the group consisting of 2-hydroxyoctanoate, 2-hydroxydecanoate, 8-hydroxyoctanoate, 2-hydroxymyristate, 16-hydroxypalmitate, or combinations thereof.

Pharmaceutical Composition 46: Pharmaceutical Composition 1, wherein the one or more compounds is a medium chain fatty acid.

Pharmaceutical Composition 47: Pharmaceutical Composition 46, wherein the medium chain fatty acid is selected from the group consisting of heptanoic acid, caprylic acid, pelargonic acid, undecanoic acid, 10-undecanoic acid, or combinations thereof.

Pharmaceutical Composition 48: Pharmaceutical Composition 1, wherein the one or more compounds is a long chain fatty acid.

Pharmaceutical Composition 49: Pharmaceutical Composition 48, wherein the long chain fatty acid is selected from the group consisting of pentadecanoic acid, margaric acid, 10-heptadecanoic acid, 10-nonadecanoic acid, a C20:0 fatty acid, C20:2 fatty acid, and combinations thereof.

Pharmaceutical Composition 50: Pharmaceutical Composition 1, wherein the one or more compounds is a very long chain fatty acid.

Pharmaceutical Composition 51: Pharmaceutical Composition 50, wherein the very long chain fatty acid is selected from the group consisting of C24:0 fatty acid, C24:1 fatty acid, and combinations thereof.

Pharmaceutical Composition 52: Pharmaceutical Composition 1, wherein the one or more compounds is a branched chain fatty acid.

Pharmaceutical Composition 53: Pharmaceutical Composition 52, wherein the branched chain fatty acid is selected from the group consisting of methylpalmitic acid, 17-methylstearic acid, 22-hydroxyphytanic acid, and combinations thereof.

Pharmaceutical Composition 54: Pharmaceutical Composition 1, wherein the one or more compounds is a dicarboxylate fatty acid.

Pharmaceutical Composition 55: Pharmaceutical Composition 54, wherein the dicarboxylate fatty acid is selected from the group consisting of dodecandioic acid, docosadioic acid, and combinations thereof.

Pharmaceutical Composition 56: Pharmaceutical Composition 1, wherein the one or more compounds is a product of fatty acid metabolism.

Pharmaceutical Composition 57: Pharmaceutical Composition 56, wherein the product of fatty acid metabolism is selected from the group consisting of propionylglycine, lignoceroylcarnitine, cerotoylcarnitine, N-palmitoylglycine, cis-4-decenoylcarnitine, behenoylcarnitine, pentadecanoylcarnitine, arachidonoylcholine, and combinations thereof.

Pharmaceutical Composition 58: Pharmaceutical Composition 1, wherein the one or more compounds is a phosphatidylcholine.

Pharmaceutical Composition 59: Pharmaceutical Composition 58, wherein the phosphatidylcholine is selected from the group consisting of 1-stearoyl-2-arachidonoyl-GPC (18:0/20:4), 1-palmitoyl-2-arachidonoyl-GPC (16:0/20:4n6), PC (18:2/22:4), PC (20:0/14:1), PC (20:0/20:3), PC (20:0/22:4), and combinations thereof.

Pharmaceutical Composition 60: Pharmaceutical Composition 1, wherein the one or more compounds is a phosphatidylethanolamine.

Pharmaceutical Composition 61: Pharmaceutical Composition 60, wherein the phosphatidylethanolamine is selected from the group consisting of 1-palmitoyl-2-arachidonoyl-GPE (16:0/20:4), 1-stearoyl-2-arachidonoyl-GPE (18:0/20:4), PE (16:0/16:0), and combinations thereof.

Pharmaceutical Composition 62: Pharmaceutical Composition 1, wherein the one or more compounds is a phosphatidylserine.

Pharmaceutical Composition 63: Pharmaceutical Composition 62, wherein the phosphatidylserine is 1-stearoyl-2-oleoyl-GPS (18:0/18:1).

Pharmaceutical Composition 64: Pharmaceutical Composition 1, wherein the one or more compounds is a lysophospholipid.

Pharmaceutical Composition 65: Pharmaceutical Composition 64, wherein the lysophospholipid is selected from the group consisting of 1-arachidonoyl-GPC (20:4n6), 1-lignoceroyl-GPC (24:0), 1-arachidonoyl-GPE (20:4n6), and combinations thereof.

Pharmaceutical Composition 66: Pharmaceutical Composition 1, wherein the one or more compounds is a plasmalogen.

Pharmaceutical Composition 67: Pharmaceutical Composition 66, wherein the plasmalogen is selected from the group consisting of 1-(1-enyl-palmitoyl)-2-arachidonoyl-GPE (P-16:0/20:4), 1-(1-enyl-palmitoyl)-2-oleoyl-GPC (P-16:0/18:1), 1-(1-enyl-palmitoyl)-2-arachidonoyl-GPC (P-16:0/20:4), 1-(1-enyl-stearoyl)-2-arachidonoyl-GPE (P-18:0/20:4), and combinations thereof.

Pharmaceutical Composition 68: Pharmaceutical Composition 1, wherein the one or more compounds is a lysoplasmalogen.

Pharmaceutical Composition 69: Pharmaceutical Composition 68, wherein the lysoplasmalogen is 1-(1-enyl-palmitoyl)-GPC (P-16:0).

Pharmaceutical Composition 70: Pharmaceutical Composition 1, wherein the one or more compounds is a monoacylglycerol.

Pharmaceutical Composition 71: Pharmaceutical Composition 70, wherein the monoacylglycerol is selected from the group consisting of MAG (12:0), MAG (17:0), MAG (20:0), MAG (20:2), 1-arachidonylglycerol (20:4), 1-heptadecenoylglycerol (17:1), and combinations thereof.

Pharmaceutical Composition 72: Pharmaceutical Composition 1, wherein the one or more compounds is a diacylglycerol.

Pharmaceutical Composition 73: Pharmaceutical Composition 72, wherein the diacylglycerol is selected from the group consisting of DAG (14:1/18:1), stearoyl-arachidonoyl-glycerol (18:0/20:4), oleoyl-arachidonoyl-glycerol (18:1/20:4), oleoyl-arachidonoyl-glycerol (18:1/20:4), and combinations thereof.

Pharmaceutical Composition 74: Pharmaceutical Composition 1, wherein the one or more compounds is a sphingomyelin.

Pharmaceutical Composition 75: Pharmaceutical Composition 74, wherein the sphingomyelin is selected from the group consisting of stearoyl sphingomyelin (d18:1/18:0), behenoyl sphingomyelin (d18:1/22:0), tricosanoyl sphingomyelin (d18:1/23:0), lignoceroyl sphingomyelin (d18:1/24:0), sphingomyelin (d18:2/23:1), sphingomyelin (d18:2/24:2), sphingomyelin (d17:1/14:0, d16:1/15:0), sphingomyelin (d17:1/16:0, d18:1/15:0, d16:1/17:0), sphingomyelin (d17:2/16:0, d18:2/15:0), sphingomyelin (d18:1/17:0, d17:1/18:0, d19:1/16:0), sphingomyelin (d18:1/19:0, d19:1/18:0), sphingomyelin (d18:1/21:0, d17:1/22:0, d16:1/23:0), sphingomyelin (d18:2/21:0, d16:2/23:0), sphingomyelin (d18:2/23:0, d18:1/23:1, d17:1/24:1), and combinations thereof.

Pharmaceutical Composition 76: Pharmaceutical Composition 1, wherein the one or more compounds is a ceramide.

Pharmaceutical Composition 77: Pharmaceutical Composition 76, wherein the ceramide is selected from the group consisting of CER (14:0), HCER (26:1), LCER (26:0), and combinations thereof.

Pharmaceutical Composition 78: Pharmaceutical Composition 1, wherein the one or more compounds is a β-sulfenyl derivative.

Pharmaceutical Composition 79: Pharmaceutical Composition 78, wherein the β-sulfenyl derivative is selected from the group consisting of β-sulfenyl acids, β-sulfenyl esters, and combinations thereof.

Pharmaceutical Composition 80: Pharmaceutical Composition 1, wherein the one or more compounds is a lipid metabolite.

Pharmaceutical Composition 81: Any one of Pharmaceutical Compositions 1 through 80, wherein the composition is in a unit dosage form.

Pharmaceutical Composition 82: Any one of Pharmaceutical Compositions 1 through 81, configured for administration of from 2.5 mg to 50 mg, per 1 kg of body weight, of the one or more compounds or pharmaceutically acceptable salts thereof to a patient.

Pharmaceutical Composition 83: Any one of Pharmaceutical Compositions 1 through 82, configured for administration once per day.

Pharmaceutical Composition 84: Any one of Pharmaceutical Compositions 1 through 83, comprising from 0.01 mg to 10000 mg of the one or more compounds or pharmaceutically acceptable salts thereof.

Pharmaceutical Composition 85: A pharmaceutical composition for treatment or amelioration of aging or aging-related conditions negatively impacting longevity or quality of life, wherein the conditions related to aging are selected from the group consisting of inflammation, anemia, hyperglycemia, dyslipidemia, hyperinsulinemia, liver disease, iron overload, hypertrigliceridemia, impaired skin integrity, wound healing, scarring, pain, allergies, sleep disorders and problems, gastrointestinal disorders and problems, Th1-type inflammation, Th2-type inflammation, an inflammatory disease involving T-cell dependent B cell proliferation, T-cell dependent B cell proliferation, allergy, asthma, atherosclerosis, autoimmunity, hypercholesterolemia, chronic inflammation, chronic obstructive pulmonary disease (COPD), Crohn's disease, cutaneous responses to tissue damage, fibrosis, hematological oncology, metabolic diseases, cardiovascular disease, organ transplantation, psoriasis, liver fibrosis, dermatitis, pulmonary fibrosis, pulmonary responses to respiratory infections, restenosis, rheumatoid arthritis, sarcoidosis, stromal biology in tumors, systemic lupus erythematosus (SLE), ulcerative colitis, vascular inflammation, and diseases that are driven or exacerbated by one or more factors selected from the group consisting of alpha smooth muscle actin (αSMA), CD40, CD69, collagen I, collagen III, decorin, e-selectin, eotaxin 3 (CCL26), fibroblast proliferation, human leukocyte antigen-DR isotype (HLA-DR), immunoglobulin G, interferon gamma-induced protein 10 (IP-10/CXCL10), interferon-inducible T cell alpha chemoattractant (I-TAC/CXCL11), interleukin (IL)-1, IL-1α, IL-2, IL-6, IL-8 (CXCL8), IL-10, IL-17A, IL-17F, keratin 8/81, macrophage colony-stimulating factor (M-CSF), matrix metalloproteinase (MMP)-1, MMP-9, monocyte chemoattractant protein 1 (MCP-1), monokine induced by gamma interferon (MIG/CXCL9), plasminogen activation inhibitor 1 (PAI-1), prostaglandin E2 (PGE2), serum amyloid A, T or B cell proliferation, tissue plasminogen activator (tPA), tumor necrosis factor alpha (TNFα), vascular cell adhesion molecule (VCAM-1), and vascular endothelial growth factor 2 (VEGFR2), the pharmaceutical composition comprising: one or more small molecule metabolites, or pharmaceutically acceptable salts, solvates, stereoisomers, or esters thereof; and a pharmaceutically acceptable carrier.

Pharmaceutical Composition 86: Pharmaceutical Composition 85, wherein the one or more small molecule metabolites is selected from the group consisting of amino acids, peptides, carbohydrates, cofactors and vitamins, xenobiotics, and lipids.

Pharmaceutical Composition 87: Any one of Pharmaceutical Compositions 85 or 86, wherein the one or more small molecule metabolites is capable of detection in serum at concentrations of from 1-10 nanomolar or 1-10 micromolar levels, has a low molecular weight of <900 daltons, and meets Lipinski's rule of five.

Use 88: Use of any one of Pharmaceutical Compositions 1 through 87, in the manufacture of a medicament for treatment or prophylaxis of inflammation, anemia, hyperglycemia, dyslipidemia, hyperinsulinemia, liver disease, iron overload, hypertrigliceridemia, impaired skin integrity, wound healing, scarring, pain, allergies, sleep disorders and problems, gastrointestinal disorders and problems, Th1-type inflammation, Th2-type inflammation, an inflammatory disease involving T-cell dependent B cell proliferation, T-cell dependent B cell proliferation, allergy, asthma, atherosclerosis, autoimmunity, hypercholesterolemia, chronic inflammation, chronic obstructive pulmonary disease (COPD), Crohn's disease, cutaneous responses to tissue damage, fibrosis, hematological oncology, metabolic diseases, cardiovascular disease, organ transplantation, psoriasis, liver fibrosis, dermatitis, pulmonary fibrosis, pulmonary responses to respiratory infections, restenosis, rheumatoid arthritis, sarcoidosis, stromal biology in tumors, systemic lupus erythematosus (SLE), ulcerative colitis, vascular inflammation, and diseases that are driven or exacerbated by one or more factors selected from the group consisting of alpha smooth muscle actin (αSMA), CD40, CD69, collagen I, collagen III, decorin, e-selectin, eotaxin 3 (CCL26), fibroblast proliferation, human leukocyte antigen-DR isotype (HLA-DR), immunoglobulin G, interferon gamma-induced protein 10 (IP-10/CXCL10), interferon-inducible T cell alpha chemoattractant (I-TAC/CXCL11), interleukin (IL)-1, IL-1α, IL-2, IL-6, IL-8 (CXCL8), IL-10, IL-17A, IL-17F, keratin 8/81, macrophage colony-stimulating factor (M-CSF), matrix metalloproteinase (MMP)-1, MMP-9, monocyte chemoattractant protein 1 (MCP-1), monokine induced by gamma interferon (MIG/CXCL9), plasminogen activation inhibitor 1 (PAI-1), prostaglandin E2 (PGE2), serum amyloid A, T or B cell proliferation, tissue plasminogen activator (tPA), tumor necrosis factor alpha (TNFα), vascular cell adhesion molecule (VCAM-1), and vascular endothelial growth factor 2 (VEGFR2).

Use 89: Use 88, wherein the pharmaceutical composition is configured to modulate a marker or a symptom of inflammation, anemia, hyperglycemia, dyslipidemia, hyperinsulinemia, liver disease, iron overload, hypertrigliceridemia, impaired skin integrity, wound healing, scarring, pain, allergies, sleep disorders and problems, gastrointestinal disorders and problems, Th1-type inflammation, Th2-type inflammation, an inflammatory disease involving T-cell dependent B cell proliferation, T-cell dependent B cell proliferation, allergy, asthma, atherosclerosis, autoimmunity, hypercholesterolemia, chronic inflammation, chronic obstructive pulmonary disease (COPD), Crohn's disease, cutaneous responses to tissue damage, fibrosis, hematological oncology, metabolic diseases, cardiovascular disease, organ transplantation, psoriasis, liver fibrosis, dermatitis, pulmonary fibrosis, pulmonary responses to respiratory infections, restenosis, rheumatoid arthritis, sarcoidosis, stromal biology in tumors, systemic lupus erythematosus (SLE), ulcerative colitis, vascular inflammation, and diseases that are driven or exacerbated by one or more factors selected from the group consisting of alpha smooth muscle actin (αSMA), CD40, CD69, collagen I, collagen III, decorin, e-selectin, eotaxin 3 (CCL26), fibroblast proliferation, human leukocyte antigen-DR isotype (HLA-DR), immunoglobulin G, interferon gamma-induced protein 10 (IP-10/CXCL10), interferon-inducible T cell alpha chemoattractant (I-TAC/CXCL11), interleukin (IL)-1, IL-1α, IL-2, IL-6, IL-8 (CXCL8), IL-10, IL-17A, IL-17F, keratin 8/81, macrophage colony-stimulating factor (M-CSF), matrix metalloproteinase (MMP)-1, MMP-9, monocyte chemoattractant protein 1 (MCP-1), monokine induced by gamma interferon (MIG/CXCL9), plasminogen activation inhibitor 1 (PAI-1), prostaglandin E2 (PGE2), serum amyloid A, T or B cell proliferation, tissue plasminogen activator (tPA), tumor necrosis factor alpha (TNFα), vascular cell adhesion molecule (VCAM-1), and vascular endothelial growth factor 2 (VEGFR2).

Use 90: Any one of Uses 88 through 89, wherein the marker of inflammation, anemia, hyperglycemia, dyslipidemia, hyperinsulinemia, liver disease, iron overload, hypertrigliceridemia, impaired skin integrity, wound healing, scarring, pain, allergies, sleep disorders and problems, gastrointestinal disorders and problems, Th1-type inflammation, Th2-type inflammation, an inflammatory disease involving T-cell dependent B cell proliferation, T-cell dependent B cell proliferation, allergy, asthma, atherosclerosis, autoimmunity, hypercholesterolemia, chronic inflammation, chronic obstructive pulmonary disease (COPD), Crohn's disease, cutaneous responses to tissue damage, fibrosis, hematological oncology, metabolic diseases, cardiovascular disease, organ transplantation, psoriasis, liver fibrosis, dermatitis, pulmonary fibrosis, pulmonary responses to respiratory infections, restenosis, rheumatoid arthritis, sarcoidosis, stromal biology in tumors, systemic lupus erythematosus (SLE), ulcerative colitis, vascular inflammation, and diseases that are driven or exacerbated by one or more factors selected from the group consisting of alpha smooth muscle actin (αSMA), CD40, CD69, collagen I, collagen III, decorin, e-selectin, eotaxin 3 (CCL26), fibroblast proliferation, human leukocyte antigen-DR isotype (HLA-DR), immunoglobulin G, interferon gamma-induced protein 10 (IP-10/CXCL10), interferon-inducible T cell alpha chemoattractant (I-TAC/CXCL11), interleukin (IL)-1, IL-1α, IL-2, IL-6, IL-8 (CXCL8), IL-10, IL-17A, IL-17F, keratin 8/81, macrophage colony-stimulating factor (M-CSF), matrix metalloproteinase (MMP)-1, MMP-9, monocyte chemoattractant protein 1 (MCP-1), monokine induced by gamma interferon (MIG/CXCL9), plasminogen activation inhibitor 1 (PAI-1), prostaglandin E2 (PGE2), serum amyloid A, T or B cell proliferation, tissue plasminogen activator (tPA), tumor necrosis factor alpha (TNFα), vascular cell adhesion molecule (VCAM-1), and vascular endothelial growth factor 2 (VEGFR2) is selected from the group consisting of serum, plasma, cell, or tissue levels of one or more small molecule metabolites.

Use 91: Any one of Uses 88 through 90, wherein the pharmaceutical composition is configured to increase a serum, plasma, or a red blood cell membrane concentration of the one or more small molecule metabolites is increased between 1.1 and 6 times a patient's baseline concentration and/or to a concentration greater than 0.5 μM and less than 30 μM.

Method 92: A method of treatment or prophylaxis of conditions related to aging, wherein the conditions related to aging are selected from the group consisting of inflammation, anemia, hyperglycemia, dyslipidemia, hyperinsulinemia, liver disease, iron overload, hypertrigliceridemia, impaired skin integrity, wound healing, scarring, pain, allergies, sleep disorders and problems, gastrointestinal disorders and problems, Th1-type inflammation, Th2-type inflammation, an inflammatory disease involving T-cell dependent B cell proliferation, T-cell dependent B cell proliferation, allergy, asthma, atherosclerosis, autoimmunity, hypercholesterolemia, chronic inflammation, chronic obstructive pulmonary disease (COPD), Crohn's disease, cutaneous responses to tissue damage, fibrosis, hematological oncology, metabolic diseases, cardiovascular disease, organ transplantation, psoriasis, liver fibrosis, dermatitis, pulmonary fibrosis, pulmonary responses to respiratory infections, restenosis, rheumatoid arthritis, sarcoidosis, stromal biology in tumors, systemic lupus erythematosus (SLE), ulcerative colitis, vascular inflammation, and diseases that are driven or exacerbated by one or more factors selected from the group consisting of alpha smooth muscle actin (αSMA), CD40, CD69, collagen I, collagen III, decorin, e-selectin, eotaxin 3 (CCL26), fibroblast proliferation, human leukocyte antigen-DR isotype (HLA-DR), immunoglobulin G, interferon gamma-induced protein 10 (IP-10/CXCL10), interferon-inducible T cell alpha chemoattractant (I-TAC/CXCL11), interleukin (IL)-1, IL-1α, IL-2, IL-6, IL-8 (CXCL8), IL-10, IL-17A, IL-17F, keratin 8/81, macrophage colony-stimulating factor (M-CSF), matrix metalloproteinase (MMP)-1, MMP-9, monocyte chemoattractant protein 1 (MCP-1), monokine induced by gamma interferon (MIG/CXCL9), plasminogen activation inhibitor 1 (PAI-1), prostaglandin E2 (PGE2), serum amyloid A, T or B cell proliferation, tissue plasminogen activator (tPA), tumor necrosis factor alpha (TNFα), vascular cell adhesion molecule (VCAM-1), and vascular endothelial growth factor 2 (VEGFR2), the method comprising: administering to a patient in need thereof, an effective amount of one or more compounds selected from the group consisting of amino acids, peptides, carbohydrates, cofactors, vitamins, xenobiotics, lipids, and combinations thereof, or pharmaceutically acceptable salts, solvates, stereoisomers, or esters thereof.

Method 92: Method 92, wherein the one or more compounds is pentadecanoylcarnitine.

Method 94: Method 93, wherein the aging-related condition negatively impacting longevity or quality of life is Th1-type inflammation.

Method 95: Method 94, wherein the Th1-type inflammation is lung inflammation.

Method 96: Method 94, wherein the Th1-type inflammation is chronic inflammation.

Method 97: Method 93, wherein the aging-related condition negatively impacting longevity or quality of life is dermatitis.

Method 98: Method 93, wherein the aging-related condition negatively impacting longevity or quality of life is psoriasis.

Method 99: Method 93, wherein the aging-related condition negatively impacting longevity or quality of life is cardiovascular disease.

Method 100: Method 93, wherein the aging-related condition negatively impacting longevity or quality of life is a fibrotic disease.

Method 101: Method 100, wherein the fibrotic disease is fibrotic liver disease.

Method 102: Method 100, wherein the fibrotic disease is fibrotic lung disease.

Method 103: Method 93, wherein the aging-related condition negatively impacting longevity or quality of life is anemia.

Method 104: Method 92, wherein the one or more compounds is methionine sulfone.

Method 105: Method 104, wherein the aging-related condition negatively impacting longevity or quality of life is Th1-type inflammation.

Method 106: Method 105, wherein the Th1-type inflammation is chronic inflammation.

Method 107: Method 104, wherein the aging-related condition negatively impacting longevity or quality of life is a fibrotic disease.

Method 108: Method 107, wherein the fibrotic disease is fibrotic liver disease.

Method 109: Method 104, wherein the aging-related condition negatively impacting longevity or quality of life is anemia.

Method 110: Method 104, wherein the aging-related condition negatively impacting longevity or quality of life is hypercholesterolemia.

Method 111: Method 92, wherein the one or more compounds is N-acetylhistamine.

Method 112: Method 111, wherein the aging-related condition negatively impacting longevity or quality of life is Th1-type inflammation.

Method 113: Method 112, wherein the Th1-type inflammation is chronic inflammation.

Method 114: Method 112, wherein the Th1-type inflammation is lung inflammation.

Method 115: Method 111, wherein the aging-related condition negatively impacting longevity or quality of life is an inflammatory disease involving T-cell dependent B cell proliferation.

Method 116: Method 111, wherein the aging-related condition negatively impacting longevity or quality of life is Th2-type inflammation.

Method 117: Method 116, wherein the Th2-type inflammation is lung inflammation.

Method 118: Method 111, wherein the aging-related condition negatively impacting longevity or quality of life is cardiovascular disease.

Method 119: Method 111, wherein the aging-related condition negatively impacting longevity or quality of life is a fibrotic disease.

Method 120: Method 119, wherein the fibrotic disease is fibrotic liver disease.

Method 121: Method 111, wherein the aging-related condition negatively impacting longevity or quality of life is anemia.

Method 122: Method 111, wherein the aging-related condition negatively impacting longevity or quality of life is hypercholesterolemia.

Method 123: Method 111, wherein the aging-related condition negatively impacting longevity or quality of life is hypertriglicerodemia.

Method 124: Method 111, wherein the aging-related condition negatively impacting longevity or quality of life is hyperinsulinemia.

Method 125: Method 92, wherein the one or more compounds is an amino acid.

Method 126: Method 125, wherein the amino acid is selected from the group consisting of 2-methylserine, 4-hydroxyglutamate, N-acetyl-aspartyl-glutamate, 2-pyrrolidinone, trans-urocanate, imidazole proprionate, 1-ribosyl-imidazoleacetate, 5-imidazoleacetate, N-acetylhistamine, hydantoin 5-prorionic acid, 5-hydroxylysine, 5-aminovalerate, 2-oxoadipate, xanthurenate, methionine sulfone, homocitrulline, trans-4-hydroxyproline, prolyl-hydroxyproline, guanidinosuccinate, and combinations thereof.

Method 127: Method 92, wherein the one or more compounds is a peptide.

Method 128: Method 127, wherein the peptide is selected from the group consisting of gamma-glutamylglutamine, gamma-glutamylglycine, and combinations thereof.

Method 129: Method 92, wherein the one or more compounds is a carbohydrate.

Method 130: Method 129, wherein the carbohydrate is N6-carboxymethyllysine.

Method 131: Method 92, wherein the one or more compounds is a cofactor or a vitamin.

Method 132: Method 131, wherein the cofactor or the vitamin is selected from the group consisting of N1-methyl-2-pyridone-5-carboxamide, N1-methyl-4-pyridone-3-carboxamide, and combinations thereof.

Method 133: Method 92, wherein the one or more compounds is a xenobiotic.

Method 134: Method 133, wherein the xenobiotic is 2,3-dihydroxyisovalerate.

Method 135: Method 92, wherein the one or more compounds is a monohydroxy acid.

Method 136: Method 135, wherein the monohydroxy acid is selected from the group consisting of 2-hydroxyoctanoate, 2-hydroxydecanoate, 8-hydroxyoctanoate, 2-hydroxymyristate, 16-hydroxypalmitate, or combinations thereof.

Method 137: Method 92, wherein the one or more compounds is a medium chain fatty acid.

Method 138: Method 137, wherein the medium chain fatty acid is selected from the group consisting of heptanoic acid, caprylic acid, pelargonic acid, undecanoic acid, 10-undecanoic acid, or combinations thereof.

Method 139: Method 92, wherein the one or more compounds is a long chain fatty acid.

Method 140: Method 139, wherein the long chain fatty acid is selected from the group consisting of pentadecanoic acid, margaric acid, 10-heptadecanoic acid, 10-nonadecanoic acid, a C20:0 fatty acid, C20:2 fatty acid, and combinations thereof.

Method 141: Method 92, wherein the one or more compounds is a very long chain fatty acid.

Method 142: Method 141, wherein the very long chain fatty acid is selected from the group consisting of C24:0 fatty acid, C24:1 fatty acid, and combinations thereof.

Method 143: Method 92, wherein the one or more compounds is a branched chain fatty acid.

Method 144: Method 143, wherein the branched chain fatty acid is selected from the group consisting of methylpalmitic acid, 17-methylstearic acid, 22-hydroxyphytanic acid, and combinations thereof.

Method 145: Method 92, wherein the one or more compounds is a dicarboxylate fatty acid.

Method 146: Method 145, wherein the dicarboxylate fatty acid is selected from the group consisting of dodecandioic acid, docosadioic acid, and combinations thereof.

Method 147: Method 92, wherein the one or more compounds is a product of fatty acid metabolism.

Method 148: Method 147, wherein the product of fatty acid metabolism is selected from the group consisting of propionylglycine, lignoceroylcarnitine, cerotoylcarnitine, N-palmitoylglycine, cis-4-decenoylcarnitine, behenoylcarnitine, pentadecanoylcarnitine, arachidonoylcholine, and combinations thereof.

Method 149: Method 92, wherein the one or more compounds is a phosphatidylcholine.

Method 150: Method 149, wherein the phosphatidylcholine is selected from the group consisting of 1-stearoyl-2-arachidonoyl-GPC (18:0/20:4), 1-palmitoyl-2-arachidonoyl-GPC (16:0/20:4n6), PC (18:2/22:4), PC (20:0/14:1), PC (20:0/20:3), PC (20:0/22:4), and combinations thereof.

Method 151: Method 92, wherein the one or more compounds is a phosphatidylethanolamine.

Method 152: Method 151, wherein the phosphatidylethanolamine is selected from the group consisting of 1-palmitoyl-2-arachidonoyl-GPE (16:0/20:4), 1-stearoyl-2-arachidonoyl-GPE (18:0/20:4), PE (16:0/16:0), and combinations thereof.

Method 153: Method 92, wherein the one or more compounds is a phosphatidylserine.

Method 154: Method 153, wherein the phosphatidylserine is 1-stearoyl-2-oleoyl-GPS (18:0/18:1).

Method 155: Method 92, wherein the one or more compounds is a lysophospholipid.

Method 156: Method 155, wherein the lysophospholipid is selected from the group consisting of 1-arachidonoyl-GPC (20:4n6), 1-lignoceroyl-GPC (24:0), 1-arachidonoyl-GPE (20:4n6), and combinations thereof.

Method 157: Method 92, wherein the one or more compounds is a plasmalogen.

Method 158: Method 157, wherein the plasmalogen is selected from the group consisting of 1-(1-enyl-palmitoyl)-2-arachidonoyl-GPE (P-16:0/20:4), 1-(1-enyl-palmitoyl)-2-oleoyl-GPC (P-16:0/18:1), 1-(1-enyl-palmitoyl)-2-arachidonoyl-GPC (P-16:0/20:4), 1-(1-enyl-stearoyl)-2-arachidonoyl-GPE (P-18:0/20:4), and combinations thereof.

Method 159: Method 92, wherein the one or more compounds is a lysoplasmalogen.

Method 160: Method 159, wherein the lysoplasmalogen is 1-(1-enyl-palmitoyl)-GPC (P-16:0).

Method 161: Method 92, wherein the one or more compounds is a monoacylglycerol.

Method 162: Method 161, wherein the monoacylglycerol is selected from the group consisting of MAG (12:0), MAG (17:0), MAG (20:0), MAG (20:2), 1-arachidonylglycerol (20:4), 1-heptadecenoylglycerol (17:1), and combinations thereof.

Method 163: Method 92, wherein the one or more compounds is a diacylglycerol.

Method 164: Method 163, wherein the diacylglycerol is selected from the group consisting of DAG (14:1/18:1), stearoyl-arachidonoyl-glycerol (18:0/20:4), oleoyl-arachidonoyl-glycerol (18:1/20:4), oleoyl-arachidonoyl-glycerol (18:1/20:4), and combinations thereof.

Method 165: Method 92, wherein the one or more compounds is a sphingomyelin.

Method 166: Method 165, wherein the sphingomyelin is selected from the group consisting of stearoyl sphingomyelin (dl 8:1/18:0), behenoyl sphingomyelin (d18:1/22:0), tricosanoyl sphingomyelin (d18:1/23:0), lignoceroyl sphingomyelin (d18:1/24:0), sphingomyelin (d18:2/23:1), sphingomyelin (d18:2/24:2), sphingomyelin (d17:1/14:0, d16:1/15:0), sphingomyelin (d17:1/16:0, d18:1/15:0, d16:1/17:0), sphingomyelin (d17:2/16:0, d18:2/15:0), sphingomyelin (d18:1/17:0, d17:1/18:0, d19:1/16:0), sphingomyelin (d18: 1/19:0, d19:1/18:0), sphingomyelin (d18:1/21:0, d17:1/22:0, d16:1/23:0), sphingomyelin (d18:2/21:0, d16:2/23:0), sphingomyelin (d18:2/23:0, d18:1/23:1, d17:1/24:1), and combinations thereof.

Method 167: Method 92, wherein the one or more compounds is a ceramide.

Method 168: Method 167, wherein the ceramide is selected from the group consisting of CER (14:0), HCER (26:1), LCER (26:0), and combinations thereof.

Method 169: Method 92, wherein the one or more compounds is a β-sulfenyl derivative.

Method 170: Method 169, wherein the β-sulfenyl derivative is selected from the group consisting of β-sulfenyl acids, β-sulfenyl esters, and combinations thereof.

Method 171: Method 92, wherein the one or more compounds is a lipid metabolite.

Method 172: Any one of Methods 92 to 171, wherein the one or more compounds or pharmaceutically acceptable salts, solvates, stereoisomers, or esters thereof is provided as a pharmaceutical composition in a unit dosage form comprising the one or more compounds or pharmaceutically acceptable salts thereof and a pharmaceutically acceptable carrier.

Method 173: Method 172, wherein the unit dosage form comprises from 0.01 mg to 10000 mg of the one or more compounds or pharmaceutically acceptable salts thereof.

Method 174: Method 92, wherein the one or more compounds is an amino acid or lipid.

Method 175: Any one of Methods 92 to 174, wherein the one or more compounds comprises a plurality different compounds.

Method 176: Any one of Methods 92 to 175, wherein from 2.5 mg to 50 mg of the one or more compounds or pharmaceutically acceptable salts, solvates, stereoisomers, or esters thereof is administered to the patient, per 1 kg of body weight, per day.

Method 177: Any one of Methods 92 to 176, wherein the one or more compounds or pharmaceutically acceptable salts, solvates, stereoisomers, or esters thereof is administered to the patient once per day.

Method 178: Any one of Methods 92 to 177, wherein a serum, plasma, red blood cell, or tissue concentration of the one or more compounds is increased between 1.1 and 6 times a patient's baseline concentration and/or to a concentration greater than 0.5 μM and less than 30 μM.

Method 179: A method of treatment or prophylaxis of conditions related to aging, wherein the conditions related to aging are selected from the group consisting of inflammation, anemia, hyperglycemia, dyslipidemia, hyperinsulinemia, liver disease, iron overload, hypertrigliceridemia, impaired skin integrity, wound healing, scarring, pain, allergies, sleep disorders and problems, gastrointestinal disorders and problems, Th1-type inflammation, Th2-type inflammation, an inflammatory disease involving T-cell dependent B cell proliferation, T-cell dependent B cell proliferation, allergy, asthma, atherosclerosis, autoimmunity, hypercholesterolemia, chronic inflammation, chronic obstructive pulmonary disease (COPD), Crohn's disease, cutaneous responses to tissue damage, fibrosis, hematological oncology, metabolic diseases, cardiovascular disease, organ transplantation, psoriasis, liver fibrosis, dermatitis, pulmonary fibrosis, pulmonary responses to respiratory infections, restenosis, rheumatoid arthritis, sarcoidosis, stromal biology in tumors, systemic lupus erythematosus (SLE), ulcerative colitis, vascular inflammation, and diseases that are driven or exacerbated by one or more factors selected from the group consisting of alpha smooth muscle actin (αSMA), CD40, CD69, collagen I, collagen III, decorin, e-selectin, eotaxin 3 (CCL26), fibroblast proliferation, human leukocyte antigen-DR isotype (HLA-DR), immunoglobulin G, interferon gamma-induced protein 10 (IP-10/CXCL10), interferon-inducible T cell alpha chemoattractant (I-TAC/CXCL11), interleukin (IL)-1, IL-1α, IL-2, IL-6, IL-8 (CXCL8), IL-10, IL-17A, IL-17F, keratin 8/81, macrophage colony-stimulating factor (M-CSF), matrix metalloproteinase (MMP)-1, MMP-9, monocyte chemoattractant protein 1 (MCP-1), monokine induced by gamma interferon (MIG/CXCL9), plasminogen activation inhibitor 1 (PAI-1), prostaglandin E2 (PGE2), serum amyloid A, T or B cell proliferation, tissue plasminogen activator (tPA), tumor necrosis factor alpha (TNFα), vascular cell adhesion molecule (VCAM-1), and vascular endothelial growth factor 2 (VEGFR2), the method comprising: administering to a patient in need thereof, an effective amount of one or more small molecule metabolites, or pharmaceutically acceptable salts, solvates, stereoisomers, or esters thereof.

Method 180: Method 179, wherein the one or more small molecule metabolites is selected from the group consisting of amino acids, peptides, carbohydrates, cofactors and vitamins, xenobiotics, and lipids.

Method 181: Any one of Methods 179 or 180, wherein the one or more small molecule metabolites is capable of detection in serum at concentrations of from 1-10 nanomolar or 1-10 micromolar levels, has a low molecular weight of <900 daltons, and meets Lipinski's rule of five.

Method 182: Any one of Methods 179 or 181, further comprising detecting the one or more small molecule metabolites in serum.

Method 183: Any one of Methods 92 to 182, wherein a marker or symptom is modulated wherein the marker or the symptom is selected from the group consisting of a symptom of inflammation, anemia, hyperglycemia, dyslipidemia, hyperinsulinemia, liver disease, iron overload, hypertriglyceridemia, impaired skin integrity, wound healing, scarring, pain, allergies, sleep disorders and problems, gastrointestinal disorders and problems, Th1-type inflammation, Th2-type inflammation, an inflammatory disease involving T-cell dependent B cell proliferation, T-cell dependent B cell proliferation, allergy, asthma, atherosclerosis, autoimmunity, hypercholesterolemia, chronic inflammation, chronic obstructive pulmonary disease (COPD), Crohn's disease, cutaneous responses to tissue damage, fibrosis, hematological oncology, metabolic diseases, cardiovascular disease, organ transplantation, psoriasis, liver fibrosis, dermatitis, pulmonary fibrosis, pulmonary responses to respiratory infections, restenosis, rheumatoid arthritis, sarcoidosis, stromal biology in tumors, systemic lupus erythematosus (SLE), ulcerative colitis, vascular inflammation, and diseases that are driven or exacerbated by one or more factors selected from the group consisting of alpha smooth muscle actin (αSMA), CD40, CD69, collagen I, collagen III, decorin, e-selectin, eotaxin 3 (CCL26), fibroblast proliferation, human leukocyte antigen-DR isotype (HLA-DR), immunoglobulin G, interferon gamma-induced protein 10 (IP-10/CXCL10), interferon-inducible T cell alpha chemoattractant (I-TAC/CXCL11), interleukin (IL)-1, IL-1α, IL-2, IL-6, IL-8 (CXCL8), IL-10, IL-17A, IL-17F, keratin 8/81, macrophage colony-stimulating factor (M-CSF), matrix metalloproteinase (MMP)-1, MMP-9, monocyte chemoattractant protein 1 (MCP-1), monokine induced by gamma interferon (MIG/CXCL9), plasminogen activation inhibitor 1 (PAI-1), prostaglandin E2 (PGE2), serum amyloid A, T or B cell proliferation, tissue plasminogen activator (tPA), tumor necrosis factor alpha (TNFα), vascular cell adhesion molecule (VCAM-1), and vascular endothelial growth factor 2 (VEGFR2).

Method 184: Method 183, wherein the marker of inflammation, anemia, hyperglycemia, dyslipidemia, hyperinsulinemia, liver disease, iron overload, hypertriglyceridemia, impaired skin integrity, wound healing, scarring, pain, allergies, sleep disorders and problems, gastrointestinal disorders and problems, Th1-type inflammation, Th2-type inflammation, an inflammatory disease involving T-cell dependent B cell proliferation, T-cell dependent B cell proliferation, allergy, asthma, atherosclerosis, autoimmunity, hypercholesterolemia, chronic inflammation, chronic obstructive pulmonary disease (COPD), Crohn's disease, cutaneous responses to tissue damage, fibrosis, hematological oncology, metabolic diseases, cardiovascular disease, organ transplantation, psoriasis, liver fibrosis, dermatitis, pulmonary fibrosis, pulmonary responses to respiratory infections, restenosis, rheumatoid arthritis, sarcoidosis, stromal biology in tumors, systemic lupus erythematosus (SLE), ulcerative colitis, vascular inflammation, and diseases that are driven or exacerbated by one or more factors selected from the group consisting of alpha smooth muscle actin (αSMA), CD40, CD69, collagen I, collagen III, decorin, e-selectin, eotaxin 3 (CCL26), fibroblast proliferation, human leukocyte antigen-DR isotype (HLA-DR), immunoglobulin G, interferon gamma-induced protein 10 (IP-10/CXCL10), interferon-inducible T cell alpha chemoattractant (I-TAC/CXCL11), interleukin (IL)-1, IL-1α, IL-2, IL-6, IL-8 (CXCL8), IL-10, IL-17A, IL-17F, keratin 8/81, macrophage colony-stimulating factor (M-CSF), matrix metalloproteinase (MMP)-1, MMP-9, monocyte chemoattractant protein 1 (MCP-1), monokine induced by gamma interferon (MIG/CXCL9), plasminogen activation inhibitor 1 (PAI-1), prostaglandin E2 (PGE2), serum amyloid A, T or B cell proliferation, tissue plasminogen activator (tPA), tumor necrosis factor alpha (TNFα), vascular cell adhesion molecule (VCAM-1), and vascular endothelial growth factor 2 (VEGFR2) is selected from the group consisting of serum, plasma, cell, or tissue levels of one or more small molecule metabolites.

Method 184: Any one of Methods 179 to 184, wherein a serum, plasma, or a red blood cell membrane concentration of the one or more small molecule metabolites is increased between 1.1 and 6 times a patient's baseline concentration and/or to a concentration greater than 0.5 µM and less than 30 µM.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for treatment or amelioration of aging or an aging-related condition negatively impacting longevity or quality of life, wherein the aging-related condition negatively impacting longevity or quality of life is autoimmunity, comprising:
   administering to a patient in need thereof pentadecanoylcarnitine, or pharmaceutically acceptable salts, solvates, stereoisomers, or esters thereof
   wherein the autoimmunity is rheumatoid arthritis, multiple sclerosis, Crohn disease, systemic lupus erythematosus, psoriasis, type 1 diabetes, hematological oncology, asthma, allergy, or ulcerative colitis.

2. The method of claim 1, wherein the pentadecanoylcarnitine or pharmaceutically acceptable salts thereof is administered in a unit dosage form, in a form of a supplement, in a form of a foodstuff, or in a form of a prescription therapeutic.

3. The method of claim 1, wherein the pentadecanoylcarnitine or pharmaceutically acceptable salts thereof is administered to a patient at from 0.5 mg to 50 mg, per 1 kg of body weight.

4. The method of claim 1, wherein the pentadecanoylcarnitine or pharmaceutically acceptable salts thereof is administered once per day.

5. The method of claim 1, wherein from 0.01 mg to 10000 mg of the pentadecanoylcarnitine or pharmaceutically acceptable salts thereof is administered.

6. The method of claim 1, wherein the autoimmunity is rheumatoid arthritis.

7. The method of claim 1, wherein the autoimmunity is multiple sclerosis.

8. The method of claim 1, wherein the autoimmunity is Crohn disease.

9. The method of claim 1, wherein the autoimmunity is systemic lupus.

10. The method of claim 1, wherein the autoimmunity is erythematosus.

11. The method of claim 1, wherein the autoimmunity is psoriasis.

12. The method of claim 1, wherein the autoimmunity is type 1 diabetes.

13. The method of claim 1, wherein the autoimmunity is hematological oncology.

14. The method of claim 1, wherein the autoimmunity is asthma.

15. The method of claim 1, wherein the autoimmunity is allergy.

16. The method of claim 1, wherein the autoimmunity is ulcerative colitis.

17. The method of claim 1, wherein the pentadecanoylcarnitine or pharmaceutically acceptable salts thereof is administered topically or to a mucous membrane.

18. The method of claim 1, wherein the pentadecanoylcarnitine or pharmaceutically acceptable salts thereof is administered with one or more therapeutic agents selected from the group consisting of antibacterial drugs, antiprotozoal drugs, antifungal drugs, antiviral drugs, spermicidal agents, prostaglandins, and steroids.

19. The method of claim 1, wherein the patient is a human.

20. The method of claim 1, wherein the patient is a mammal selected from the group consisting of dolphins, mice, rats, rabbits, guinea pigs, dogs, cats, sheep, goats, cows, horses, monkeys, chimpanzees, and apes.

* * * * *

UNITED STATES PATENT AND TRADEMARK OFFICE
CERTIFICATE OF CORRECTION

| | |
|---|---|
| PATENT NO. | : 11,992,473 B2 |
| APPLICATION NO. | : 17/086165 |
| DATED | : May 28, 2024 |
| INVENTOR(S) | : Stephanie Venn-Watson |

It is certified that error appears in the above-identified patent and that said Letters Patent is hereby corrected as shown below:

On the Title Page

On Page 2, Column 2, under Other Publications, Line 22, delete "chinensisrhizome" and insert --chinensis rhizome--.

On Page 3, Column 1, under Other Publications, Line 49, delete ""Hemochronatosis" and insert --"Hemochromatosis--.

On Page 4, Column 1, under Other Publications, Line 17, delete "Neuroinflammunol." and insert --Neuroimmunol.--.

On Page 4, Column 2, under Other Publications, Line 11, delete "phytohemagllutinin" and insert --phytohemagglutinin--.

On Page 4, Column 2, under Other Publications, Line 26, delete "Cardiovsc" and insert --Cardiovasc--.

On Page 4, Column 2, under Other Publications, Line 40, delete "Sauid" and insert --Saudi--.

On Page 4, Column 2, under Other Publications, Line 60, delete "ofType" and insert --of Type--.

On Page 5, Column 1, under Other Publications, Line 42, delete "adposity" and insert --adiposity--.

On Page 5, Column 2, under Other Publications, Line 9, delete "Fuid." and insert --Fluid.--.

On Page 6, Column 1, under Other Publications, Line 42, delete "reduces" and insert --reduces liver fat content in--.

On Page 6, Column 1, under Other Publications, Line 64, delete "Hapatitis" and insert --Hepatitis--.

Signed and Sealed this
Fifteenth Day of July, 2025

Coke Morgan Stewart
*Acting Director of the United States Patent and Trademark Office*

CERTIFICATE OF CORRECTION (continued)

U.S. Pat. No. 11,992,473 B2

On Page 6, Column 2, under Other Publications, Line 62, delete "forinsulin" and insert --for insulin--.

On Page 7, Column 2, under Other Publications, Line 47, delete "Biologies." and insert --Biologics.--.

On Page 9, Column 2, under Other Publications, Line 9, delete "endocannabinoide-" and insert --endocannabinoidome- --.

On Page 9, Column 2, under Other Publications, Line 53, delete "COX01" and insert --COX-1--.

In the Drawings

On Sheet 4 of 9 (Figure 4), Line 7 (Approx.), delete "xanthenurate" and insert --xanthurenate--.

In the Specification

In Column 4, Line 51, delete "FIG. 1." and insert --FIG. 1--.

In Column 7, Line 60, delete "benzodiazapines" and insert --benzodiazepines--.

In Column 7, Line 65, delete "Biologies)." and insert --Biologics).--.

In Column 9, Line 34, delete "exzcema," and insert --eczema,--.

In Column 9, Line 35, delete "carsinoma," and insert --carcinoma,--.

In Column 15, Line 37, delete "proprionate," and insert --propionate,--.

In Column 15, Line 39, delete "prorionic" and insert --propionic--.

In Column 15, Line 54, delete "monohyroxy" and insert --monohydroxy--.

In Column 15, Line 55, delete "hydroxyocatnoate," and insert --hydroxyoctanoate,--.

In Column 16, Line 9 (Approx.), delete "dodecandioic" and insert --dodecanedioic--.

In Column 22, Line 66, delete "carragenans," and insert --carrageenans,--.

In Column 23, Line 57, delete "ethoxolated" and insert --ethoxylated--.

In Column 23, Line 59, delete "recinoleate," and insert --ricinoleate,--.

In Column 23, Line 60, delete "recinoleate," and insert --ricinoleate,--.

In Column 23, Line 60, delete "recinoleate," and insert --ricinoleate,--.

In Column 26, Line 43, delete "melenamic" and insert --mefenamic--.

In Column 26, Line 47, delete "betamethesone," and insert --betamethasone,--.

In Column 34, Line 18, delete "ng" and insert --ng/ml.--.

In Column 37, Line 22, delete "(HanAII" and insert --(HanAll--.

In Column 38, Line 23, delete "melanocoritin" and insert --melanocortin--.

In Column 40, Line 9, delete "exopipam;" and insert --ecopipam;--.

In Column 40, Line 15, delete "amfebutmone;" and insert --amfebutamone;--.

In Column 41, Line 20, delete "ferrus" and insert --ferrous--.

In Column 41, Line 22, delete "ferrus" and insert --ferrous--.

In Column 45, Line 33 (Approx.), delete "Shimazdu" and insert --Shimadzu--.

In Column 45, Line 34 (Approx.), delete "Selexlon" and insert --Selexion--.

In Column 51, Line 17, delete "Florida" and insert --Florida.--.

In Column 52, Line 30, delete "FIG. 1." and insert --FIG. 1--.

In Columns 55-56 (TABLE 6), Line 2, delete "fife" and insert --life--.

In Columns 55-56 (TABLE 6), Line 39, delete "il7" and insert --(i17--.

In Columns 55-56 (TABLE 6), Line 40, delete "il9" and insert --(i19--.

In Columns 57-58 (TABLE 6-Continued), Line 2, delete "fife" and insert --life--.

In Columns 57-58 (TABLE 6-Continued), Line 47, delete "24:l)" and insert --24:1)--.

In Column 59, Line 52, delete "Shimazdu" and insert --Shimadzu--.

In Column 59, Line 53, delete "Selexlon" and insert --Selexion--.

In Column 62, Line 48, delete "glutmylglycine," and insert --glutamylglycine,--.

In Column 69-70 (TABLE 9-Continued), Line 28 (Approx.), delete "(IL-17A)?" and insert --(IL-17A)--.

In Column 75, Line 47, delete "hypertrigliceridemia," and insert --hypertriglyceridemia,--.

In Column 78, Line 24-25, delete "hypertrigliceridemia." and insert --hypertriglyceridemia.--.

CERTIFICATE OF CORRECTION (continued)
U.S. Pat. No. 11,992,473 B2

In Column 78, Line 37 (Approx.), delete "proprionate," and insert --propionate,--.

In Column 78, Lines 38-39 (Approx.), delete "prorionic" and insert --propionic--.

In Column 79, Line 45, delete "dodecandioic" and insert --dodecanedioic--.

In Column 81, Line 40, delete "hypertrigliceridemia," and insert --hypertriglyceridemia,--.

In Column 82, Line 25, delete "hypertrigliceridemia," and insert --hypertriglyceridemia,--.

In Column 82, Line 61, delete "hypertrigliceridemia," and insert --hypertriglyceridemia,--.

In Column 83, Line 29-30, delete "hypertrigliceridemia," and insert --hypertriglyceridemia,--.

In Column 84, Line 9 (Approx.), delete "hypertrigliceridemia," and insert --hypertriglyceridemia,--.

In Column 85, Line 64, delete "hypertrigliceridemia." and insert --hypertriglyceridemia.--.

In Column 86, Line 6, delete "proprionate," and insert --propionate,--.

In Column 86, Line 8, delete "prorionic" and insert --propionic--.

In Column 86, Line 64, delete "dodecandioic" and insert --dodecanedioic--.

In Column 88, Line 50, delete "hypertrigliceridemia," and insert --hypertriglyceridemia,--.

In Column 89, Lines 37-38, delete "hypertrigliceridemia," and insert --hypertriglyceridemia,--.

In Column 90, Line 6, delete "hypertrigliceridemia," and insert --hypertriglyceridemia,--.